United States Patent
Abela et al.

(10) Patent No.: US 12,421,251 B2
(45) Date of Patent: Sep. 23, 2025

(54) CYSTIC FIBROSIS TRANSMEMBRANE CONDUCTANCE REGULATOR MODULATING AGENTS

(71) Applicant: VERTEX PHARMACEUTICALS INCORPORATED, Boston, MA (US)

(72) Inventors: Alexander Russell Abela, Escondido, CA (US); Sunny Abraham, San Diego, CA (US); Corey Don Anderson, Brighton, MA (US); Vijayalaksmi Arumugam, San Marcos, CA (US); Jaclyn Chau, San Diego, CA (US); Jeremy Clemens, San Diego, CA (US); Thomas Cleveland, San Marcos, CA (US); Timothy A Dwight, Quincy, MA (US); Bryan A. Frieman, La Jolla, CA (US); Peter Grootenhuis, Del Mar, CA (US); Sara Sabina Hadida Ruah, La Jolla, CA (US); Yoshihiro Ishihara, San Diego, CA (US); Paul Krenitsky, San Francisco, CA (US); Jason McCartney, Cardiff by the Sea, CA (US); Vito Melillo, Escondido, CA (US); Mark Thomas Miller, Rancho Santa Fe, CA (US); Alina Silina, Needham, MA (US); Johnny Uy, San Diego, CA (US); Jinglan Zhou, San Diego, CA (US)

(73) Assignee: Vertex Pharmaceuticals Incorporated, Boston, MA (US)

( * ) Notice: Subject to any disclaimer, the term of this patent is extended or adjusted under 35 U.S.C. 154(b) by 1025 days.

(21) Appl. No.: 17/600,829

(22) PCT Filed: Apr. 2, 2020

(86) PCT No.: PCT/US2020/026331
§ 371 (c)(1),
(2) Date: Oct. 1, 2021

(87) PCT Pub. No.: WO2020/206080
PCT Pub. Date: Oct. 8, 2020

(65) Prior Publication Data
US 2022/0372047 A1 Nov. 24, 2022

Related U.S. Application Data

(60) Provisional application No. 62/828,699, filed on Apr. 3, 2019.

(51) Int. Cl.
*C07D 515/08* (2006.01)
*C07D 215/233* (2006.01)
(Continued)

(52) U.S. Cl.
CPC ....... *C07D 515/08* (2013.01); *C07D 215/233* (2013.01); *C07D 239/69* (2013.01); *C07D 405/12* (2013.01); *C07B 2200/05* (2013.01)

(58) Field of Classification Search
CPC .............. C07D 515/08; C07D 215/233; C07D 239/69; C07D 405/12; C07B 2200/05
(Continued)

(56) References Cited

U.S. PATENT DOCUMENTS

| 2,677,682 A | 5/1954 | Fahrenbach et al. |
| 7,332,612 B2 | 2/2008 | Dolitzky et al. |

(Continued)

FOREIGN PATENT DOCUMENTS

| CL | 201902734 | 1/2020 |
| CL | 20200856 | 8/2020 |

(Continued)

OTHER PUBLICATIONS

Anonymous: "Symdeko in Cystic Fibrosis Patients", ClinicalTrials.gov, Jul. 23, 2018 (Apr. 23, 2018), XP055661778, Retrieved from the Internet: URL:https://clinicaltrials.gov/ct2/show/record/NCT03506061 [retrieved on Jan. 24, 2020].
(Continued)

*Primary Examiner* — Jeffrey H Murray
*Assistant Examiner* — Grace Ching Hsu
(74) *Attorney, Agent, or Firm* — Finnegan, Henderson, Farabow, Garrett & Dunner, LLP

(57) ABSTRACT

Compound (I), deuterated derivatives, and pharmaceutically acceptable salts of any of the foregoing are disclosed. Methods of treating cystic fibrosis using these compounds are also disclosed.

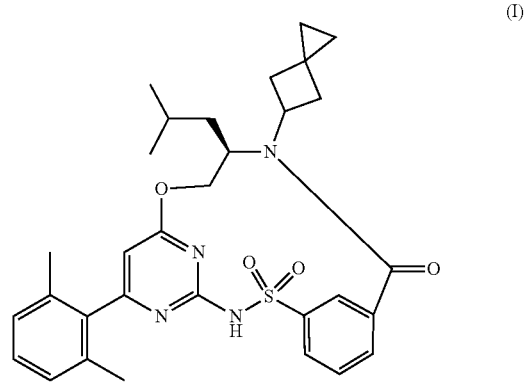

(I)

25 Claims, No Drawings

(51) Int. Cl.
 *C07D 239/69* (2006.01)
 *C07D 405/12* (2006.01)
(58) Field of Classification Search
 USPC .................................................. 514/514, 267
 See application file for complete search history.

(56) References Cited

U.S. PATENT DOCUMENTS

| | | |
|---|---|---|
| 8,586,615 B2 | 11/2013 | Hadida-Ruah et al. |
| 8,865,902 B2 | 10/2014 | Morgan |
| 9,181,192 B2 | 11/2015 | Morgan |
| 9,512,079 B2 | 12/2016 | Morgan |
| 9,663,508 B2 | 5/2017 | Bregman et al. |
| 9,782,408 B2 | 10/2017 | Miller et al. |
| 9,981,910 B2 | 5/2018 | Altenbach et al. |
| 10,047,053 B2 | 8/2018 | Morgan |
| 10,118,916 B2 | 11/2018 | Altenbach et al. |
| 10,131,670 B2 | 11/2018 | Strohbach et al. |
| 10,138,227 B2 | 11/2018 | Altenbach et al. |
| 10,208,053 B2 | 2/2019 | Strohbach et al. |
| 10,258,624 B2 | 4/2019 | Miller et al. |
| 10,479,766 B2 | 11/2019 | Morgan |
| 10,570,115 B2 | 2/2020 | Alcacio et al. |
| 10,654,829 B2 | 5/2020 | Dhamankar et al. |
| 10,675,277 B2 | 6/2020 | Kárpáti et al. |
| 10,738,030 B2 | 8/2020 | Bear et al. |
| 10,758,534 B2 | 9/2020 | Miller et al. |
| 10,759,721 B2 | 9/2020 | Morgan et al. |
| 10,793,547 B2 | 10/2020 | Abela et al. |
| 10,894,773 B2 | 1/2021 | Morgan |
| 11,066,417 B2 | 7/2021 | Clemens et al. |
| 11,179,367 B2 | 11/2021 | Chu et al. |
| 11,584,761 B2 | 2/2023 | Angell et al. |
| 11,591,350 B2 | 2/2023 | Anderson et al. |
| 11,708,331 B2 | 7/2023 | Lemercier Lewandowski et al. |
| 11,866,450 B2 | 1/2024 | Clemens et al. |
| 11,873,300 B2 | 1/2024 | Shi et al. |
| 12,186,306 B2 | 1/2025 | Borek et al. |
| 2011/0098311 A1 | 4/2011 | Van Goor et al. |
| 2013/0317000 A1 | 11/2013 | Chowdhury et al. |
| 2013/0317001 A1 | 11/2013 | Andrez et al. |
| 2014/0073667 A1 | 3/2014 | Morgan et al. |
| 2018/0099932 A1 | 4/2018 | Altenbach et al. |
| 2018/0141954 A1 | 5/2018 | Strohbach et al. |
| 2018/0162839 A1 | 6/2018 | Abela et al. |
| 2018/0170938 A1 | 6/2018 | Strohbach et al. |
| 2018/0244640 A1 | 8/2018 | Altenbach et al. |
| 2019/0055220 A1 | 2/2019 | Bear et al. |
| 2019/0077784 A1 | 3/2019 | Altenbach et al. |
| 2019/0119253 A1 | 4/2019 | Dhamankar et al. |
| 2019/0153000 A1 | 5/2019 | Munoz et al. |
| 2019/0240197 A1 | 8/2019 | Chu et al. |
| 2019/0248809 A1 | 8/2019 | Clemens et al. |
| 2019/0269683 A1 | 9/2019 | Miller et al. |
| 2022/0041621 A1 | 2/2022 | Clemens et al. |
| 2022/0047564 A1 | 2/2022 | Altshuler et al. |
| 2022/0106331 A1 | 4/2022 | Clemens et al. |
| 2022/0127247 A1 | 4/2022 | Azimioara et al. |
| 2022/0184049 A1 | 6/2022 | Borek et al. |
| 2022/0313698 A1 | 10/2022 | Abela et al. |
| 2022/0372047 A1 | 11/2022 | Abela et al. |
| 2023/0374038 A1* | 11/2023 | McCartney et al. |
| 2023/0382925 A1* | 11/2023 | McCartney et al. |

FOREIGN PATENT DOCUMENTS

| | | |
|---|---|---|
| CL | 202301016 | 6/2023 |
| CN | 102227424 A | 10/2011 |
| CN | 103833630 | 6/2014 |
| CN | 106432213 A | 2/2017 |
| EC | SP19028690 | 4/2019 |
| EC | SP19048759 | 7/2019 |
| EC | SP20003147 | 2/2020 |
| EC | SP20053845 | 9/2020 |
| EP | 0 846 687 A1 | 6/1998 |
| JP | 2014-526500 A | 10/2014 |
| JP | 2020-541909 A | 5/2021 |
| JP | 6896619 | 6/2021 |
| JP | 6916285 | 7/2021 |
| JP | 7061115 | 4/2022 |
| TW | I410423 B | 10/2013 |
| TW | 201713617 A | 4/2017 |
| TW | 201811766 A | 1/2018 |
| WO | WO 2001/090092 A1 | 11/2001 |
| WO | WO 2005/049018 A1 | 6/2005 |
| WO | WO 2005/075435 A1 | 8/2005 |
| WO | WO 2006/002421 A2 | 1/2006 |
| WO | WO 2007/021982 A2 | 2/2007 |
| WO | WO 2007/053641 A2 | 5/2007 |
| WO | WO 2007/075946 A1 | 7/2007 |
| WO | WO 2007/079139 A2 | 7/2007 |
| WO | WO 2007/087066 A2 | 8/2007 |
| WO | WO 2007/117715 A2 | 10/2007 |
| WO | WO 2007/134279 A2 | 11/2007 |
| WO | WO 2008/127399 A2 | 10/2008 |
| WO | WO 2008/154241 A1 | 12/2008 |
| WO | WO 2009/006315 A1 | 1/2009 |
| WO | WO 2009/038683 A2 | 3/2009 |
| WO | WO 2009/073757 A1 | 6/2009 |
| WO | WO 2009/076142 A2 | 6/2009 |
| WO | WO 2009/108657 A2 | 9/2009 |
| WO | WO 2010/019239 A2 | 2/2010 |
| WO | WO 2010/048526 A2 | 4/2010 |
| WO | WO 2010/053471 A1 | 5/2010 |
| WO | WO 2010/054138 A2 | 5/2010 |
| WO | WO 2010/108162 A1 | 9/2010 |
| WO | WO 2011/019413 A1 | 2/2011 |
| WO | WO 2011/029059 A1 | 3/2011 |
| WO | WO 2011/072241 A1 | 6/2011 |
| WO | WO 2011/116397 A1 | 9/2011 |
| WO | WO 2011/119984 A1 | 9/2011 |
| WO | WO 2011/127241 A2 | 10/2011 |
| WO | WO 2011/127290 A2 | 10/2011 |
| WO | WO 2011/133751 A2 | 10/2011 |
| WO | WO 2011/133951 A1 | 10/2011 |
| WO | WO 2012/027247 A2 | 3/2012 |
| WO | WO 2012/027731 A2 | 3/2012 |
| WO | WO 2012/158885 A1 | 11/2012 |
| WO | WO 2012/170061 A1 | 12/2012 |
| WO | WO 2013/038386 A1 | 3/2013 |
| WO | WO 2013/064984 A1 | 5/2013 |
| WO | WO 2013/070961 A1 | 5/2013 |
| WO | WO 2013/112804 A1 | 8/2013 |
| WO | WO 2013/130669 A1 | 9/2013 |
| WO | WO 2013/158121 A1 | 10/2013 |
| WO | WO 2013/160419 A1 | 10/2013 |
| WO | WO 2013/185112 A1 | 12/2013 |
| WO | WO 2014/014841 A1 | 1/2014 |
| WO | WO 2014/071122 A1 | 5/2014 |
| WO | WO 2014/078842 A1 | 5/2014 |
| WO | WO 2015/073231 A1 | 7/2015 |
| WO | WO 2015/160787 A1 | 10/2015 |
| WO | WO 2016/057730 A1 | 2/2016 |
| WO | WO 2016/057572 A1 | 4/2016 |
| WO | WO 2016/081556 A1 | 5/2016 |
| WO | WO 2016/160945 A1 | 10/2016 |
| WO | WO 2017/009804 A1 | 1/2017 |
| WO | WO 2017/053455 A1 | 3/2017 |
| WO | WO 2017/053711 A2 | 3/2017 |
| WO | WO 2017/172802 A1 | 10/2017 |
| WO | WO 2017/173274 A1 | 10/2017 |
| WO | WO 2017/177124 A1 | 10/2017 |
| WO | WO 2017/187321 A1 | 11/2017 |
| WO | WO 2017/208115 A1 | 12/2017 |
| WO | WO 2017/223188 A1 | 12/2017 |
| WO | WO 2018/064632 A1 | 4/2018 |
| WO | WO 2018/080591 A1 | 5/2018 |
| WO | WO 2018/081377 A1 | 5/2018 |
| WO | WO 2018/081378 A1 | 5/2018 |
| WO | WO 2018/081381 A1 | 5/2018 |
| WO | WO 2018/107100 A1 | 6/2018 |
| WO | WO 2018/116185 A1 | 6/2018 |
| WO | WO 2018/127130 A1 | 7/2018 |

(56) References Cited

FOREIGN PATENT DOCUMENTS

| | | |
|---|---|---|
| WO | WO 2018/183367 A1 | 10/2018 |
| WO | WO 2018/183964 A1 | 10/2018 |
| WO | WO 2018/201126 A1 | 11/2018 |
| WO | WO 2018/227049 A1 | 12/2018 |
| WO | WO 2019/010092 A1 | 1/2019 |
| WO | WO 2019/014352 A1 | 1/2019 |
| WO | WO 2019/018353 A1 | 1/2019 |
| WO | WO 2019/018395 A1 | 1/2019 |
| WO | WO 2019/028228 A1 | 2/2019 |
| WO | WO 2019/071078 A1 | 4/2019 |
| WO | WO 2019/079760 A1 | 4/2019 |
| WO | WO 2019/109021 A1 | 6/2019 |
| WO | WO 2019/113089 A1 | 6/2019 |
| WO | WO 2019/113476 A1 | 6/2019 |
| WO | WO 2019/152940 A1 | 8/2019 |
| WO | WO 2019/161078 A1 | 8/2019 |
| WO | WO 2019/026075 A1 | 10/2019 |
| WO | WO 2019/191620 A1 | 10/2019 |
| WO | WO 2019/200246 A1 | 10/2019 |
| WO | WO 2020/102346 A1 | 5/2020 |
| WO | WO 2020/128925 A1 | 6/2020 |
| WO | WO 2020/191227 A1 | 9/2020 |
| WO | WO 2020/206080 A1 | 10/2020 |
| WO | WO 2020/214921 A1 | 10/2020 |
| WO | WO 2020/242935 A1 | 12/2020 |
| WO | WO 2021/030552 A1 | 2/2021 |
| WO | WO 2021/030554 A1 | 2/2021 |
| WO | WO 2021/030555 A1 | 2/2021 |
| WO | WO 2021/030556 A1 | 2/2021 |
| WO | WO 2021/097054 A1 | 5/2021 |
| WO | WO 2021/097057 A1 | 5/2021 |
| WO | WO 2022/032068 A1 | 2/2022 |
| WO | WO 2022/036060 A1 | 2/2022 |
| WO | WO 2022/076620 A2 | 4/2022 |
| WO | WO 2022/076621 A2 | 4/2022 |
| WO | WO 2022/076622 A2 | 4/2022 |
| WO | WO 2022/076624 A2 | 4/2022 |
| WO | WO 2022/076625 A2 | 4/2022 |
| WO | WO 2022/076626 A2 | 4/2022 |

OTHER PUBLICATIONS

Donaldson, S.H. et al. (2017) "Tezacaftor/Ivacaftor in Subjects with Cystic Fibrosis and F508del/F508del-CFTR or F508del/G551D-CFTR", Am. J. Respir. Crit. Care Med., 197(2): 214-224.
International Patent Application No. PCT/US2019/018042: International Search Report and Written Opinion, mailed Apr. 17, 2019 (10 pages).
International Patent Application No. PCT/US2019/061171: International Search Report and Written Opinion, mailed Feb. 2, 2020 (14 pages).
International Patent Application No. PCT/U2020/026331: International Search Report and Written Opinion, mailed May 29, 2020 (14 pages).
U.S. Appl. No. 17/323,267, filed May 18, 2021, by Clemens et al.
U.S. Appl. No. 17/293,632, filed May 13, 2021, by Altshuler et al.
U.S. Appl. No. 16/992,419, filed Aug. 13, 2021, by Angell et al.
U.S. Appl. No. 16/992,441, filed Aug. 13, 2021, by Shi et al.
U.S. Appl. No. 16/992,448, filed Aug. 13, 2021, by Anderson et al.
U.S. Appl. No. 16/992,675, filed Aug. 13, 2021, by Abela et al.
U.S. Appl. No. 17/546,649, filed Dec. 9, 2021, by Borek et al.
Alberti, C. and Tironi, C. (1964) "Sulfanilammidi Pirazoliche, VI. 1-(Tolil)-sulfanilamidopirazoli derivati dal 3-aminopirazolo, dal 4-aminopirazolo e dal 3-metil-5-aminopirazolo," Il Farmaco—Ed. Sc. 29(7), 618-637.
Alberti, C. and Tironi, C. (1971) "Sulfanilammidi Pirazoliche," Il Farmaco—Ed. Sc. 26(1), 66-88.
Bastin, R.J. et al., "Salt selection and optimization procedures for pharmaceutical new chemical entities," Org. Pro. Res. Dev. 2000, 4(5), 427-435.
Braker, W. et al. (1947) "Substituted Sulfanilamidopyrimidines," J. Am. Chem. Society, 69, 3072-3075.

Chen, L. et al. (2014) "Synthesis and Antimicrobial Activity of the Hybrid Molecules between Sulfonamides and Active Antimicrobial Pleuromutilin Derivative," Chemical Biology and Drug Design, 86(2), 239-245.
Cherepakha, A.Y. et al. (2018) "Hetaryl Bromides Bearing the SO2F Group—Versatile Substrates for Palladium-Catalyzed C—C Coupling Reactions", Eur J Org Chem, 47: 6682-6692.
Chio, L. et al. (1996) "Identification of a Class of Sulfonamides Highly Active Against Dihydropteroate Synthase from Toxoplasma Gondii, Pneumocystis Carinii, and Mycobacterium avium," Antimicrobial Agents and Chemotherapy, American Society for Microbiology, 40(3), 727-733.
Gage, J. C. et al. (1947), "2-P-Aminobenzenesulphonamido-4 : 6-Dimethoxypyrimidine: Experimental Evaluation," British Journal of Pharmacology and Chemotherapy, 2(3), 149-162.
Ghorab, Mostafa at al. (2017) "Aromatase inhibitors and apoptotic inducers: Design, synthesis, anticancer activity and molecular modeling studies of novel phenothiazine derivatives carrying sulfonamide moiety as hybrid molecules," Eur. J. Med. Chem., 134, 304-315.
Gomes, Paula et al. (2003) "Amino acids as selective sulfonamide acylating agents," Tetrahedron, 59(38), 7473-7480.
Hassan, H. H. A. M. and Soliman, R. (2000) "Synthesis and GC-EIMS Analyses of Optically Pure 3-Hydroxy-2-azetidinones Having N-sulfonamide Drugs Side Chain," Synthetic Communications, 30(14), 2465-2478.
International Patent Application No. PCT/US2021/053853: International Search Report and Written Opinion, mailed Dec. 21, 2021 (12 pages).
International Patent Application No. PCT/US2021/053855: International Search Report and Written Opinion, mailed Jan. 3, 2022 (12 pages).
International Patent Application No. PCT/US2021/053856: International Search Report and Written Opinion, mailed Dec. 22, 2021 (12 pages).
International Patent Application No. PCT/US2021/053858: International Search Report and Written Opinion, mailed Mar. 17, 2022 (14 pages).
International Patent Application No. PCT/US2021/053860: International Search Report and Written Opinion, mailed Dec. 23, 2021 (12 pages).
International Patent Application No. PCT/US2021/053861: International Search Report and Written Opinion, mailed Dec. 22, 2021 (12 pages).
International Patent Application No. PCT/US2021/053862: International Search Report and Written Opinion, mailed Dec. 22, 2021 (12 pages).
International Patent Application No. PCT/US2021/053863: International Search Report and Written Opinion, mailed Feb. 4, 2022 (16 pages).
International Patent Application No. PCT/US2021/053864: International Search Report and Written Opinion, mailed Mar. 15, 2022 (17 pages).
International Patent Application No. PCT/US2021/053865: International Search Report and Written Opinion, mailed Jan. 26, 2022 (16 pages).
International Patent Application No. PCT/US2021/062687: International Search Report and Written Opinion, mailed Apr. 4, 2022 (14 pages).
Kim, T. et al. (2018) "Sulfonamidation of Aryl and Heteroaryl Halides through Photosensitized Nickel Catalysis," Agewandte Chemie, 57, 3488-3492.
Newkome, G.R. et al. (1979) "Nicotinic Acid Crown Ethers. Synthesis, Reactions, and Complexation of Nicotinonitrile Macrocycles", J Org Chem, 44(15): 2639-2697.
Nishida, H. et al. (2017) "Exploration of pyrrole derivatives to find an effective potassium competitive acid blocker with moderately long-lasting suppression of gastric acid secretion", Bioorg Med Chem, 25(13): 3447-3460.
"A phase 1/2 study of VX-121 in healthy subjects and in subjects with cystic fibrosis", EU Clinical Trials Register, May 3, 2019 (May 3, 2019), XP055903414, Retrieved from the Internet: URL:https://www.clinicaltrialsregister.eu/ctr-search/trial/2018-000126-55/NL [retrieved on Mar. 21, 2022].

(56) References Cited

OTHER PUBLICATIONS

"A Phase 2 Study to Evaluate Efficacy and Safety of VX-561 in Subjects Aged 18 Years and Older With Cystic Fibrosis", ClinicatTials.gov, Apr. 11, 2019 (Apr. 11, 2019), XP055903562, Retrieved from the Internet: URL:https://clinicaltrials.gov/ct2/show/NCT03911713 [retrieved on Mar. 21, 2022].

Prashantha, G. et al. (2017) "Selective IKur Inhibitors for the Potential Treatment of Atrial Fibrillation: Optimization of the Phenyl Quinazoline Series Leading to Clinical Candidate 5-[5-Phenyl-4-(pyridin-2-ylmethylamino)quinazolin-2-yl]pyridine-3-sulfonamide", J Med Chem, 60(9): 3795-3803.

Rewcastle, G.W. et al. (1996) "Tyrosine Kinase Inhibitors. 10. Isomeric 4-[(3-Bromophenyl)amino]pyrido[d]-pyrimidines Are Potent ATP Binding Site Inhibitors of the Tyrosine Kinase Function of the Epidermal Growth Factor Receptor", J Med Chem, 39(9): 1823-1835.

Raiziss, GW et al. (1942) "N1-Sulfanilylaminoalkylpyrimidines," J. Am. Chem. Soc. 64, 2340-2342.

Rose, F. L. et al. (1946) "P-Aminobenzenesulphonamide Derivatives of Pyrimidines as Antibacterial Agents," J. Am. Chem. Soc., 81-85.

Sprague, JM et al. (1941) "Sulfonamido derivatives of thiazoles," J. Am. Chem. Soc. 63, 578-580.

Sprague, JM et al. (1941) "Sulfonamido derivatives of pyrimidines," J. Am. Chem. Soc. 63, 3028-3030.

"A Study to Evaluate the Safety and Efficacy of VX-121 Combination Therapy in Subjects with Cystic Fibrosis", ClinicalTrials.gov, Apr. 30, 2019 (Apr. 30, 2019), XP55903330, Retrieved from the Internet: URL:https://clinicaltrials.gov/ct2/show/NCT03912233 [retrieved on Mar. 21, 2022].

Sugasawa, S et al. (1949) "Reaction between sulfaguanidine and 1,3-keto aldehydes. I. Synthesis of 2-sulfanilamido-4-methylpyrimidine," 69, 82-85.

Tani, C et al. (1950) "Syntheses of sulfanilamide derivatives containing diphenylene oxide," Journal of the Pharmaceutical Society of Japan, 70, 126-127.

U.S. Appl. No. 17/600,829, filed Oct. 1, 2021, by Abela et al.

Borhade, Sanjay R., et al., "Synthesis of Novel Aryl and Heteroaryl Acyl Sulfonimidamides via Pd-Catalyzed Carbonylation Using a Nongaseous Precursor," Organic Letters, 2013, vol. 15, No. 5, pp. 1056-1059, received Jan. 8, 2013, XP055374206A, © 2013 American Chemical Society, ISSN: 1523-7060, DOI:10.1021/ol4/00049m, published on web Feb. 13, 2013.

International Patent Application No. PCT/US2021/045691: International Search Report and Written Opinion, mailed Dec. 13, 2021 (16 pages).

Davies, J.C. et al. (2018), "VX-659-Tezacaftor-Ivacaftor in Patients with Cystic Fibrosis and One or Two Phe508del Alleles," The New England Journal of Medicine, 379, 17, pp. 1599-1611.

Harbeson, Scott L., et al. "Altering Metabolic Profiles of Drugs by Precision Deuteration 2: Discovery of a Deuterated Analog of Ivacaftor with Differentiated Pharmacokinetics for Clinical Development." The Journal of Pharmacology and Experimental Therapeutics, 2017, 362, 2, pp. 359-367.

International Patent Application No. PCT/US2023/017627: International Search Report and Written Opinion, mailed Jul. 7, 2023 (14 pages).

Keating, D. et al. (2018), "VX-445-Tezacaftor-Ivacaftor in Patients with Cystic Fibrosis and One or Two Phe508del Alleles," The New England Journal of Medicine, 379, 17, pp. 1612-1620.

Morissette et al., "High-throughput crystallization: polymorphs, salts, co-crystals and solvates of pharmaceutical solids," Advanced Drug Delivery Reviews, 2004, 56, pp. 275-300.

Notice of Allowance and Fee(s) Due for U.S. Appl. No. 18/493,667, mailed Jan. 23, 2025, (7 pages).

Taylor-Cousar, Jennifer L. Taylor-Cousar, et al. "Tezacaftor-Ivacaftor in Patients with Cystic Fibrosis Homozygous for Phe508del". The New England Journal of Medicine, 2017, 377, 21, pp. 2013-2023.

Wang, Xuequing, et al. "Discovery of 4-[(2R,4R)-4-({1-(2,2-Difluoro-1,3-benzodioxol-5-yl)cyclopropyl}carbonyl)amino]-7-(difluoromethoxy)-3,4-dihydro-2H-chromen-2-yl)benzoic Acid (ABBV/GLPG-2222), a Potent Cystic Fibrosis Transmembrane Conductance Regulator (CFTR) Corrector for the Treatment of Cystic Fibrosis." Journal of Medicinal Chemistry, 2018, 61, pp. 1436-1449.

* cited by examiner

CYSTIC FIBROSIS TRANSMEMBRANE CONDUCTANCE REGULATOR MODULATING AGENTS

This application is a national stage application under 35 U.S.C. § 371 of international application number PCT/US2020/026331, filed Apr. 2, 2020, which designated the U.S. and claims the benefit of U.S. Provisional Application No. 62/828,699, filed on Apr. 3, 2019, the contents of both of which are incorporated by reference in their entirety.

The disclosure provides modulators of Cystic Fibrosis Transmembrane Conductance Regulator (CFTR), pharmaceutical compositions containing the modulators, methods of treating cystic fibrosis (CF) and CFTR-mediated disorders comprising administering the modulators, and processes for making the modulators.

CF is a recessive genetic disease that affects approximately 70,000 children and adults worldwide. Despite progress in the treatment of CF, there is no cure.

In patients with CF, mutations in CFTR endogenously expressed in respiratory epithelia lead to reduced apical anion secretion, causing an imbalance in ion and fluid transport. The resulting decrease in anion transport contributes to enhanced mucus accumulation in the lung and accompanying microbial infections that ultimately cause death in CF patients. In addition to respiratory disease, CF patients typically suffer from gastrointestinal problems and pancreatic insufficiency that, if left untreated, result in death. In addition, the majority of males with CF are infertile, and fertility is reduced among females with CF.

Sequence analysis of the CFTR gene has revealed a variety of disease-causing mutations (Cutting, G. R. et al. (1990) Nature 346:366-369; Dean, M. et al. (1990) Cell 61:863:870; and Kerem, B-S. et al. (1989) Science 245: 1073-1080; Kerem, B-S et al. (1990) Proc. Natl. Acad. Sci. USA 87:8447-8451). To date, greater than 2000 mutations in the CF gene have been identified. CF mutations are listed in the "Cystic Fibrosis Mutation Database," located at http://www.genet.sickkids.on.ca/app, which is incorporated herein by reference in its entirety. The most prevalent disease-causing mutation is a deletion of phenylalanine at position 508 of the CFTR amino acid sequence and is commonly referred to as the F508del mutation. This mutation occurs in approximately 90% of the cases of cystic fibrosis and is associated with severe disease.

The deletion of residue 508 in CFTR prevents the nascent protein from folding correctly. This results in the inability of the mutant protein to exit the endoplasmic reticulum (ER) and traffic to the plasma membrane. As a result, the number of CFTR channels for anion transport present in the membrane is far less than observed in cells expressing wild-type CFTR, i.e., CFTR having no mutations. In addition to impaired trafficking, the mutation results in defective channel gating. Together, the reduced number of channels in the membrane and the defective gating lead to reduced anion and fluid transport across epithelia. (Quinton, P. M. (1990), FASEB J. 4: 2709-2727). The channels that are defective because of the F508del mutation are still functional, albeit less functional than wild-type CFTR channels. (Dalemans et al. (1991), Nature Lond. 354: 526-528; Pasyk and Foskett (1995), J. Cell. Biochem. 270: 12347-50). In addition to F508del, other disease-causing mutations in CFTR that result in defective trafficking, synthesis, and/or channel gating could be up- or down-regulated to alter anion secretion and modify disease progression and/or severity.

CFTR is a cAMP/ATP-mediated anion channel that is expressed in a variety of cell types, including absorptive and secretory epithelial cells, where it regulates anion flux across the membrane, as well as the activity of other ion channels and proteins. In epithelial cells, normal functioning of CFTR is critical for the maintenance of electrolyte transport throughout the body, including respiratory and digestive tissue. CFTR is composed of approximately 1480 amino acids that encode a protein which is made up of a tandem repeat of transmembrane domains, each containing six transmembrane helices and a nucleotide binding domain. The two transmembrane domains are linked by a large, polar, regulatory (R)-domain with multiple phosphorylation sites that regulate channel activity and cellular trafficking.

Chloride transport takes place by the coordinated activity of ENaC and CFTR present on the apical membrane and the $Na^+$—$K^+$-ATPase pump and $Cl^-$ channels expressed on the basolateral surface of the cell. Secondary active transport of chloride from the luminal side leads to the accumulation of intracellular chloride, which can then passively leave the cell via $Cl^-$ channels, resulting in a vectorial transport. Arrangement of $Na^+/2Cl^-/K^+$ co-transporter, $Na^+$—$K^+$-ATPase pump, and the basolateral membrane $K^+$ channels on the basolateral surface and CFTR on the luminal side coordinate the secretion of chloride via CFTR on the luminal side. Because water is probably never actively transported itself, its flow across epithelia depends on tiny transepithelial osmotic gradients generated by the bulk flow of sodium and chloride.

A number of CFTR modulating compounds have recently been identified. However, compounds that can treat or reduce the severity of the CF and other CFTR-mediated diseases, and particularly the more severe forms of these diseases, are still needed.

Thus, one aspect of the disclosure provides CFTR modulating compound (11R)-6-(2,6-dimethylphenyl)-11-(2-methylpropyl)-12-{spiro[2.3]hexan-5-yl}-9-oxa-2$\lambda^6$-thia-3,5,12,19-tetraazatricyclo[12.3.1.14,8]nonadeca-1(17),4(19),5,7,14(18),15-hexaene-2,2,13-trione (Compound I) and pharmaceutically acceptable salts and deuterated derivatives thereof. Another name for Compound I is (R)-1$^6$-(2,6-dimethylphenyl)-7-isobutyl-6-(spiro[2.3]hexan-5-yl)-9-oxa-3-thia-2,6-diaza-1(2,4)-pyrimidina-4(1,3)-benzenacyclononaphan-5-one 3,3-dioxide. Compound I can be depicted as having the following structure:

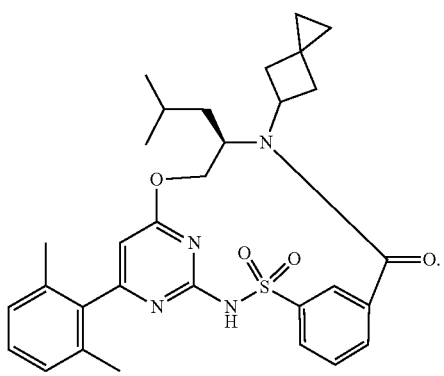

Exemplary deuterated derivatives of Compound I include the following compounds:

Ia
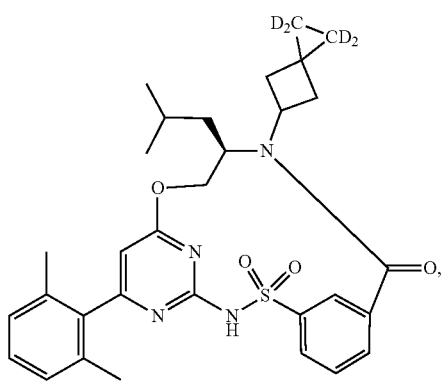

Ib
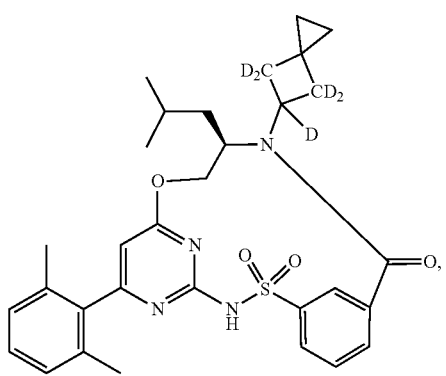

Ic
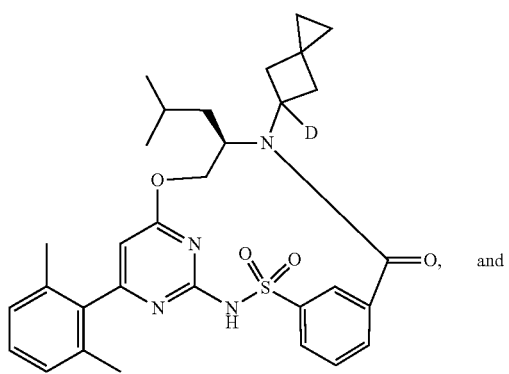

and

Id
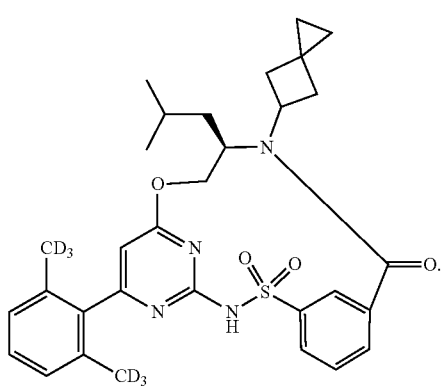

Exemplary salts of Compound I and deuterated derivatives of Compound I include potassium salts, sodium salts, and calcium salts.

The disclosure also provides pharmaceutical compositions comprising at least one of Compound I, deuterated derivatives of Compound I, and pharmaceutically acceptable salts of Compound I or its deuterated derivatives. In some embodiments, the compositions may further include at least one additional active pharmaceutical ingredient and/or at least one carrier. Also disclosed are methods of treating the CFTR-mediated disease CF, comprising administering at least one of Compound I, deuterated derivatives of Compound I, and pharmaceutically acceptable salts of Compound I or its deuterated derivatives. In some embodiments, the method may optionally include administration of one or more additional active pharmaceutical ingredient(s). In some embodiments, the additional active pharmaceutical ingredient(s) is a CFTR modulator. In some embodiments, the CFTR modulator is chosen from CFTR potentiators and CFTR correctors.

The disclosure also provides methods of treating the CFTR-mediated disease CF, comprising administering to a patient in need thereof at least one of Compound I, deuterated derivatives of Compound I, and pharmaceutically acceptable salts of Compound I or its deuterated derivatives, in combination with one or more of compounds selected from (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide (Compound II):

II
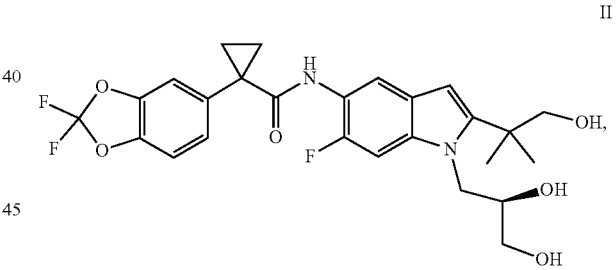

N-[2,4-bis(1,1-dimethylethyl)-5-hydroxyphenyl]-1,4-dihydro-4-oxoquinoline-3-carboxamide (Compound III):

III
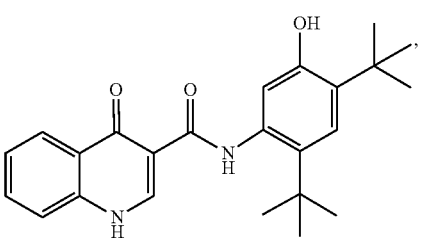

N-(2-(tert-butyl)-5-hydroxy-4-(2-(methyl-d3)propan-2-yl-1,1,1,3,3,3-d6)phenyl)-4-oxo-1,4-dihydroquinoline-3-carboxamide (Compound III-d):

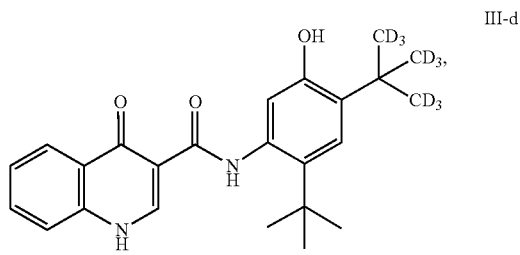 [SMILES: [2H]C([2H])([2H])C(c1cc(C(C)(C)C)c(NC(=O)c2c[nH]c3ccccc3c2=O)cc1O)(C([2H])([2H])[2H])C([2H])([2H])[2H]]

and 3-(6-(1-(2,2-difluorobenzo[d][1,3]dioxol-5-yl)cyclopropanecarboxamido)-3-methylpyridin-2-yl)benzoic acid (Compound IV):

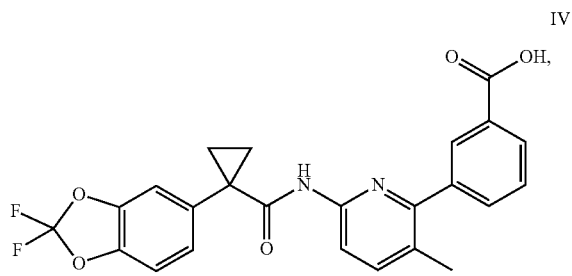 [SMILES: Cc1ccc(NC(=O)C2(c3ccc4c(c3)OC(F)(F)O4)CC2)nc1-c1cccc(C(=O)O)c1]

and pharmaceutically acceptable salts of Compounds II, III, III-d, and IV.

Definitions

As used herein, a "deuterated derivative" of Compound I refers to a compound having the same chemical structure as Compound I, but with one or more hydrogen atoms replaced by a deuterium atom.

As used herein, "mutations" can refer to mutations in the CFTR gene or the CFTR protein. A "CFTR gene mutation" refers to a mutation in the CFTR gene, and a "CFTR protein mutation" refers to a mutation in the CFTR protein. In general, a genetic defect or mutation, or a change in the nucleotides in a gene results in a mutation in the CFTR protein translated from that gene, or a frame shift(s).

The term "F508del" refers to a mutant CFTR protein which is lacking the amino acid phenylalanine at position 508.

As used herein, a patient who is "homozygous" for a particular gene mutation has the same mutation on both alleles.

As used herein, a patient who is "heterozygous" for a particular gene mutation has this mutation on one allele, and a different mutation on the other allele.

As used herein, the term "modulator" refers to a compound that increases the activity of a biological compound such as a protein. For example, a CFTR modulator is a compound that increases the activity of CFTR. The increase in activity resulting from a CFTR modulator includes but is not limited to compounds that correct, potentiate, stabilize and/or amplify CFTR.

As used herein, the term "CFTR corrector" refers to a compound that facilitates the processing and trafficking of CFTR to increase the amount of CFTR at the cell surface. Compounds I, II, and IV, and their pharmaceutically acceptable salts and deuterated derivatives are CFTR correctors.

As used herein, the term "CFTR potentiator" refers to a compound that increases the channel activity of CFTR protein located at the cell surface, resulting in enhanced ion transport. Compound III and III-d are CFTR potentiators.

As used herein, the term "active pharmaceutical ingredient" or "API" refers to a biologically active compound.

As used herein, the term "pharmaceutically acceptable salt" refers to a salt form of a compound of this disclosure wherein the salt is nontoxic. Pharmaceutically acceptable salts of the compounds of this disclosure include those derived from suitable inorganic and organic acids and bases. Pharmaceutically acceptable salts are well known in the art. For example, S. M. Berge, et al. describe pharmaceutically acceptable salts in detail in *J. Pharm. Sci.*, 1977, 66, 1-19.

Suitable pharmaceutically acceptable salts are, for example, those disclosed in S. M. Berge, et al. *J. Pharm. Sci.*, 1977, 66, 1-19. For example, Table 1 of that article provides the following pharmaceutically acceptable salts:

TABLE 1

| Pharmaceutically Acceptable Salts | | |
|---|---|---|
| Acetate | Iodide | Benzathine |
| Benzenesulfonate | Isethionate | Chloroprocaine |
| Benzoate | Lactate | Choline |
| Bicarbonate | Lactobionate | Diethanolamine |
| Bitartrate | Malate | Ethylenediamine |
| Bromide | Maleate | Meglumine |
| Calcium edetate | Mandelate | Procaine |
| Camsylate | Mesylate | Aluminum |
| Carbonate | Methylbromide | Calcium |
| Chloride | Methylnitrate | Lithium |
| Citrate | Methylsulfate | Magnesium |
| Dihydrochloride | Mucate | Potassium |
| Edetate | Napsylate | Sodium |
| Edisylate | Nitrate | Zinc |
| Estolate | Pamoate (Embonate) | |
| Esylate | Pantothenate | |
| Fumarate | Phosphate/diphosphate | |
| Gluceptate | Polygalacturonate | |
| Gluconate | Salicylate | |
| Glutamate | Stearate | |
| Glycollylarsanilate | Subacetate | |
| Hexylresorcinate | Succinate | |
| Hydrabamine | Sulfate | |
| Hydrobromide | Tannate | |
| Hydrochloride | Tartrate | |
| Hydroxynaphthoate | Teociate | |
| | Triethiodide | |

Non-limiting examples of pharmaceutically acceptable salts derived from appropriate acids include: salts formed with inorganic acids, such as hydrochloric acid, hydrobromic acid, phosphoric acid, sulfuric acid, or perchloric acid; salts formed with organic acids, such as acetic acid, oxalic acid, maleic acid, tartaric acid, citric acid, succinic acid, or malonic acid; and salts formed by using other methods used in the art, such as ion exchange. Non-limiting examples of pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, and valerate salts. Non-limiting examples of pharmaceutically acceptable salts derived from appropriate bases include alkali metal, alkaline earth metal, ammonium, and $N^+(C_{1-4}alkyl)_4$ salts. This disclosure also envisions the quaternization of any basic nitrogen-containing groups of the compounds disclosed herein. Suitable non-limiting examples of alkali and alkaline earth metal salts include sodium, lithium, potassium, calcium, and magnesium. Further non-limiting examples of pharmaceutically acceptable salts include ammonium, quaternary ammonium, and amine cations formed using counterions such as halide, hydroxide, carboxylate, sulfate, phosphate, nitrate, lower alkyl sulfonate, and aryl sulfonate. Other suitable, non-limiting examples of pharmaceutically acceptable salts include besylate and glucosamine salts.

As used herein, the term "amorphous" refers to a solid material having no long-range order in the position of its molecules. Amorphous solids are generally supercooled liquids in which the molecules are arranged in a random manner so that there is no well-defined arrangement, e.g., molecular packing, and no long-range order. Amorphous solids are generally isotropic, i.e. exhibit similar properties in all directions and do not have definite melting points. For example, an amorphous material is a solid material having no sharp characteristic crystalline peak(s) in its X-ray power diffraction (XRPD) pattern (i.e., is not crystalline as determined by XRPD). Instead, one or several broad peaks (e.g., halos) appear in its XRPD pattern. Broad peaks are characteristic of an amorphous solid. See, US 2004/0006237 for a comparison of XRPDs of an amorphous material and crystalline material.

The terms "patient" and "subject" are used interchangeably and refer to an animal, including humans.

The terms "effective dose" and "effective amount" are used interchangeably herein and refer to that amount of a compound that produces the desired effect for which it is administered (e.g., improvement in CF or a symptom of CF, or lessening the severity of CF or a symptom of CF). The exact amount of an effective dose will depend on the purpose of the treatment, and will be ascertainable by one skilled in the art using known techniques (see, e.g., Lloyd (1999) The Art, Science and Technology of Pharmaceutical Compounding).

As used herein, the terms "treatment," "treating," and the like generally mean the improvement of CF or its symptoms or lessening the severity of CF or its symptoms, or a delay in the onset of CF or its symptoms, in a subject. "Treatment," as used herein, includes, but is not limited to, the following: increased growth of the subject, increased weight gain, reduction of mucus in the lungs, improved pancreatic and/or liver function, reduction of chest infections, and/or reductions in coughing or shortness of breath. Improvements in or lessening the severity of any of these symptoms can be readily assessed according to standard methods and techniques known in the art.

As used herein, the term "in combination with," when referring to two or more compounds, agents, or additional active pharmaceutical ingredients, means the administration of two or more compounds, agents, or active pharmaceutical ingredients to the patient prior to, concurrent with, or subsequent to each other. In some embodiments, the methods of the disclosure employ administering to a patient in need thereof at least one compound chosen from Compound I, deuterated derivatives of Compound I, and pharmaceutically acceptable salts of Compound I or its deuterated derivatives, and may optionally employ administration of at least one compound selected from:

Compound II

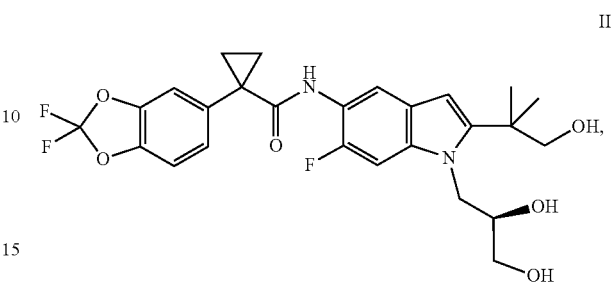

Compound III

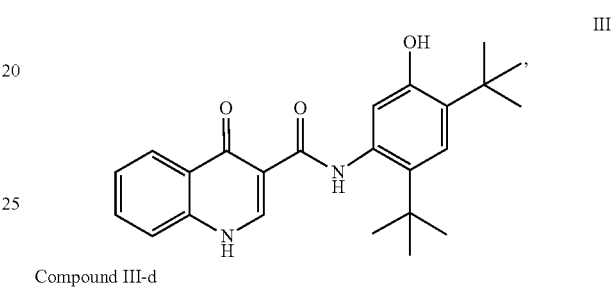

Compound III-d

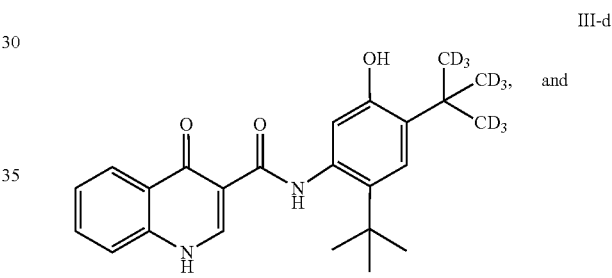

Compound IV

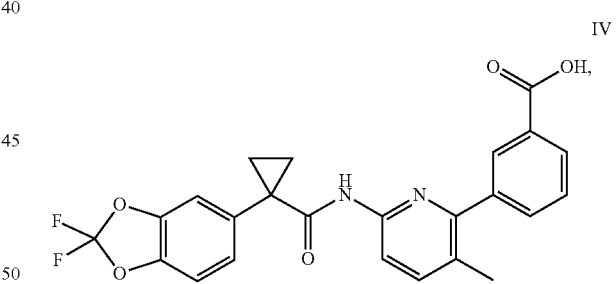

and pharmaceutically acceptable salts of Compounds II, III, III-d, and IV.

Compound I, deuterated derivatives of Compound I, and pharmaceutically acceptable salts of Compound I or its deuterated derivatives can be independently administered once daily, twice daily, or three times daily, optionally in combination with one or more of Compounds II, III, III-d, and IV, and pharmaceutically acceptable salts and deuterated derivatives thereof. In some embodiments, at least one compound chosen from Compound I, deuterated derivatives of Compound I, and pharmaceutically acceptable salts of Compound I or its deuterated derivatives, is administered once daily. In some embodiments, at least one compound chosen from Compound I, deuterated derivatives of Compound I, and pharmaceutically acceptable salts of Compound I or its deuterated derivatives, is administered twice daily, optionally in combination with one or more of Compounds II, III, III-d, IV, and pharmaceutically acceptable salts and deuterated derivatives thereof.

One of ordinary skill in the art would recognize that, when an amount of "a compound or a pharmaceutically acceptable salt thereof" is disclosed, the amount of the pharmaceutically acceptable salt form of the compound is the amount equivalent to the concentration of the free base of the compound. It is noted that the disclosed amounts of the compounds or their pharmaceutically acceptable salts thereof herein are based upon their free base form. For example, "10 mg of at least one compound chosen from Compound I and pharmaceutically acceptable salts thereof" includes 10 mg of Compound I and a concentration of a pharmaceutically acceptable salt of Compound I equivalent to 10 mg of Compound I.

In some embodiments, at least one compound chosen from Compound I, deuterated derivatives of Compound I, and pharmaceutically acceptable salts of Compound I or its deuterated derivatives, is administered in combination with at least one compound chosen from Compound II, deuterated derivatives of Compound II, or pharmaceutically acceptable salts of Compound II or its deuterated derivatives.

In some embodiments, at least one compound chosen from Compound I, deuterated derivatives of Compound I, and pharmaceutically acceptable salts of Compound I or its deuterated derivatives, is administered in combination with at least one compound chosen from Compound III, deuterated derivatives of Compound III, and pharmaceutically acceptable salts of Compound III or its deuterated derivatives. In some embodiments, the deuterated derivative of Compound III is Compound III-d.

In some embodiments, at least one compound chosen from Compound I, deuterated derivatives of Compound I, and pharmaceutically acceptable salts of Compound I or its deuterated derivatives, is administered in combination with at least one compound chosen from Compound IV deuterated derivatives of Compound IV, and pharmaceutically acceptable salts of Compound IV or its deuterated derivatives.

In some embodiments, at least one compound chosen from Compound I, deuterated derivatives of Compound I, and pharmaceutically acceptable salts of Compound I or its deuterated derivatives, is administered in combination with Compounds II or a pharmaceutically acceptable salt or deuterated derivative thereof and at least one compound chosen from Compound III, deuterated derivatives Compound III, or pharmaceutically acceptable salts thereof. In some embodiments, the deuterated derivative of Compound III is Compound III-d.

In some embodiments, at least one compound chosen from Compound I, and pharmaceutically acceptable salts of Compound I or its deuterated derivatives, is administered in combination with at least one compound chosen from Compound III, deuterated derivatives of Compound III, and pharmaceutically acceptable salts thereof, and at least one compound chosen from Compound IV, deuterated derivatives of Compound IV, and pharmaceutically acceptable salts thereof. In some embodiments, the deuterated derivative of Compound III is Compound III-d.

Any of Compound I, deuterated derivatives of Compound I, and pharmaceutically acceptable salts of Compound I or its deuterated derivatives, together with one or more of Compounds II, III, III-d, and IV, and their deuterated derivatives and pharmaceutically acceptable salts thereof, can be combined in a single pharmaceutical composition or separate pharmaceutical compositions. Such pharmaceutical compositions can be administered once daily or multiple times daily, such as twice daily. In some embodiments, the disclosure features a pharmaceutical composition comprising at least one compound chosen from Compound I, deuterated derivatives of Compound I, and pharmaceutically acceptable salts of Compound I or its deuterated derivatives, and at least one pharmaceutically acceptable carrier.

In some embodiments, the disclosure features a pharmaceutical composition comprising at least one compound chosen from Compound I, deuterated derivatives of Compound I, and pharmaceutically acceptable salts of Compound I or its deuterated derivatives, at least one compound chosen from Compound II, deuterated derivatives of Compound II, and pharmaceutically acceptable salts thereof, and at least one pharmaceutically acceptable carrier.

In some embodiments, the disclosure features a pharmaceutical composition comprising at least one compound chosen from Compound I, deuterated derivatives of Compound I, and pharmaceutically acceptable salts of Compound I or its deuterated derivatives, at least one compound chosen from Compound III, deuterated derivatives of Compound III, and pharmaceutically acceptable salts thereof, and at least one pharmaceutically acceptable carrier. In some embodiments, the deuterated derivative of Compound III is Compound III-d.

In some embodiments, the disclosure features a pharmaceutical composition comprising at least one compound chosen from Compound I, deuterated derivatives of Compound I, and pharmaceutically acceptable salts of Compound I or its deuterated derivatives, at least one compound chosen from Compound IV, deuterated derivatives of Compound IV, and pharmaceutically acceptable salts thereof, and at least one pharmaceutically acceptable carrier.

In some embodiments, the disclosure features a pharmaceutical composition comprising (a) at least one compound chosen from Compound I, deuterated derivatives of Compound I, and pharmaceutically acceptable salts of Compound I or its deuterated derivatives, (b) at least one compound chosen from Compound II and pharmaceutically acceptable salts thereof, (c) at least one compound chosen from Compound III, Compound III-d, and pharmaceutically acceptable salts thereof, and (d) at least one pharmaceutically acceptable carrier.

In some embodiments, the disclosure features a pharmaceutical composition comprising (a) at least Compound I, deuterated derivatives of Compound I, and pharmaceutically acceptable salts of Compound I or its deuterated derivatives, (b) at least one compound chosen from Compound III, Compound III-d, and pharmaceutically acceptable salts thereof, (c) at least one compound chosen from Compound IV and pharmaceutically acceptable salts thereof, and (d) at least one pharmaceutically acceptable carrier.

In any of the embodiments described above or throughout this specification, the pharmaceutical salt of Compound I may be a potassium salt. In any of the embodiments described above or throughout this specification, the pharmaceutical salt of Compound I may be a sodium salt. In any of the embodiments described above or throughout this specification, the pharmaceutical salt of Compound I may be a calcium salt.

In any of the embodiments described above or throughout the specification, the deuterated derivative of Compound I may be selected from:

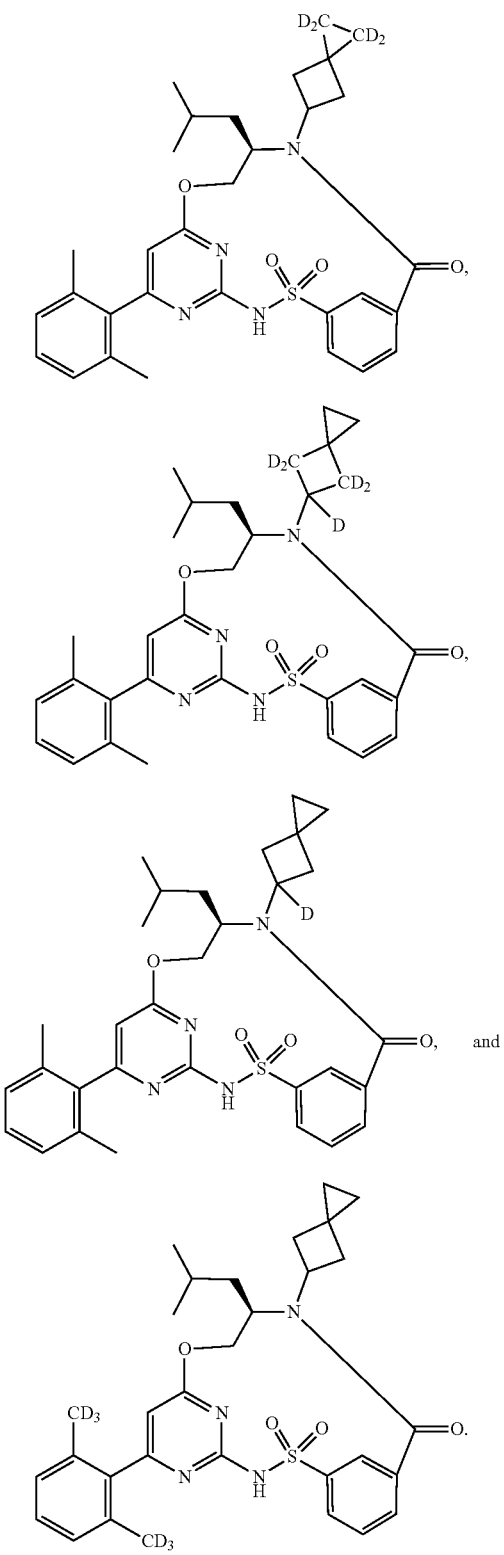

In some embodiments, the deuterated derivative of Compound I is Compound Ia or a pharmaceutically acceptable salt thereof. In some embodiments, the deuterated derivative of Compound I is Compound Ib or a pharmaceutically acceptable salt thereof. In some embodiments, the deuterated derivative of Compound I is Compound Ic or a pharmaceutically acceptable salt thereof. In some embodiments, the deuterated derivative of Compound I is Compound Id or a pharmaceutically acceptable salt thereof.

Any of the embodiments described above may comprise at least one additional active pharmaceutical ingredient. In some embodiments, the at least one additional active pharmaceutical ingredient is a CFTR modulator. In some embodiments, the at least one additional active pharmaceutical ingredient is a CFTR corrector. In some embodiments, the at least one additional active pharmaceutical ingredient is a CFTR potentiator.

In some embodiments, at least one additional active pharmaceutical ingredient is selected from mucolytic agents, bronchodialators, antibiotics, anti-infective agents, and anti-inflammatory agents.

As described above, pharmaceutical compositions disclosed herein may comprise at least one pharmaceutically acceptable carrier. The at least one pharmaceutically acceptable carrier may be chosen from adjuvants and vehicles. The at least one pharmaceutically acceptable carrier, as used herein, includes any and all solvents, diluents, other liquid vehicles, dispersion aids, suspension aids, surface active agents, isotonic agents, thickening agents, emulsifying agents, preservatives, solid binders, and lubricants, surfactants, disintegrants, and fillers as suited to the particular dosage form desired. Remington: *The Science and Practice of Pharmacy,* 21st edition, 2005, ed. D. B. Troy, Lippincott Williams & Wilkins, Philadelphia, and *Encyclopedia of Pharmaceutical Technology,* eds. J. Swarbrick and J. C. Boylan, 1988-1999, Marcel Dekker, New York disclose various carriers used in formulating pharmaceutical compositions and known techniques for the preparation thereof. Except insofar as any conventional carrier is incompatible with the compounds of this disclosure, such as by producing any undesirable biological effect or otherwise interacting in a deleterious manner with any other component(s) of the pharmaceutical composition, its use is contemplated to be within the scope of this disclosure. Non-limiting examples of suitable pharmaceutically acceptable carriers include, but are not limited to, ion exchangers, alumina, aluminum stearate, lecithin, serum proteins (such as human serum albumin), buffer substances (such as phosphates, glycine, sorbic acid, and potassium sorbate), partial glyceride mixtures of saturated vegetable fatty acids, water, salts, and electrolytes (such as protamine sulfate, disodium hydrogen phosphate, potassium hydrogen phosphate, sodium chloride, and zinc salts), colloidal silica, magnesium trisilicate, polyvinyl pyrrolidone, polyacrylates, waxes, polyethylene-polyoxypropylene-block polymers, wool fat, sugars (such as lactose, glucose and sucrose), starches (such as corn starch and potato starch), cellulose and its derivatives (such as sodium carboxymethyl cellulose, ethyl cellulose and cellulose acetate), powdered tragacanth, malt, gelatin, talc, excipients (such as cocoa butter and suppository waxes), oils (such as peanut oil, cottonseed oil, safflower oil, sesame oil, olive oil, corn oil and soybean oil), glycols (such as propylene glycol and polyethylene glycol), esters (such as ethyl oleate and ethyl laurate), agar, buffering agents (such as magnesium hydroxide and aluminum hydroxide), alginic acid, pyrogen-free water, isotonic saline, Ringer's solution, ethyl alcohol, phosphate buffer solutions, non-toxic compatible lubricants (such as magnesium stearate), surfactants (such as sodium lauryl sulfate), coloring agents, releasing agents, coating agents, sweetening agents, flavoring agents, perfuming agents, preservatives, and antioxidants.

It will also be appreciated that a pharmaceutical composition of this disclosure, including a pharmaceutical composition comprising any of the combinations described previously, can be employed in combination therapies; that is, the compositions can be administered concurrently with, prior to, or subsequent to at least one active pharmaceutical ingredient(s) or medical procedure(s). Pharmaceutical compositions comprising Compound I, deuterated derivatives of Compound I, and pharmaceutically acceptable salts of Compound I or its deuterated derivatives, and optionally including any of the combinations described above can be used to treat CF.

Any suitable pharmaceutical compositions known in the art can be used for Compound I, deuterated derivatives of Compound I, and pharmaceutically acceptable salts of Compound I or its deuterated derivatives, Compound II, Compound III, Compound III-d, Compound IV, and pharmaceutically acceptable salts thereof. Some exemplary pharmaceutical compositions for Compound II and its pharmaceutically acceptable salts can be found in WO 2011/119984, WO 2014/014841, and WO 2015/160787, all of which are incorporated herein by reference. Some exemplary pharmaceutical compositions for Compound III and its pharmaceutically acceptable salts can be found in WO 2007/134279, WO 2010/019239, WO 2011/019413, WO 2012/027731, and WO 2013/130669, all of which are incorporated herein by reference. Some exemplary pharmaceutical compositions for Compound III-d and its pharmaceutically acceptable salts can be found in WO 2017/053455 and WO 2018/080591. Some exemplary pharmaceutical compositions for Compound IV and its pharmaceutically acceptable salts can be found in WO 2010/037066, WO 2011/127241, WO 2013/112804, and WO 2014/071122, all of which are incorporated herein by reference.

In some embodiments, the pharmaceutical compositions are a tablet. In some embodiments, the tablets are suitable for oral administration.

These combinations are useful for treating CF caused by a mutation in the CFTR gene.

A CFTR mutation may affect the CFTR quantity, i.e., the number of CFTR channels at the cell surface, or it may impact CFTR function, i.e., the functional ability of each channel to open and transport ions. Mutations affecting CFTR quantity include mutations that cause defective synthesis (Class I defect), mutations that cause defective processing and trafficking (Class II defect), mutations that cause reduced synthesis of CFTR (Class V defect), and mutations that reduce the surface stability of CFTR (Class VI defect). Mutations that affect CFTR function include mutations that cause defective gating (Class III defect) and mutations that cause defective conductance (Class IV defect). Some CFTR mutations exhibit characteristics of multiple classes.

In some embodiments, disclosed herein are methods of treating, lessening the severity of, or symptomatically treating CF in a patient comprising administering an effective amount of a compound, pharmaceutically acceptable salt thereof, or a deuterated analog of any of the foregoing; or a pharmaceutical composition of this disclosure to a patient, such as a human, wherein the patient has CF. In some embodiments, the patient has an F508del/minimal function (MF) genotype, F508del/F508del genotype (homozygous for the F508del mutation), F508del/gating genotype, or F508del/residual function (RF) genotype. In some embodiments, the patient is heterozygous for the F508del mutation.

As used herein, "minimal function (MF) mutations" refer to CFTR gene mutations associated with minimal CFTR function (little-to-no functioning CFTR protein) and include, for example, mutations associated with severe defects in the ability of the CFTR channel to open and close (known as defective channel gating or "gating mutations"); mutations associated with severe defects in the cellular processing of CFTR and its delivery to the cell surface; mutations associated with no (or minimal) CFTR synthesis; and mutations associated with severe defects in channel conductance.

In some embodiments, the patient has an F508del mutation on one allele and a mutation on the other allele selected from Table 2.

TABLE 2

CFTR Mutations
Mutation

| | | | | |
|---|---|---|---|---|
| Q2X | L218X | Q525X | R792X | E1104X |
| S4X | Q220X | G542X | E822X | W1145X |
| W19X | Y275X | G550X | W882X | R1158X |
| G27X | C276X | Q552X | W846X | R1162X |
| Q39X | Q290X | R553X | Y849X | S1196X |
| W57X | G330X | E585X | R851X | W1204X |
| E60X | W401X | G673X | Q890X | L1254X |
| R75X | Q414X | Q685X | S912X | S1255X |
| L88X | S434X | R709X | Y913X | W1282X |
| E92X | S466X | K710X | Q1042X | Q1313X |
| Q98X | S489X | Q715X | W1089X | Q1330X |
| Y122X | Q493X | L732X | Y1092X | E1371X |
| E193X | W496X | R764X | W1098X | Q1382X |
| W216X | C524X | R785X | R1102X | Q1411X |
| 185 + 1G→T | 711 + 5G→A | 1717 − 8G→A | 2622 + 1G→A | 3121 − 1G→A |
| 296 + 1G→A | 712 − 1G→T | 1717 − 1G→A | 2790 − 1G→C | 3500 − 2A→G |
| 296 + 1G→T | 1248 + 1G→A | 1811 + 1G→C | 3040G→C | 3600 + 2insT |
| 405 + 1G→A | 1249 − 1G→A | 1811 + 1.6kbA→G | (G970R) | 3850 − 1G→A |
| 405 + 3A→C | 1341 + 1G→A | 1811 + 1643G→T | 3120G→A | 4005 + 1G→A |
| 406 − 1G→A | 1525 − 2A→G | 1812 − 1G→A | 3120 + 1G→A | 4374 + 1G→T |
| 621 + 1G→T | 1525 − 1G→A | 1898 + 1G→A | 3121 − 2A→G | |
| 711 + 1G→T | | 1898 + 1G→C | | |
| 182delT | 1078delT | 1677delTA | 2711delT | 3737delA |
| 306insA | 1119delA | 1782delA | 2732insA | 3791delC |
| 306delTAGA | 1138insG | 1824delA | 2869insG | 3821delT |

TABLE 2-continued

CFTR Mutations
Mutation

| | | | | |
|---|---|---|---|---|
| 365-366insT | 1154insTC | 1833delT | 2896insAG | 3876delA |
| 394delTT | 1161delC | 2043delG | 2942insT | 3878delG |
| 442delA | 1213delT | 2143delT | 2957delT | 3905insT |
| 444delA | 1259insA | 2183AA→G | 3007delG | 4016insT |
| 457TAT→G | 1288insTA | 2184delA | 3028delA | 4021dupT |
| 541delC | 1343delG | 2184insA | 3171delC | 4022insT |
| 574delA | 1471delA | 2307insA | 3171insC | 4040delA |
| 663delT | 1497delGG | 2347delG | 3271delGG | 4279insA |
| 849delG | 1548delG | 2585delT | 3349insT | 4326delTC |
| 935delA | 1609del CA | 2594delGT | 3659delC | |

| | | |
|---|---|---|
| CFTRdele1 | CFTRdele16-17b | 1461ins4 |
| CFTRdele2 | CFTRdele17a, 17b | 1924del7 |
| CFTRdele2, 3 | CFTRdele17a-18 | 2055del9→A |
| CFTRdele2-4 | CFTRdele19 | 2105-2117del13insAGAAA |
| CFTRdele3-10, 14b-16 | CFTRdele19-21 | 2372del8 |
| CFTRdele4-7 | CFTRdele21 | 2721del11 |
| CFTRdele4-11 | CFTRdele22-24 | 2991del32 |
| CFTR50kbdel | CFTRdele22, 23 | 3667ins4 |
| CFTRdup6b-10 | 124del23bp | 4010del4 |
| CFTRdele11 | 602del14 | 4209TGTT→AA |
| CFTRdele13, 14a | 852del22 | |
| CFTRdele14b-17b | 991del5 | |

| | | | |
|---|---|---|---|
| A46D | V520F | Y569D | N1303K |
| G85E | A559T | L1065P | |
| R347P | R560T | R1066C | |
| L467P | R560S | L1077P | |
| I507del | A561E | M1101K | |

In some embodiments, the compositions disclosed herein are useful for treating or lessening the severity of CF in patients with certain genotypes exhibiting residual CFTR activity.

In some embodiments, compositions disclosed herein are useful for treating, lessening the severity of, or symptomatically treating CF in patients within certain clinical phenotypes, e.g., a mild to moderate clinical phenotype that typically correlates with the amount of residual CFTR activity in the apical membrane of epithelia. Such phenotypes include patients exhibiting pancreatic sufficiency.

In some embodiments, the compositions disclosed herein are useful for treating, lessening the severity of, or symptomatically treating patients diagnosed with pancreatic sufficiency, idiopathic pancreatitis, and congenital bilateral absence of the vas deferens, or mild lung disease, wherein the patient exhibits residual CFTR activity.

In some embodiments, this disclosure relates to a method of augmenting or inducing anion channel activity in vitro or in vivo, comprising contacting the channel with a composition disclosed herein. In some embodiments, the anion channel is a chloride channel or a bicarbonate channel. In some embodiments, the anion channel is a chloride channel.

The exact amount of a pharmaceutical composition required will vary from subject to subject, depending on the species, age, and general condition of the subject, the severity of the disease, the particular agent, its mode of administration, and the like. The compounds of this disclosure may be formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of this disclosure will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex, and diet of the patient; the time of administration, route of administration, and rate of excretion of the specific compound employed; the duration of the treatment; drugs used in combination or coincidental with the specific compound employed, and like factors well known in the medical arts.

In some embodiments, the disclosure also is directed to methods of treatment using isotope-labeled derivatives of the aforementioned compounds, which have the same structures as disclosed herein except that one or more atoms therein have been replaced by an atom or atoms having an atomic mass or mass number which differs from the atomic mass or mass number of the atom which usually occurs naturally (isotope labeled). Examples of isotopes which are commercially available and suitable for the disclosure include isotopes of hydrogen, carbon, nitrogen, oxygen, phosphorus, fluorine and chlorine, for example $^2$H, $^3$H, $^{13}$C, $^{14}$C, $^{15}$N, $^{17}$O, $^{18}$O, $^{31}$P, $^{32}$P, $^{35}$S, $^{18}$F, and $^{36}$Cl, respectively.

The isotope-labeled compounds and salts can be used in a number of beneficial ways. They can be suitable for medicaments and/or various types of assays, such as substrate tissue distribution assays. For example, tritium ($^3$H)- and/or carbon-14 ($^{14}$C)-labeled compounds are particularly useful for various types of assays, such as substrate tissue distribution assays, due to relatively simple preparation and excellent detectability. For example, deuterium ($^2$H)-labeled ones are therapeutically useful with potential therapeutic advantages over the non-$^2$H-labeled compounds. In general, deuterium ($^2$H)-labeled compounds and salts can have higher metabolic stability as compared to those that are not isotope-labeled owing to the kinetic isotope effect described below. Higher metabolic stability translates directly into an increased in vivo half-life or lower dosages, which could be desired. The isotope-labeled compounds and salts can usually be prepared by carrying out the procedures disclosed in the synthesis schemes and the related description, in the example part and in the preparation part in the present text, replacing a non-isotope-labeled reactant by a readily available isotope-labeled reactant.

In some embodiments, the isotope-labeled compounds and salts are deuterium-labeled (($^2$H)-labeled) ones. In some specific embodiments, the isotope-labeled compounds and salts are deuterium-labeled, wherein one or more hydrogen atoms therein have been replaced by deuterium. In chemical structures, deuterium is represented as "$^2$H" or "D."

The deuterium-labeled compounds and salts can manipulate the oxidative metabolism of the compound by way of the primary kinetic isotope effect. The primary kinetic isotope effect is a change of the rate for a chemical reaction that results from exchange of isotopic nuclei, which in turn is caused by the change in ground state energies necessary for covalent bond formation after this isotopic exchange. Exchange of a heavier isotope usually results in a lowering of the ground state energy for a chemical bond and thus causes a reduction in the rate-limiting bond breakage. If the bond breakage occurs in or in the vicinity of a saddle-point region along the coordinate of a multi-product reaction, the product distribution ratios can be altered substantially. For explanation: if deuterium is bonded to a carbon atom at a non-exchangeable position, rate differences of $k_M/k_D$=2-7 are typical. For a further discussion, see S. L. Harbeson and R. D. Tung, *Deuterium In Drug Discovery and Development*, Ann. Rep. Med. Chem. 2011, 46, 403-417; and T. G. Gant "Using deuterium in drug discovery: leaving the label in the drug" J. Med. Chem. 2014, 57, 3595-3611, relevant portions of which are independently incorporated herein by reference.

In the compounds of this disclosure, any atom not specifically designated as a particular isotope is meant to represent any stable isotope of that atom. Unless otherwise stated, when a position is designated specifically as "H" or "hydrogen," the position is understood to have hydrogen at its natural abundance isotopic composition.

The concentration of the isotope(s) (e.g., deuterium) incorporated into the isotope-labeled compounds and salts of the disclosure may be defined by the isotopic enrichment factor. The term "isotopic enrichment factor" as used herein means the ratio between the isotopic abundance and the natural abundance of a specified isotope. In some embodiments, if a substituent in a compound of the disclosure is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

When discovering and developing therapeutic agents, the person skilled in the art attempts to optimize pharmacokinetic parameters while retaining desirable in vitro properties. It may be reasonable to assume that many compounds with poor pharmacokinetic profiles are susceptible to oxidative metabolism.

One of ordinary skill in the art would understand that deuteration of one or more metabolically labile positions on a compound or active metabolite may lead to improvement of one or more superior DMPK properties while maintaining biological activity, as compared to the corresponding hydrogen analogs. The superior DMPK property or properties may have an impact on the exposure, half-life, clearance, metabolism, and/or even food requirements for optimal absorption of the drug product. Deuteration may also change the metabolism at other non-deuterated positions of the deuterated compound.

The disclosure provides a process for preparing Compound I, comprising reacting compound 8:

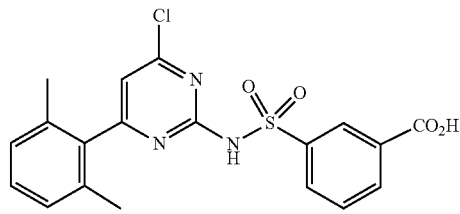

with compound 3:

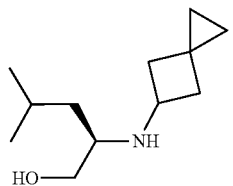

and a base and coupling agent to produce Compound I.

In some embodiments, the base is sodium tert-butoxide.

In some embodiments, the coupling agent is HATU.

The disclosure provides an alternative process for preparing Compound I, comprising:

a) reacting compound 8 and compound 3 with a base, and subsequent treatment with HCl to produce compound 9:

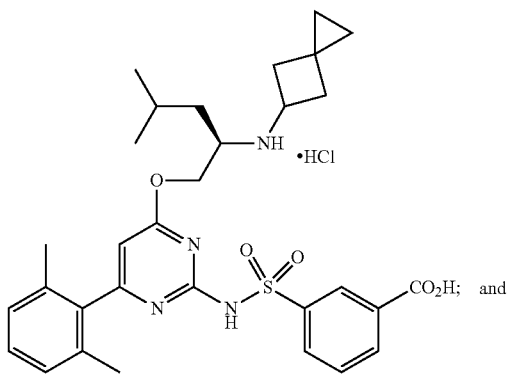

and b) reacting compound 9 with a base and coupling agent to produce Compound I.

In some embodiments, the base of step a) is sodium tert-butoxide.

In some embodiments, the base is of step b) is triethylamine.

In some embodiments, the coupling agent is HATU.

The disclosure further provides a process for preparing compound compound 8, comprising:
a) reacting compound 7:

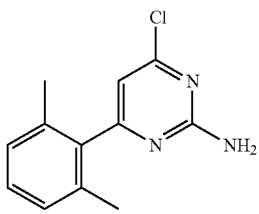

7 with methyl 3-chlorosulfonylbenzoate and a first base, subsequent treatment with a second base, followed by treating the reaction mixture with an acid to produce compound 8.

In some embodiments, the first base is lithium tert-amoxide.

In some embodiments, the second base is sodium hydroxide.

In some embodiments, the acid is HCl.

The disclosure further provides a process for preparing compound 7, comprising treating compound 7·HCl:

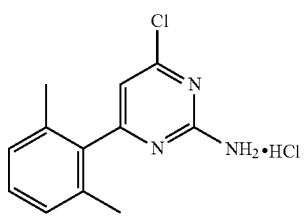

7·HCl with a base to produce compound 7.

In some embodiments, the base is sodium hydroxide.

The disclosure further provides a process for preparing compound 7·HCl, comprising reacting compound 6:

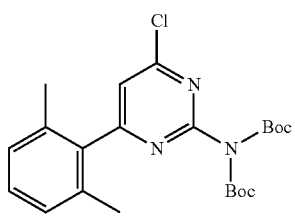

6 with HCl to produce compound 7·HCl.

The disclosure further provides a process for preparing compound 6, comprising reacting compound 5:

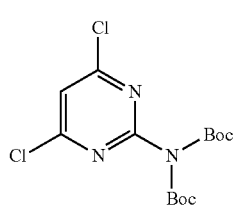

5 with 2,6-dimethylphenylboronic acid, a transition-metal catalyst, and base to produce compound 6.

In some embodiments, the transition-metal catalyst is $Pd(dppf)Cl_2$.

In some embodiments, the base is cesium carbonate.

The disclosure further provides a process for preparing compound 5, comprising reacting compound 4:

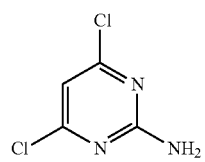

4 with $Boc_2O$ and a base to produce compound 5.

In some embodiments, the base is DMAP.

The disclosure further provides a process for preparing compound 3:

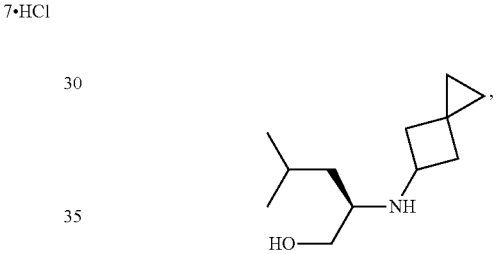

3 comprising:
a) reacting compound 1:

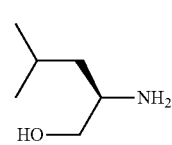

1 with compound 2:

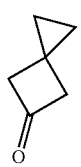

2 and a reducing agent to produce compound 3.

In some embodiments, the reducing agent is $NaBH(OAc)_3$.

The disclosure provides a process for preparing Compound Ia, comprising reacting compound 20:

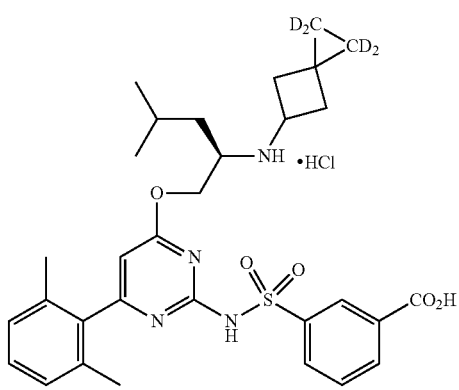

with a base and coupling agent to produce compound Ia.

In some embodiments, the base is DIEA.

In some embodiments, the coupling agent is HATU.

The disclosure further provides a process for preparing compound 20, comprising reacting compound 19:

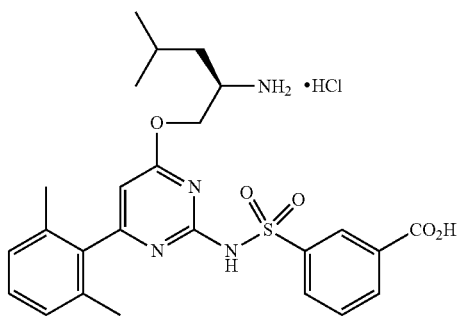

and compound 17:

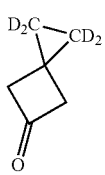

with a reducing agent to produce compound 20.

In some embodiments, the reducing agent is NaBH(OAc)$_3$.

The disclosure further provides a process for preparing compound 19, comprising reacting compound 18:

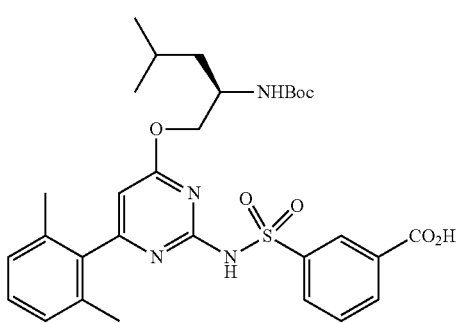

with HCl to produce compound 19.

The disclosure further provides a process for preparing compound 18, comprising:

a) reacting compound 8:

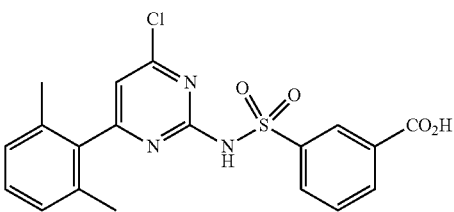

with compound 1:

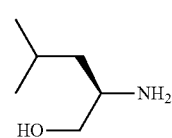

and a base and b) reacting the product of step a) with Boc$_2$O to produce compound 18.

In some embodiments, the base is sodium tert-butoxide.

The disclosure provides a process for preparing compound 17, comprising reacting compound 16:

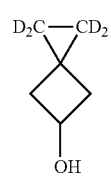

with an oxidant to produce compound 17.

In some embodiments, the oxidant is CrO$_3$/pyridine.

The disclosure further provides a process for preparing compound 16, comprising reacting compound 15:

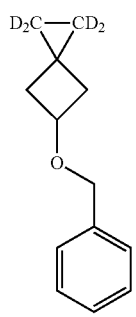

15 with H₂ and a transition metal catalyst to produce compound 16.

In some embodiments, the transition-metal catalytst is palladium on carbon.

The disclosure further provides a process for preparing compound 15, comprising reacting compound 14:

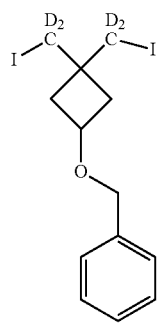

14 with a reducing agent to produce compound 15.

In some embodiments, the reducing agent is Zn.

The disclosure further provides a process for preparing compound 14, comprising
a) reacting compound 13:

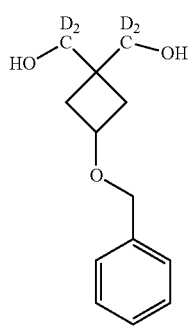

13 with a sulfonyl chloride and base, and
b) reacting the product of step a) with a source of iodide to produce compound 14.

In some embodiments, the sulfonyl chloride is methanesulfonyl chloride.

In some embodiments, the source of iodide is sodium iodide.

The disclosure further provides a process for preparing compound 13, comprising reacting compound 12:

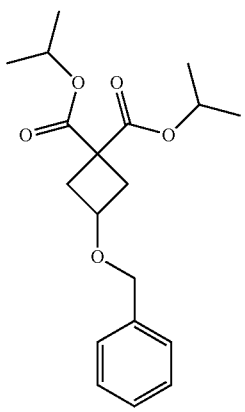

12 with a reducing agent to produce compound 13.

In some embodiments, the reducing agent is LiAlD₄.

The disclosure further provides a process for preparing compound 12, comprising reacting compound 11:

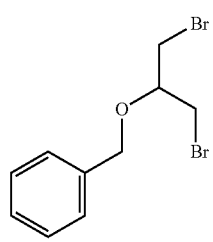

11 with a dialkylmalonate and a base to produce compound 12.

In some embodiments, the dialkylmalonate is diisopropyl propanedioate.

In some embodiments, the base is sodium hydride.

The disclosure further provides a process for preparing compound 11, comprising converting compound 10:

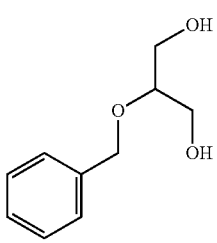

10 into compound 11.

In some embodiments, the conversion of compound 10 into compound 11 is performed with CBr₄ and PPh₃.

The disclosure provides a process for preparing Compound Ib, comprising reacting compound 22:

22

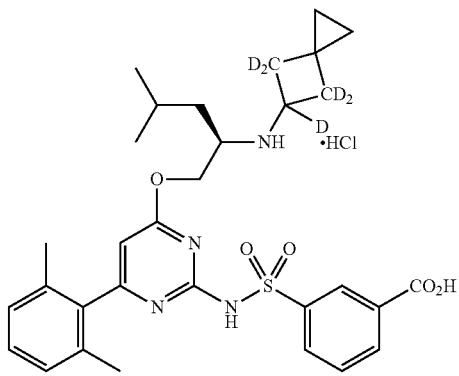

with a base and coupling agent to produce compound Ib.

In some embodiments, the base is DIEA.

In some embodiments, the coupling agent is HATU.

The disclosure further provides a process for preparing compound 22, comprising reacting compound 19 with compound 21:

21

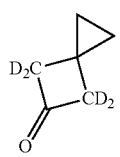

and a reducing agent to produce compound 22.

In some embodiments, the reducing agent is NaBD$_3$CN.

The disclosure further provides a process for preparing compound 21, comprising reacting compound 2 with a base and a source of deuterium to produce compound 21.

In some embodiments, the base is potassium carbonate.

In some embodiments, the source of deuterium is D$_2$O.

The disclosure provides a process for preparing Compound Ic, comprising reacting compound 23:

23

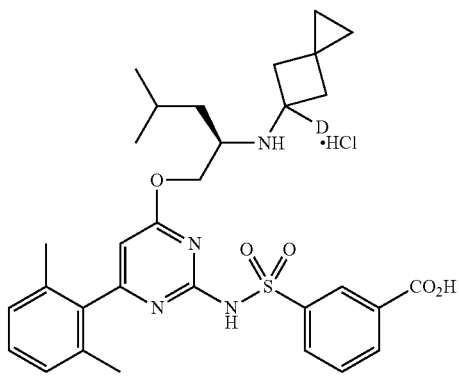

with a base a coupling agent to produce compound Ic.

In some embodiments, the base is DIEA.

In some embodiments, the coupling agent is HATU.

The disclosure further provides a process for preparing 23, comprising reacting compound 19 with compound 2 and a reducing agent to produce compound 23.

In some embodiments, the reducing agent is NaBD$_3$CN.

The disclosure provides a process for preparing Compound Id:

Id

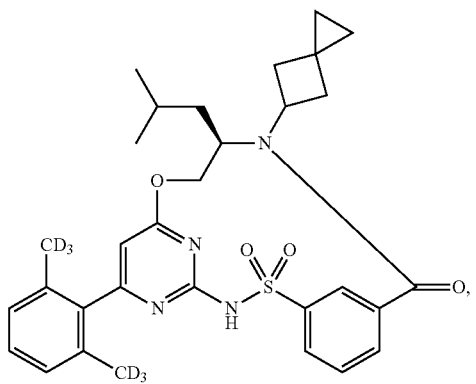

comprising reacting compound 35:

35

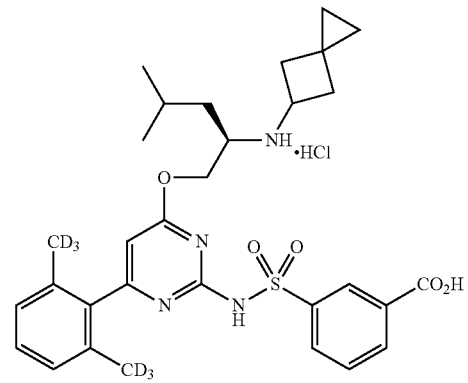

with a base and coupling agent to produce compound Id.

In some embodiments, the base is DIEA.

In some embodiments, the coupling agent is COMU.

The disclosure further provides a process for preparing compound 35, comprising reacting compound 34:

34

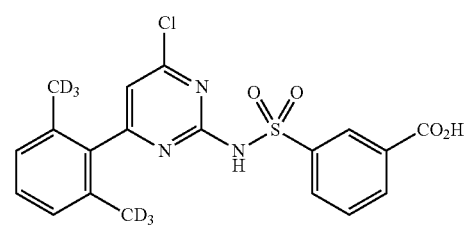

with compound 3·HCl:

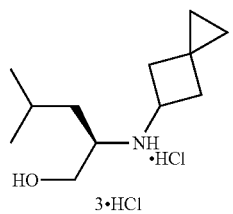

3·HCl and a base to produce compound 35.

In some embodiments, the base is sodium tert-butoxide.

The disclosure further provides a process for preparing compound 34, comprising reacting compound 33:

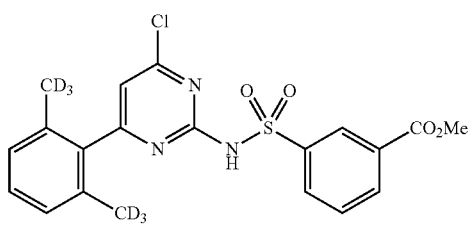

33 with a base to produce compound 34.

In some embodiments, the base is sodium hydroxide.

The disclosure further provides a process for preparing compound 33, comprising reacting compound 32:

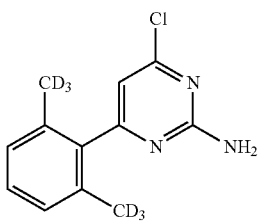

32 with methyl 3-chlorosulfonylbenzoate and a base to produce compound 33.

In some embodiments, the base is lithium tert-amoxide.

The disclosure further provides a process for preparing compound 32, comprising reacting compound 31:

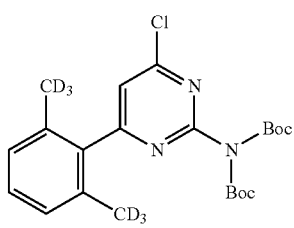

31 with an acid to produce compound 32.

In some embodiments, the acid is HCl.

The disclosure further provides a process for preparing compound 31, comprising reacting compound 5:

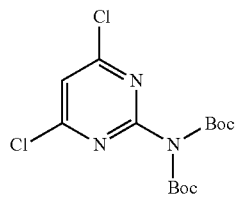

5 with compound 30:

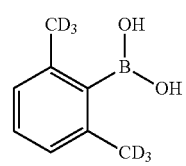

30 and a transition-metal catalyst and a base to produce compound 31.

In some embodiments, the base is cesium carbonate.

In some embodiments, the transition-metal catalyst is Pd(dppf)Cl$_2$.

The disclosure further provides a process for preparing 30, comprising
a) converting compound 29:

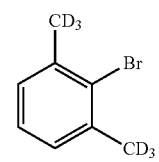

29 into the aryl magnesium iodide derivative,
b) reacting the product of step a) with a trialkyl borate, and
c) reacting the product of step b) with an acid to produce compound 30.

In some embodiments, step a) is performed with Mg and I$_2$.

In some embodiments, the trialkyl borate is trimethyl borate.

In some embodiments, the acid is HCl.

The disclosure further provides a process for preparing compound 29, comprising reacting compound 28:

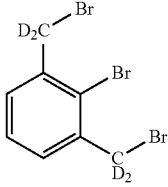

28 with a reducing agent to produce compound 29.

In some embodiments, the reducing agent is LiAlD$_4$.

The disclosure further provides a process for preparing compound 28, comprising converting compound 27:

27

[Structure: 2-bromo-1,3-bis(dideuteriohydroxymethyl)benzene, with D₂C-OH groups at 1,3-positions and Br at 2-position]

into compound 28.

In some embodiments, the convertion of compound 27 into compound 28 is performed with CBr₄ and PPh₃.

The disclosure further provides a process for preparing compound 27, comprising reacting compound 26:

26

[Structure: dimethyl 2-bromoisophthalate]

with a reducing agent to produce compound 27.

In some embodiments, the reducing agent is LiAlD₄.

The disclosure further provides a process for preparing compound 26, comprising reacting compound 25:

25

[Structure: 2-bromoisophthalic acid]

with a base and alkylating agent to produce compound 26.

In some embodiments, the base is potassium carbonate.

In some embodiments, the alkylating agent is iodomethane.

The disclosure further provides a process for preparing compound 25, comprising reacting compound 24:

24

[Structure: 2-bromo-1,3-dimethylbenzene]

with an oxidant to produce compound 25.

In some embodiments, the oxidant is potassium permanganate.

The disclosure further provides a process for preparing compound 3HCl, comprising treating compound 3 with HCl to produce compound 3·HCl.

Exemplary embodiments of the disclosure include:

1. A compound selected from Compound I:

I

[Chemical structure of Compound I]

deuterated derivatives of Compound I, and pharmaceutically acceptable salts thereof.

2. The compound of embodiment 1, wherein the compound is Compound I.

3. The compound of embodiment 1, wherein the deuterated derivative of Compound I is selected from:

Compound Ia

Ia

[Chemical structure of Compound Ia with D₂C and CD₂ labels]

Compound Ib

Ib

[Chemical structure of Compound Ib with D₂C, CD₂, and D labels]

-continued

Compound Ic

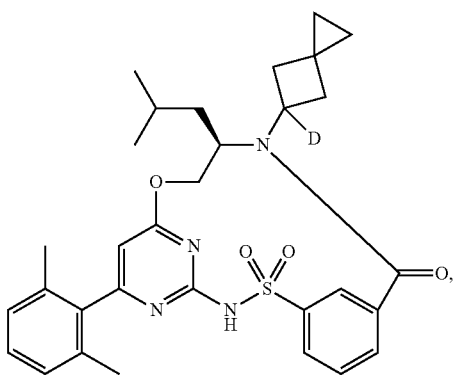

Compound Id

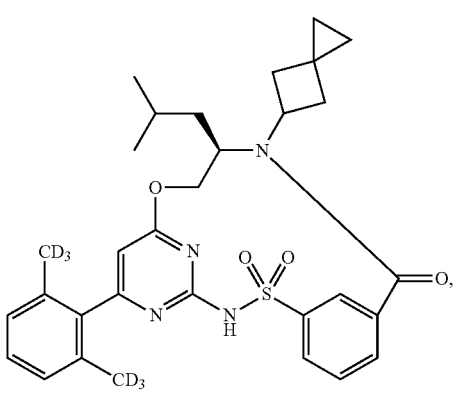

and pharmaceutically acceptable salts thereof.

4. The compound of embodiment 1 or 2, wherein the compound is a potassium salt.

5. The compound of embodiment 1 or 2, wherein the compound is a sodium salt.

6. The compound of embodiment 1 or 2, wherein the compound is a calcium salt.

7. A method of treating a CFTR-mediated disorder, comprising administering an effective amount of the compound of any one of embodiments 1 to 6 to a patient in need thereof.

8. The method of embodiment 7, wherein the CFTR-mediated disorder is CF.

9. The method of embodiment 7, wherein the compound is Compound I or a pharmaceutically acceptable salt thereof.

10. The method of any one of embodiments 7 to 9, further comprising administering one or more compounds selected from:

Compound II

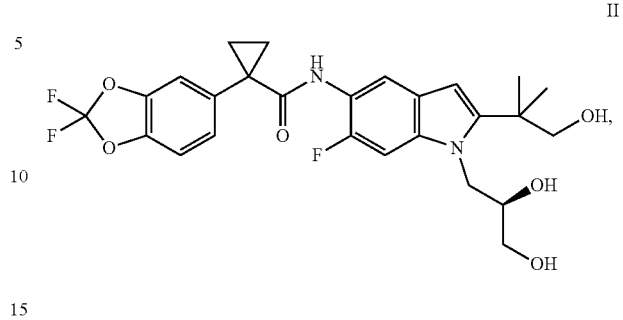

Compound III

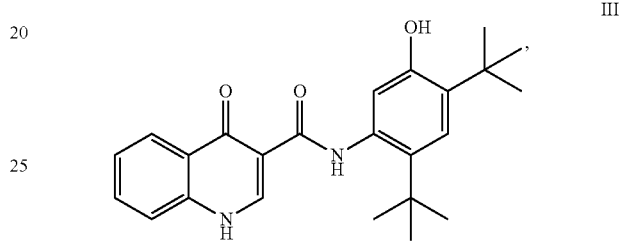

Compound III-d

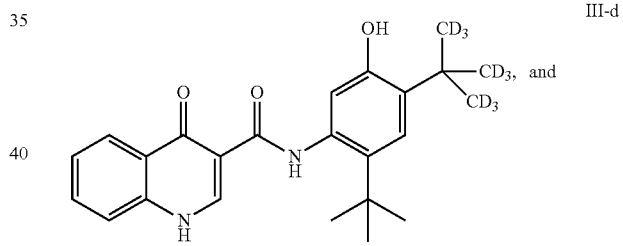

Compound IV

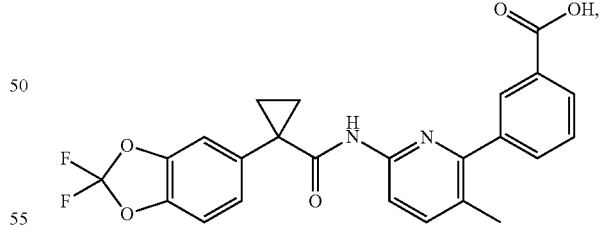

and pharmaceutically acceptable salts of Compounds II, III, III-d, and IV.

11. The method of embodiment 10, comprising administering Compound I and Compound III or Compound III-d.

12. The method of embodiment 10, comprising administering Compound I, Compound II, and Compound III or Compound III-d.

13. A process for preparing Compound I, comprising reacting compound 8:

8

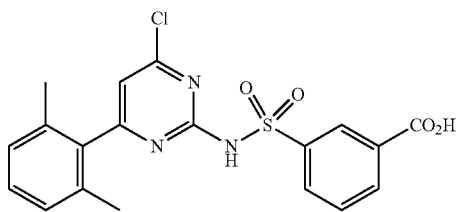

with compound 3:

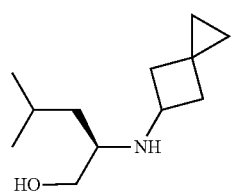

to produce Compound I.

14. A process for preparing Compound I, comprising:
a) reacting compound 8 with compound 3, and subsequent treatment with HCl to produce compound 9:

9

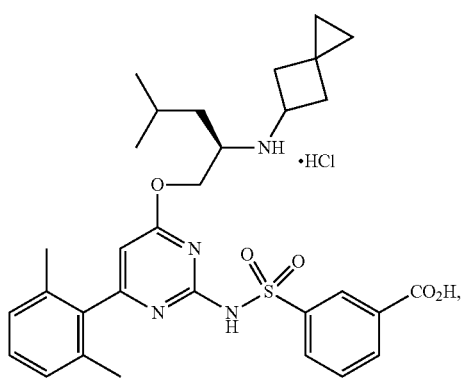

and
b) converting compound 9 into Compound I.

15. The process of embodiment 13 or 14, wherein compound 8 is prepared by
a) reacting compound 7:

7

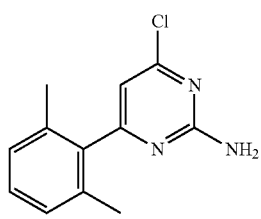

with methyl 3-chlorosulfonylbenzoate and a first base,
b) treatment with a second base, and
c) treating the reaction mixture with HCl to produce compound 8.

16. The process of embodiment 15, wherein compound 7 is prepared by converting compound 7·HCl:

7·HCl

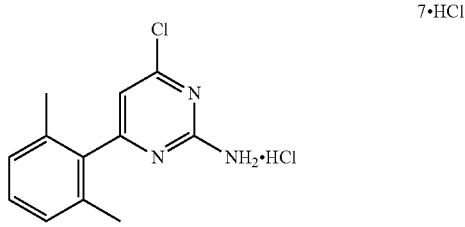

into compound 7.

17. The process of embodiment 16, wherein compound 7·HCl is prepared by converting compound 6:

6

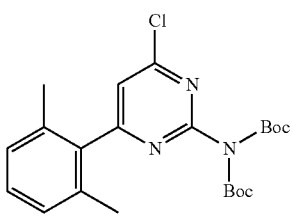

into compound 7·HCl.

18. The process of embodiment 17, wherein compound 6 is prepared by reacting compound 5:

5

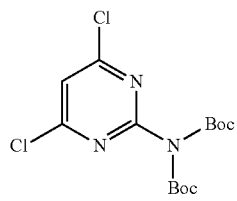

with 2,6-dimethylphenylboronic acid to produce compound 6.

19. The process of embodiment 18, wherein compound 5 is prepared by converting compound 4:

4

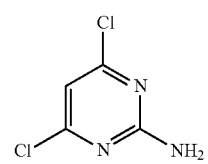

into compound 5.

20. The process of embodiment 13 or 14, wherein compound 3:

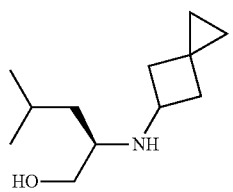

is prepared by reacting compound 1:

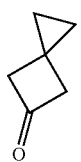

with compound 2:

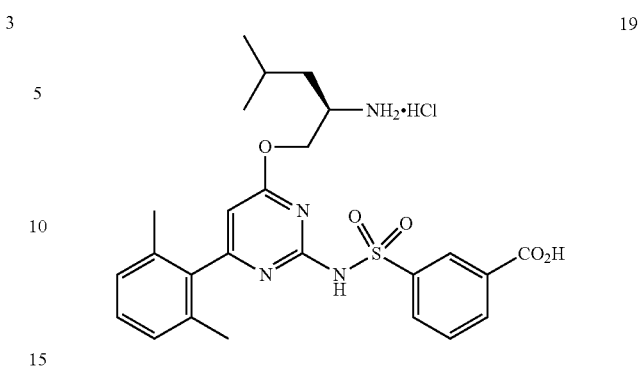

and compound 17:

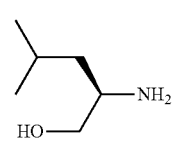

to produce compound 20.

23. The process of embodiment 22, wherein compound 19 is prepared by converting compound 18:

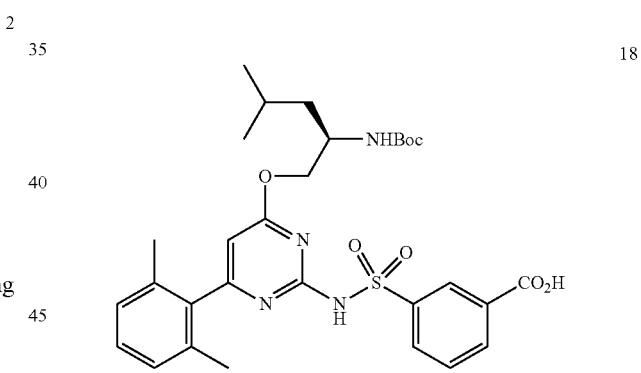

into compound 19.

24. The process of embodiment 23, wherein compound 18 is prepared by a) reacting compound 8 with compound 1:

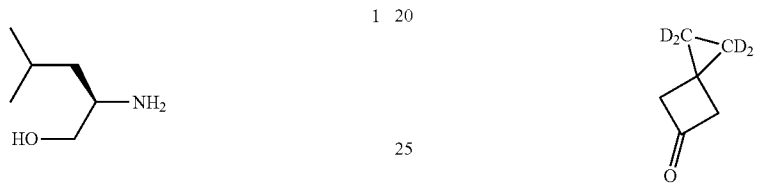

to produce compound 3.

21. A process for preparing Compound Ia, comprising converting compound 20:

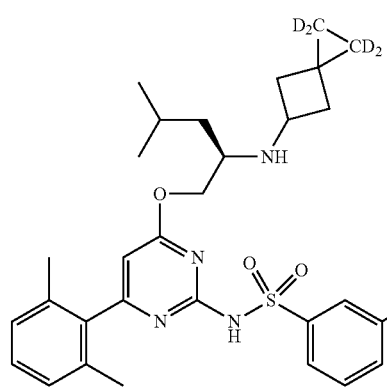

into compound Ia.

22. The process of embodiment 21, wherein compound 20 is produced by reacting compound 19:

b) converting the product of step a) into compound 18.

25. The process of embodiment 22, wherein compound 17 is prepared by converting compound 16:

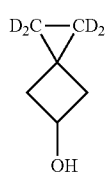

16 into compound 17.
26. The process of embodiment 25, wherein compound 16 is prepared by converting compound 15:

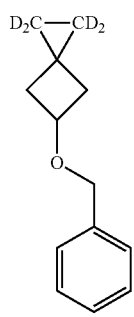

15 into compound 16.
27. The process of embodiment 26, wherein compound 15 is prepared by converting compound 14:

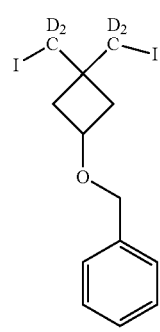

14 into compound 15.
28. The process of embodiment 27, wherein compound 14 is prepared by converting compound 13:

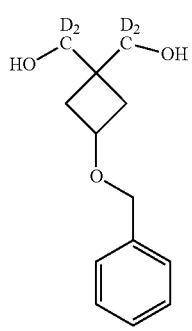

13 into compound 14.

29. The process of embodiment 28, wherein compound 13 is prepared by converting compound 12:

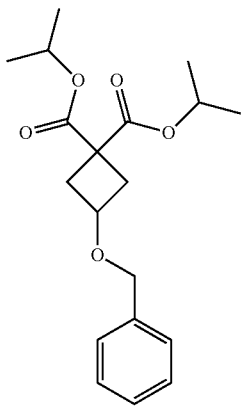

12 into compound 13.
30. The process of embodiment 29, wherein compound 12 is prepared by reacting compound 11:

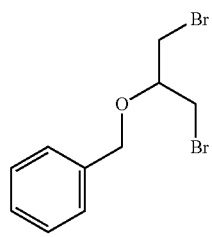

11 with diisopropyl propanedioate to form compound 12.
31. The process of embodiment 30, wherein compound 11 is prepared by converting compound 10:

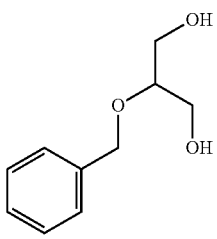

10 into compound 11.
32. A process for preparing Compound Ib, comprising converting compound 22:

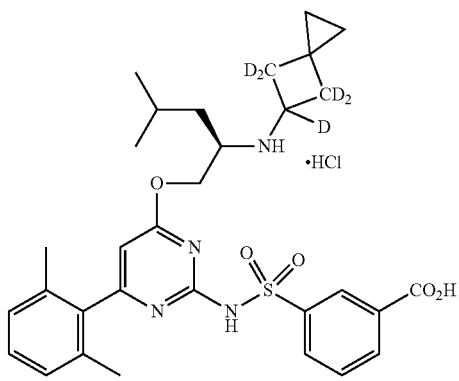

22 into compound Ib.

33. The process of embodiment 32, wherein compound 22 is prepared by reacting compound 19 with compound 21:

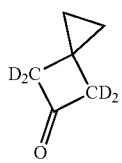

21 to produce compound 22.

34. The process of embodiment 33, wherein compound 21 is prepared by converting compound 2 into compound 21.

35. A process for preparing Compound Ic, comprising converting compound 23:

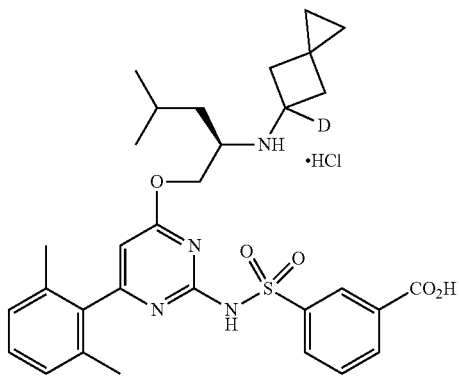

23 into compound Ic.

36. The process of embodiment 35, wherein compound 23 is prepared by reacting compound 19 with compound 2 to produce compound 23.

37. A process for preparing Compound Id:

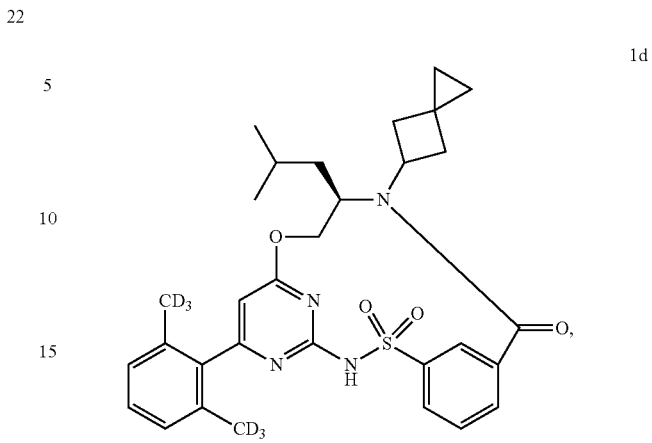

1d comprising converting compound 35:

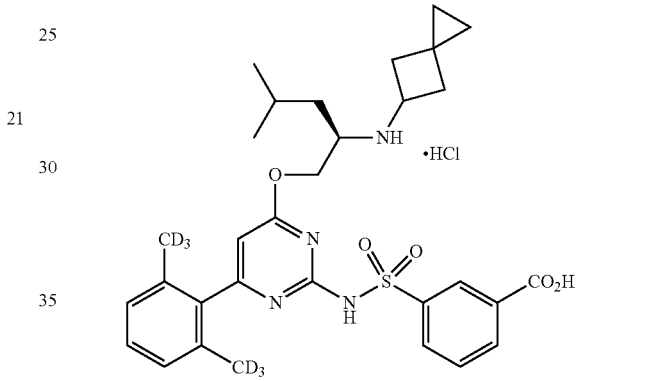

35 into compound Id.

38. The process of embodiment 37, wherein compound 35 is prepared by reacting compound 34:

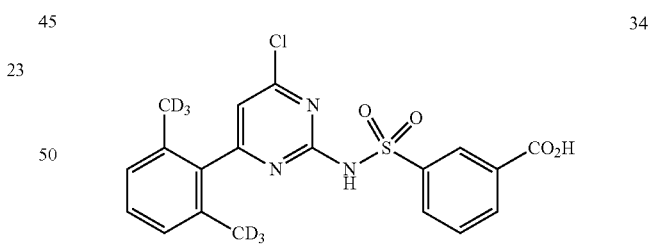

34 with compound 3·HCl:

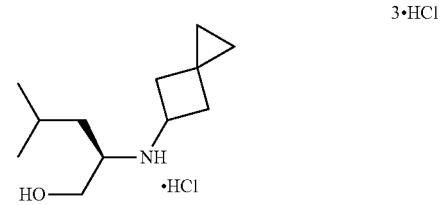

3·HCl to produce compound 35.

39. The process of embodiment 38, wherein compound 34 is prepared by converting compound 33:

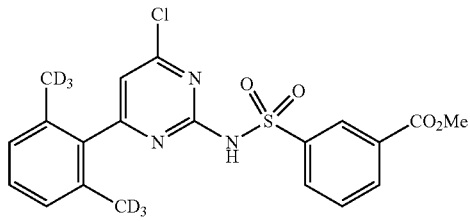

33 into compound 34.

40. The process of embodiment 39, wherein compound 33 is prepared by reacting compound 32:

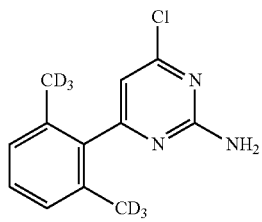

32 with methyl 3-chlorosulfonylbenzoate to produce compound 33.

41. The process of embodiment 40, wherein compound 32 is prepared by converting compound 31:

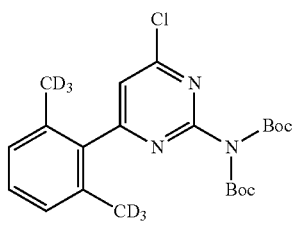

31 into compound 32.

42. The process of embodiment 41, wherein compound 31 is prepared by reacting compound 5:

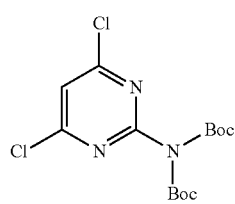

5 with compound 30:

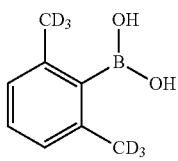

30 to produce compound 31.

43. The process of embodiment 42, wherein compound 30 is prepared by converting compound 29:

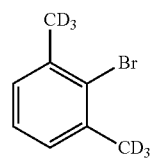

29 into compound 30.

44. The process of embodiment 43, wherein compound 29 is prepared by converting compound 28:

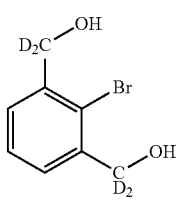

28 into compound 29.

45. The process of embodiment 44, wherein compound 28 is prepared by converting compound 27:

27 into compound 28.

46. The process of embodiment 45, wherein compound 27 is prepared by converting compound 26:

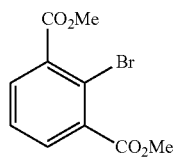

26 into compound 27.

47. The process of embodiment 46, wherein compound 26 is prepared by converting compound 25:

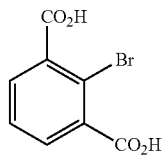

into compound 26.

48. The process of embodiment 47, wherein compound 25 is prepared by converting compound 24:

into compound 25.

49. The process of embodiment 38, wherein compound 3·HCl is prepared by treating compound 3 with HCl to produce compound 3·HCl.

EXAMPLES

Abbreviations

Boc anhydride ((Boc)$_2$O): di-tert-butyl dicarbonate
DCM: dichloromethane
DIEA (DIPEA): N,N-diisopropylethylamine
DMAP: 4-Dimethylaminopyridine
DMF: N,N-dimethylformamide
DMSO: dimethyl sulfoxide
HATU: 1-[Bis(dimethylamino)methylene]-1H-1,2,3-triazolo[4,5-b]pyridinium 3-oxid hexafluorophosphate
COMU: (1-Cyano-2-ethoxy-2-oxoethylidenaminooxy)dimethylamino-morpholino-carbenium hexafluorophosphate
MeOH: methanol
THF: tetrahydrofuran
EtOAc: ethyl acetate
Pd(dppf)Cl$_2$: [1,1'-Bis(diphenylphosphino)ferrocene]dichloropalladium(II)
MeTHF: 2-Methyltetrahydrofuran General UPLC/HPLC Analytical Methods LC Method A: Analytical reverse phase UPLC using an Acquity UPLC BEH C$_{18}$ column (50×2.1 mm, 1.7 μm particle) made by Waters (pn: 186002350), and a dual gradient run from 1-99% mobile phase B over 3.0 min. Mobile phase A=H$_2$O (0.05% CF$_3$CO$_2$H). Mobile phase B=CH$_3$CN (0.035% CF$_3$CO$_2$H). Flow rate=1.2 mL/min, injection volume=1.5 μL, and column temperature=60° C.

LC Method B: Merck Millipore Chromolith SpeedROD C$_{18}$ column (50×4.6 mm) and a dual gradient run from 5-100% mobile phase B over 6 min. Mobile phase A=water (0.1% CF$_3$CO$_2$H). Mobile phase B=acetonitrile (0.1% CF$_3$CO$_2$H).

LC Method C: Merck Millipore Chromolith SpeedROD C$_{18}$ column (50×4.6 mm) and a dual gradient run from 5-100% mobile phase B over 12 min. Mobile phase A=water (0.1% CF$_3$CO$_2$H). Mobile phase B=acetonitrile (0.1% CF$_3$CO$_2$H).

Example 1: Synthesis of (11R)-6-(2,6-Dimethylphenyl)-11-(2-methylpropyl)-12-{spiro[2.3]hexan-5-yl}-9-oxa-2$\lambda^6$-thia-3,5,12,19-tetraazatricyclo[12.3.1.14,8]nonadeca-1(17),4(19),5,7,14(18),15-hexaene-2,2,13-trione (Compound I)

Synthesis of (2R)-4-Methyl-2-(spiro[2.3]hexan-5-ylamino)pentan-1-ol (3)

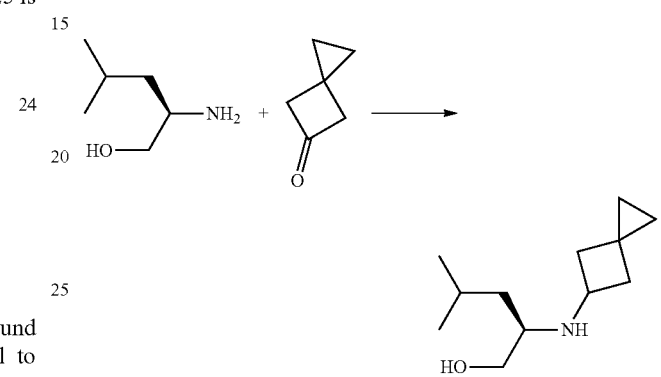

A mixture of spiro[2.3]hexan-5-one (100 g, 1.040 mol) and (2R)-2-amino-4-methyl-pentan-1-ol (123.5 g, 1.054 mol) in dichloroethane (DCE) (1.5 L) was stirred at ambient temperature for 1 h. To the mixture was added sodium triacetoxyborohydride (228 g, 1.076 mol) portionwise. The mixture was stirred at ambient temperature for 18 h. The reaction mixture was diluted with HCl (1.1 L of 2 M, 2.200 mol) until pH was ~1. The aqueous phase was separated and the organic phase extracted with HCl (600 mL of 2 M, 1.200 mol). The organic phase was separated and the aqueous layer was basified with NaOH (550 g of 50% w/w, 6.875 mol) affording a solution at ~pH 12. The mixture was extracted 2× with EtOAc (1 L) and the combined organic phases were washed with brine (150 mL), dried over MgSO$_4$, filtered, and concentrated in vacuo to afford (2R)-4-methyl-2-(spiro[2.3]hexan-5-ylamino)pentan-1-ol (160.7 g, 78%) as a clear oil. Used without further purification. ESI-MS m/z calc. 197.17796, found 198.2 (M+1)$^+$; Retention time: 0.54 minutes (LC method A).

Synthesis of tert-Butyl N-tert-butoxycarbonyl-N-(4,6-dichloro-pyrimidin-2-yl)carbamate (5)

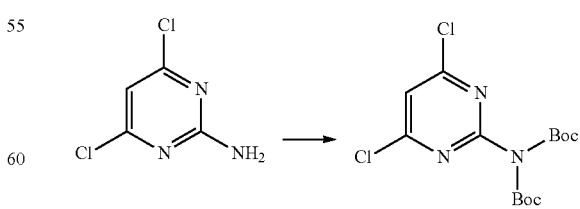

To a solution of 4,6-dichloropyrimidin-2-amine (300 g, 1.829 mol) in DCM (2.1 L) was added (Boc)$_2$O (838 g, 3.840 mol) followed by DMAP (5.6 g, 45.84 mmol). The mixture was stirred at ambient temperature for 6 h. Additional DMAP (5.6 g, 45.84 mmol) was added and the reaction was continued to stir at ambient temperature for 24 h. The mixture was diluted with water (2.1 L) and the organic phase separated. The organic phase was washed with water (2.1 L), 2.1 L of brine, dried over MgSO$_4$, filtered over celite and concentrated in vacuo affording a light orange oil which had a silt in the slurry. The mixture was diluted with ~500 mL of heptane and filtered using an M filter. The precipitate (starting material) was washed with 250 mL of heptane. The filtrate was concentrated in vacuo affording a thick orange oil which was seeded with solid from a previous experiment and crystallized on standing, to afford tert-butyl N-tert-butoxycarbonyl-N-(4,6-dichloropyrimidin-2-yl)carbamate (645 g, 97%) as a light orange hard solid. $^1$H NMR (400 MHz, DMSO-d$_6$) δ 8.07 (s, 1H), 1.44 (s, 18H). ESI-MS m/z calc. 363.07526, found 364.1 (M+1)$^+$; Retention time: 2.12 minutes (LC method A).

Synthesis of tert-Butyl N-tert-butoxycarbonyl-N-[4-chloro-6-(2,6-dimethyl-phenyl)pyrimidin-2-yl]carbamate (6)

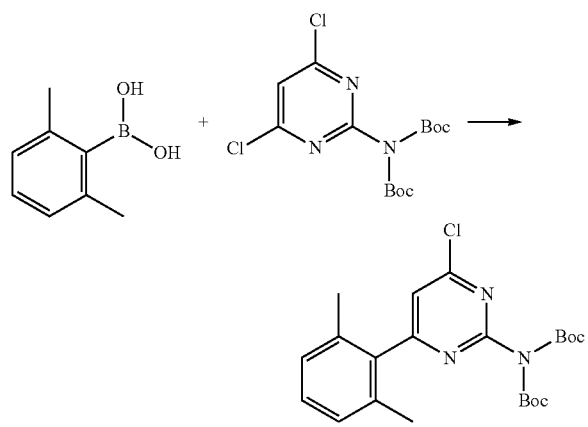

All solvents were degassed prior to use. To a slurry of tert-butyl N-tert-butoxycarbonyl-N-(4,6-dichloropyrimidin-2-yl)carbamate (88 g, 241.6 mmol), (2,6-dimethylphenyl) boronic acid (approximately 36.24 g, 241.6 mmol) and Cs$_2$CO$_3$ (approximately 196.8 g, 604.0 mmol) in DME (704 mL) and water (176 mL) were added. Pd(dppf)Cl$_2$ (approximately 8.839 g, 12.08 mmol) was added and the mixture was vigorously stirred under N$_2$ at 80° C. (reflux) for 1 h (no starting material remained). The reaction was cooled to ambient temperature and diluted with water (704 mL). The aqueous phase was separated and extracted with EtOAc (704 mL). The organic phase was washed with 700 mL of brine, dried over MgSO$_4$, filtered and concentrated in vacuo. The crude product was chromatographed on a 1500 g silica gel column eluting with 0-30% EtOAc/hexanes. The product fractions (eluted at 15% EtOAc) were combined and concentrated in vacuo affording tert-butyl N-tert-butoxycarbonyl-N-[4-chloro-6-(2,6-dimethylphenyl)pyrimidin-2-yl]carbamate (81.3 g, 78%) as a clear oil, which crystallized on standing. $^1$H NMR (400 MHz, DMSO-d$_6$) δ 7.88 (s, 1H), 7.30 (dd, J=8.2, 7.0 Hz, 1H), 7.21-7.16 (m, 2H), 2.03 (s, 6H), 1.38 (s, 18H). ESI-MS m/z calc. 433.17682, found 434.1 (M+1)$^+$; Retention time: 2.32 minutes (LC method A).

Synthesis of 4-Chloro-6-(2,6-dimethylphenyl)pyrimidin-2-amine (hydrochloride salt) (7·HCl)

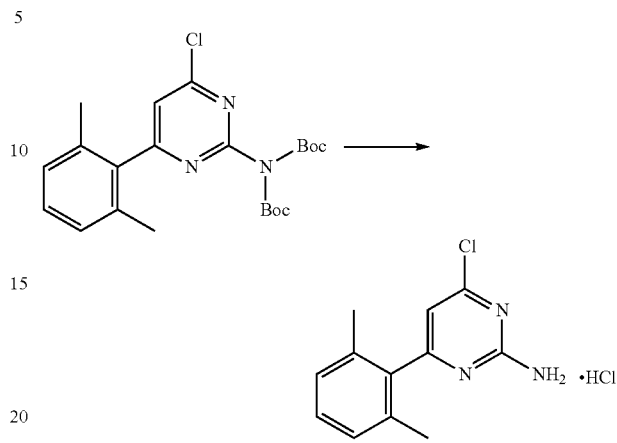

tert-Butyl N-tert-butoxycarbonyl-N-[4-chloro-6-(2,6-dimethylphenyl) pyrimidin-2-yl]carbamate (514.8 g, 915.9 mmol) was dissolved in dichloromethane (4 L). Hydrogen chloride in p-dioxane (1 L, 4 mol) was added and the mixture was stirred overnight at ambient temperature. The resulting precipitate was collected by vacuum filtration and dried in vacuo to obtain 4-chloro-6-(2,6-dimethylphenyl) pyrimidin-2-amine hydrochloride (213.5 g, 64%) as a white solid (213.5 g, 82%). $^1$H NMR (250 MHz, DMSO-d$_6$) δ 7.45-6.91 (m, 3H), 6.73 (s, 1H), 2.08 (s, 6H). ESI-MS m/z calc. 233.072, found 234.1 (M+1)$^+$; Retention time: 2.1 minutes (LC Method C).

Synthesis of 4-Chloro-6-(2,6-dimethylphenyl)pyrimidin-2-amine (7)

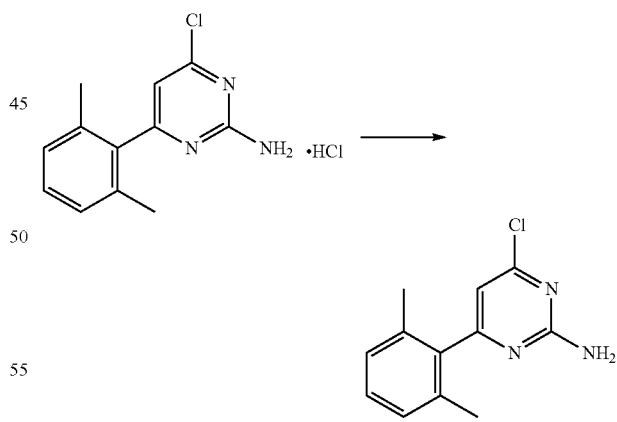

4-Chloro-6-(2,6-dimethylphenyl)pyrimidin-2-amine (Hydrochloride salt) (166 g, 614.5 mmol) and 4-chloro-6-(2,6-dimethylphenyl)pyrimidin-2-amine (Hydrochloride salt) (30 g, 111.0 mmol) were suspended in DCM (2.5 L), treated with NaOH (725 mL of 1 M, 725.0 mmol) and stirred at ambient temperature for 1 h. The mixture was transferred into a separatory funnel and left standing overnight. The DCM phase was separated and the aqueous phase with insoluble material was extracted twice more with DCM (2×500 ml). The combined brown DCM phases were stirred with magnesium sulfate and charcoal for 1 h, filtered and the yellow solution concentrated to a volume of ~500 mL. The solution was diluted with heptane (750 mL) and DCM was removed under reduced pressure at 60° C. to give a cream suspension. It was stirred at ambient temperature for 1 h, filtered, washed with cold heptane and dried to give 4-chloro-6-(2,6-dimethylphenyl)pyrimidin-2-amine (157 g, 91%) as a cream solid.

$^1$H NMR (400 MHz, DMSO-$d_6$) δ 7.28-7.14 (m, 3H), 7.10 (d, J=7.5 Hz, 2H), 6.63 (s, 1H), 2.06 (s, 6H). ESI-MS m/z calc. 233.07198, found 234.0 (M+1)$^+$; Retention time: 1.45 minutes (LC method A).

Synthesis of 3-[[4-Chloro-6-(2,6-dimethylphenyl) pyrimidin-2-yl]sulfamoyl]benzoic acid (8)

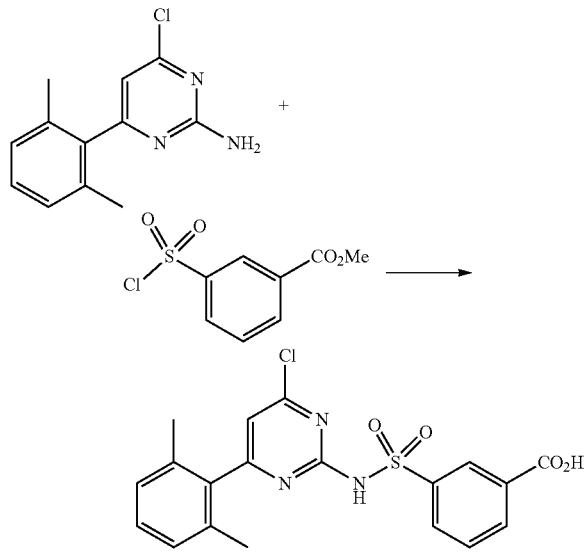

4-Chloro-6-(2,6-dimethylphenyl)pyrimidin-2-amine (235 g, 985.5 mmol) was dissolved in MeTHF (2.3 L) and cooled in an ice bath under stirring and nitrogen. To the cold solution methyl 3-chlorosulfonylbenzoate (347 g, 1.479 mol) was added in one portion (seems slightly endothermic) and to the cold pale yellow solution a solution of 2-methyl-butan-2-ol (Lithium salt) (875 mL of 3.1 M, 2.712 mol) (in heptane) was added dropwise over 1.25 h (exothermic, internal temperature from 0° C. to 10° C.). The ice bath was removed and the greenish solution was stirred for 4 h at ambient temperature. To the greenish solution cold HCl (2 L of 1.5 M, 3.000 mol) was added, the phases separated and the organic phase was washed once with water (1 L) and once with brine (500 mL). The aqueous phases were back extracted once with MeTHF (350 mL) and the organic phases were combined. This yellow MeTHF solution of methyl 3-[[4-chloro-6-(2,6-dimethylphenyl)pyrimidin-2-yl]sulfamoyl]benzoate (ESI-MS m/z calc. 431.07065, found 432.0 (M+1)$^+$; Retention time: 1.81 minutes) was treated with NaOH (2.3 L of 2 M, 4.600 mol) and stirred at ambient temperature for 1 h. The phases were separated and the NaOH phase was washed twice with MeTHF (2×500 mL) and the combined organic phases were extracted once with 2M NaOH (1×250 mL).

The combined NaOH phases were combined, stirred in an ice bath and slowly acidified by addition of HCl (416 mL of 36% w/w, 4.929 mol) while keeping the internal temperature between 10 and 20° C. At the end of the addition (pH ~5-6) the final pH was adjusted to 2-3 by addition of solid citric acid. The formed yellow tacky suspension was stirred at ambient temperature over night to give a cream crisp suspension. The solid was collected by filtration, washed with plenty of water and sucked dry for 3 h. The solid was dried under reduced pressure with a nitrogen leak at 45-50° C. for 120 h. 3-[[4-chloro-6-(2,6-dimethylphenyl)pyrimidin-2-yl]sulfamoyl]benzoic acid (395 g, 96%) was isolated as an off-white solid. $^1$H NMR (400 MHz, DMSO-$d_6$) δ 13.44 (s, 1H), 12.46 (s, 1H), 8.48-8.39 (m, 1H), 8.25-8.15 (m, 1H), 8.15-8.08 (m, 1H), 7.68 (t, J=7.8 Hz, 1H), 7.31 (s, 1H), 7.28-7.18 (m, 1H), 7.10 (d, J=7.6 Hz, 2H), 1.84 (s, 6H). ESI-MS m/z calc. 417.055, found 418.0 (M+1)$^+$; Retention time: 1.56 minutes. (LC method A).

Synthesis of (11R)-6-(2,6-Dimethylphenyl)-11-(2-methylpropyl)-12-{spiro[2.3]hexan-5-yl}-9-oxa-2$\lambda^6$-thia-3,5,12,19-tetraazatricyclo[12.3.1.1$^{4,8}$]-nonadeca-1(17),4(19),5,7,14(18),15-hexaene-2,2,13-trione (Compound I)

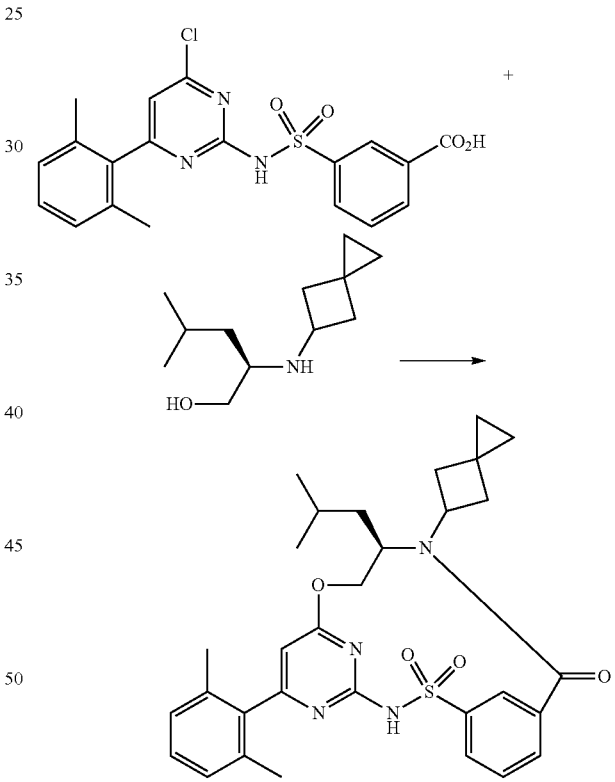

(2R)-4-Methyl-2-(spiro[2.3]hexan-5-ylamino)pentan-1-ol (1.42 g, 7.197 mmol), 3-[[4-chloro-6-(2,6-dimethylphenyl)pyrimidin-2-yl]sulfamoyl]benzoic acid (3.077 g, 7.209 mmol), and sodium tert-butoxide (2.731 g, 28.42 mmol) were combined in THF (25 mL) and stirred at ambient temperature for 1 h (slight exotherm). After 1 h, the reaction mixture was added dropwise to a stirred solution of HATU (5.436 g, 14.30 mmol) in DMF (50 mL). The reaction was stirred an additional 16 h at ambient temperature. The reaction was evaporated to an oil. The resulting oil was partitioned between ethyl acetate (100 mL) and a 1M HCl solution (100 mL). The organics were separated, washed with additional 1M HCl (100 mL), then brine (100 mL). The organics were dried over sodium sulfate and evaporated.

The crude product was purified by silica gel chromatography eluting with 0-80% ethyl acetate in hexanes to give amorphous (11R)-6-(2,6-dimethylphenyl)-11-(2-methylpropyl)-12-{spiro[2.3]hexan-5-yl}-9-oxa-2$\lambda^6$-thia-3,5,12,19-tetraazatricyclo[12.3.1.1$^{4,8}$]nonadeca-1(17),4(19),5,7,14(18), 15-hexaene-2,2,13-trione (1.73 g, 42%). $^1$H NMR (400 MHz, DMSO-d$_6$) δ 13.07 (s, 1H), 8.40 (s, 1H), 7.96-7.85 (m, 1H), 7.77-7.60 (m, 2H), 7.30-7.20 (m, 1H), 7.12 (d, J=7.6 Hz, 2H), 6.38 (s, 1H), 5.12 (dd, J=10.6, 4.2 Hz, 1H), 4.40 (t, J=11.1 Hz, 1H), 4.23 (p, J=8.5 Hz, 1H), 3.78-3.66 (m, 1H), 3.31-3.22 (m, 2H), 2.23-1.83 (m, 8H), 1.72-1.60 (m, 1H), 1.30 (s, 1H), 1.20-1.10 (m, 1H), 0.73 (d, J=6.7 Hz, 3H), 0.56-0.41 (m, 4H), 0.21 (d, J=6.3 Hz, 3H). ESI-MS m/z calc. 560.2457, found 561.4 (M+1)$^+$; Retention time: 2.01 minutes (LC method A).

Alternative Synthesis of Compound I

Synthesis of 3-[[4-(2,6-Dimethylphenyl)-6-[(2R)-4-methyl-2-(spiro[2.3]hexan-5-ylamino) pentoxy]pyrimidin-2-yl]sulfamoyl]benzoic acid (Hydrochloride Salt) (9)

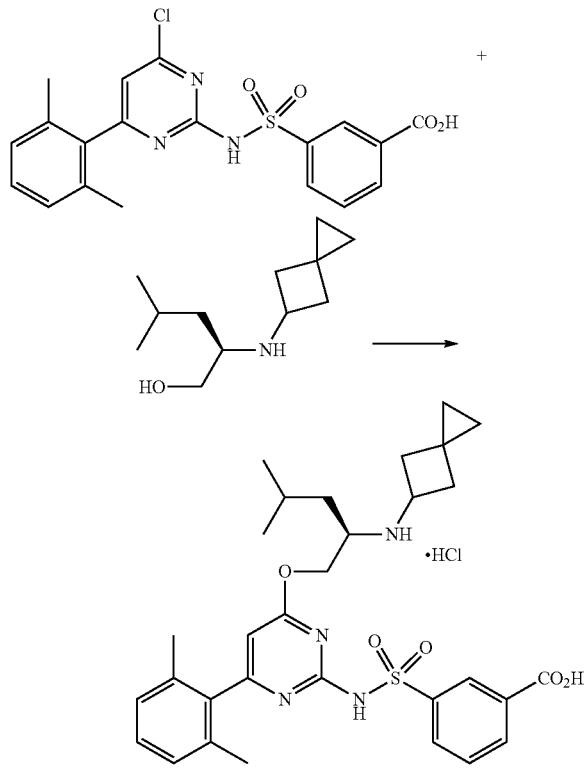

To a solution of (2R)-4-methyl-2-(spiro[2.3]hexan-5-ylamino)pentan-1-ol (52.26 g, 264.9 mmol) and 3-[[4-chloro-6-(2,6-dimethylphenyl)pyrimidin-2-yl]sulfamoyl]benzoic acid (103 g, 242.8 mmol) in MeTHF (700 mL) was added sodium tert-butoxide (93.4 g, 971.9 mmol) portionwise keeping the reaction temperature <40° C. The addition is exothermic and the reaction temperature was controlled using an ice-water bath and addition rate of the base. The reaction was stirred for 2 h at ambient temperature. The reaction was quenched with the slow addition of HCl (1.2 L of 1 M, 1.200 mol) and stirred for 5 min. The mixture was transferred to a separatory funnel using MeTHF. The aqueous phase was separated and extracted with 250 mL of MeTHF. The combined organic phases were washed with 500 mL of brine, dried over MgSO$_4$, filtered and concentrated in vacuo. The light yellow solid was slurried with EtOAc (200 mL) and stirred for 1 h. The solid was collected using a M frit and washing 3× with 10 mL of EtOAc. The off-white solid was air dried and dried in vacuo for 20 h to afford 3-[[4-(2,6-dimethylphenyl)-6-[(2R)-4-methyl-2-(spiro[2.3]hexan-5-ylamino)pentoxy]pyrimidin-2-yl]sulfamoyl]benzoic acid (Hydrochloride salt) (120 g, 76%). ESI-MS m/z calc. 578.2563, found 579.2 (M+1)$^+$; Retention time: 1.02 minutes. (LC method A).

Synthesis of (11R)-6-(2,6-Dimethylphenyl)-11-(2-methylpropyl)-12-{spiro[2.3]hexan-5-yl}-9-oxa-2$\lambda^6$-thia-3,5,12,19-tetraazatricyclo[12.3.1.1$^{4,8}$]nonadeca-1(17),4(19),5,7,14(18),15-hexaene-2,2,13-trione (Compound I)

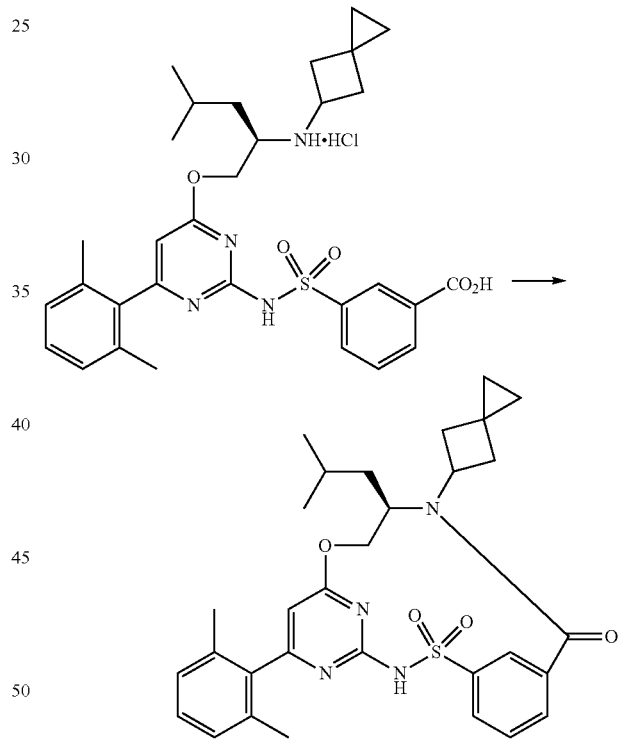

3-[[4-(2,6-Dimethylphenyl)-6-[(2R)-4-methyl-2-(spiro[2.3]hexan-5-ylamino)pentoxy]pyrimidin-2-yl]sulfamoyl]benzoic acid (Hydrochloride salt) (4.41 g, 7.169 mmol) and HATU (2.80 g, 7.364 mmol) were combined in DMF (100 mL) and triethylamine (3.0 mL, 21.52 mmol) was added. The reaction was stirred at ambient temperature for 5 h. The reaction mixture was poured into a stirred solution of water (150 mL) and HCl (35 mL of 1 M, 35.00 mmol). The mixture was stirred for 20 min and the resulting white solid was collected by filtration. The solid was dissolved in ethyl acetate (100 mL) and washed with 1M HCl (100 mL), brine (100 mL), then dried over sodium sulfate and evaporated. The crude product was purified by silica gel chromatography eluting with 0-70% ethyl acetate in hexanes to give amorphous (11R)-6-(2,6-dimethylphenyl)-11-(2-methylpropyl)-12-{spiro[2.3]hexan-5-yl}-9-oxa-2λ⁶-thia-3,5,12,19-tetraazatricyclo[12.3.1.1⁴,⁸]nonadeca-1(17),4(19),5,7,14(18),15-hexaene-2,2,13-trione (2.94 g, 73%). ¹H NMR (400 MHz, DMSO-d₆) δ 13.07 (s, 1H), 8.40 (s, 1H), 7.91 (broad s, 1H), 7.68 (broad s, 2H), 7.25 (t, J=7.9 Hz, 1H), 7.12 (d, J=7.4 Hz, 2H), 6.38 (s, 1H), 5.12 (dd, J=10.7, 4.2 Hz, 1H), 4.40 (t, J=11.1 Hz, 1H), 4.23 (p, J=8.5 Hz, 1H), 3.79-3.65 (m, 1H), 3.31-3.22 (m, 2H), 2.21-1.84 (m, 8H), 1.72-1.61 (m, 1H), 1.36-1.23 (m, 1H), 1.21-1.10 (m, 1H), 0.73 (d, J=6.6 Hz, 3H), 0.55-0.41 (m, 4H), 0.21 (d, J=6.2 Hz, 3H). ESI-MS m/z calc. 560.2457, found 561.5 (M+1)⁺; Retention time: 2.02 minutes (LC method A).

Salts of Compound I were prepared according to the following Examples.

Example 2: Synthesis of a Potassium Salt of Compound I (11R)-6-(2,6-Dimethylphenyl)-11-(2-methylpropyl)-12-{spiro[2.3]hexan-5-yl}-9-oxa-2λ⁶-thia-3,5,12,19-tetraazatricyclo[12.3.1.1⁴,⁸]nonadeca-1(17),4(19),5,7,14(18),15-hexaene-2,2,13-trione (2 g, 3.448 mmol) was dissolved in methanol (20 mL) and slowly treated with KOH (6.896 mL of 0.5 M, 3.448 mmol) (in methanol) under stirring. The clear solution was stirred at ambient temperature for 1 h, evaporated to give a glass and dried under house vacuum with nitrogen leak at 50-55° C. for 16 h to give amorphous (11R)-6-(2,6-dimethylphenyl)-11-(2-methylpropyl)-12-{spiro[2.3]hexan-5-yl}-9-oxa-2λ⁶-thia-3,5,12,19-tetraazatricyclo[12.3.1.1⁴,⁸]-nonadeca-1(17),4(19),5,7,14(18),15-hexaene-2,2,13-trione (Potassium Ion) (2.033 g, 98%) as an off-white solid. ¹H NMR (500 MHz, DMSO-d₆) δ 8.40 (s, 1H), 7.82-7.74 (m, 1H), 7.53-7.46 (m, 2H), 7.12 (t, J=7.5 Hz, 1H), 7.03 (d, J=7.6 Hz, 2H), 5.78 (s, 1H), 5.09 (dd, J=10.5, 4.3 Hz, 1H), 4.17 (p, J=8.6 Hz, 1H), 4.06 (t, J=11.0 Hz, 1H), 3.88 (dq, J=11.1, 7.3, 5.5 Hz, 1H), 3.28 (dt, J=14.5, 9.3 Hz, 2H), 2.07 (dt, J=24.5, 9.2 Hz, 2H), 1.96 (s, 6H), 1.58 (ddd, J=14.0, 10.9, 2.8 Hz, 1H), 1.29 (ddt, J=13.3, 6.9, 2.8 Hz, 1H), 1.17 (ddd, J=13.7, 10.6, 2.9 Hz, 1H), 0.71 (d, J=6.6 Hz, 3H), 0.52 (dd, J=8.3, 5.6 Hz, 2H), 0.50-0.40 (m, 2H), 0.21 (d, J=6.4 Hz, 3H).

Example 3: Synthesis of a Sodium Salt of Compound I

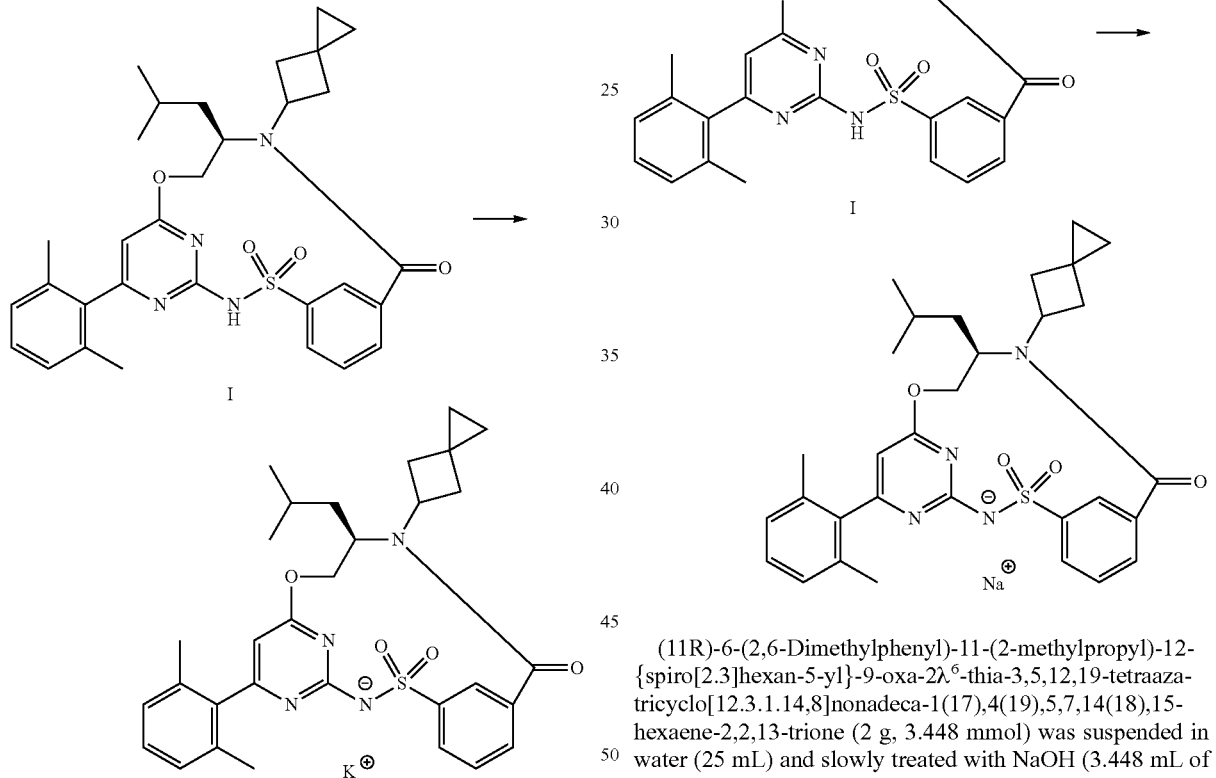

(11R)-6-(2,6-Dimethylphenyl)-11-(2-methylpropyl)-12-{spiro[2.3]hexan-5-yl}-9-oxa-2λ⁶-thia-3,5,12,19-tetraazatricyclo[12.3.1.1⁴,⁸]nonadeca-1(17),4(19),5,7,14(18),15-hexaene-2,2,13-trione (2 g, 3.448 mmol) was suspended in water (25 mL) and slowly treated with NaOH (3.448 mL of 1 M, 3.448 mmol) under stirring. The suspension was stirred at ambient temperature for 1.25 h to give a cloudy solution. The cloudy solution was filtered clear over a syringe filter (0.2 μm) and the clear colorless filtrate was lyophilized for two days to give amorphous (11R)-6-(2,6-Dimethylphenyl)-11-(2-methylpropyl)-12-{spiro[2.3]hexan-5-yl}-9-oxa-2λ⁶-thia-3,5,12,19-tetraazatricyclo[12.3.1.1⁴,⁸]nonadeca-1(17),4(19),5,7,14(18),15-hexaene-2,2,13-trione (Sodium salt) (2 g, 99%) as a colorless fluffy solid. ¹H NMR (500 MHz, DMSO-d₆) δ 8.40 (s, 1H), 7.78 (ddd, J=5.6, 3.5, 1.6 Hz, 1H), 7.52-7.45 (m, 2H), 7.12 (t, J=7.5 Hz, 1H), 7.02 (d, J=7.6 Hz, 2H), 5.77 (s, 1H), 5.09 (dd, J=10.5, 4.3 Hz, 1H), 4.16 (p, J=8.5 Hz, 1H), 4.06 (t, J=10.9 Hz, 1H), 3.89 (dq, J=11.3, 7.5, 5.6 Hz, 1H), 3.28 (dt, J=14.5, 9.3 Hz, 2H), 2.07 (dt, J=24.7, 9.3 Hz, 2H), 1.96 (s, 6H), 1.58 (td, J=11.3, 10.8, 5.7 Hz, 1H), 1.28 (ddd, J=9.6, 6.5, 3.0 Hz, 1H), 1.17 (ddd, J=13.6, 10.5, 2.8 Hz, 1H), 0.71 (d, J=6.6 Hz, 3H), 0.52 (dd, J=8.3, 5.6 Hz, 2H), 0.50-0.41 (m, 2H), 0.21 (d, J=6.4 Hz, 3H).

Example 4: Synthesis of a Calcium Salt of Compound I

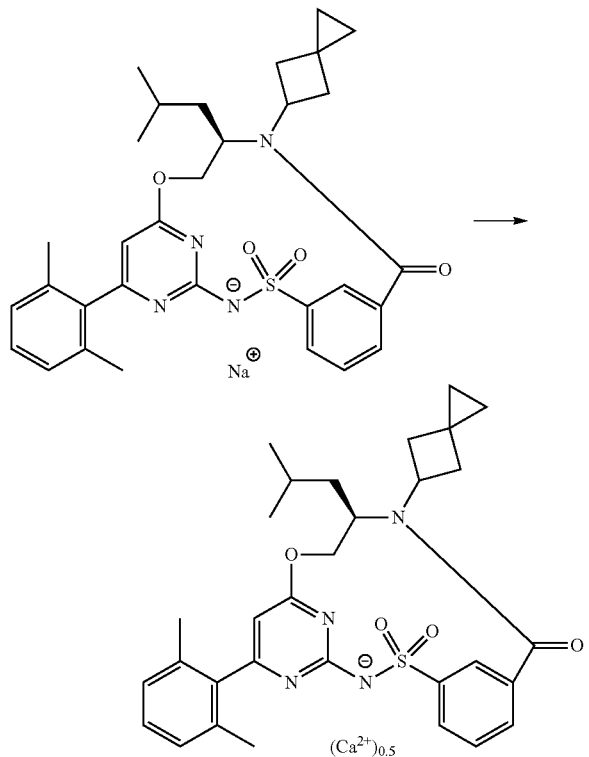

(11R)-6-(2,6-Dimethylphenyl)-11-(2-methylpropyl)-12-{spiro[2.3]hexan-5-yl}-9-oxa-2λ⁶-thia-3,5,12,19-tetraazatricyclo[12.3.1.14,8]nonadeca-1(17),4(19),5,7,14(18),15-hexaene-2,2,13-trione (Sodium salt) (500 mg, 0.8566 mmol) was stirred in water (5 mL) for 10 min to give a clear solution. A solution of CaCl₂ (46.8 mg, 0.4217 mmol) in water (0.5 mL) was added resulting in the precipitation of a gelatinous solid to give a semi-solid mass. Another portion of water (5 mL) was added and the suspension stirred at ambient temperature for 23 h. The solid was collected by filtration, washed with plenty of water (~3×5-10 mL) and dried under vacuum with a nitrogen bleed at 55-60° C. for 14 h to give amorphous (11R)-6-(2,6-dimethylphenyl)-11-(2-methylpropyl)-12-{spiro[2.3]hexan-5-yl}-9-oxa-2λ⁶-thia-3,5,12,19-tetraazatricyclo-[12.3.1.14,8]nonadeca-1(17),4(19),5,7,14(18),15-hexaene-2,2,13-trione (Calcium salt (0.5)) (423 mg, 85%) as an off white solid. ¹H NMR (500 MHz, DMSO-d₆) δ 8.40 (s, 1H), 7.78 (td, J=4.4, 1.6 Hz, 1H), 7.50 (d, J=4.7 Hz, 2H), 7.13 (t, J=7.5 Hz, 1H), 7.03 (d, J=7.5 Hz, 2H), 5.81 (s, 1H), 5.09 (dd, J=10.5, 4.3 Hz, 1H), 4.17 (p, J=8.6 Hz, 1H), 4.08 (t, J=11.0 Hz, 1H), 3.87 (dq, J=11.1, 7.3, 5.4 Hz, 1H), 3.28 (dt, J=14.2, 9.3 Hz, 2H), 2.07 (dt, J=24.3, 9.1 Hz, 2H), 1.99-1.95 (m, 6H), 1.59 (ddd, J=14.0, 10.8, 2.8 Hz, 1H), 1.28 (tt, J=6.4, 3.0 Hz, 1H), 1.17 (ddd, J=13.6, 10.4, 2.8 Hz, 1H), 0.71 (d, J=6.6 Hz, 3H), 0.55-0.40 (m, 4H), 0.21 (d, J=6.4 Hz, 3H).

ESI-MS m/z calc. 560.2457, found 561.0 (M+1)⁺; Retention time: 2.1 minutes (LC method A).

Example 5: Synthesis of (11R)-6-(2,6-Dimethylphenyl)-11-(2-methylpropyl)-12-[(1,1,2,2-tetradeutero) spiro[2.3]hexan-5-yl]-9-oxa-22λ⁶-thia-3,5,12,19-tetraazatricyclo[12.3.1.14,8]nonadeca-1(17),4(19),5,7,14(18),15-hexaene-2,2,13-trione (Compound Ia)

Synthesis of [2-Bromo-1-(bromomethyl)ethoxy] methylbenzene (11)

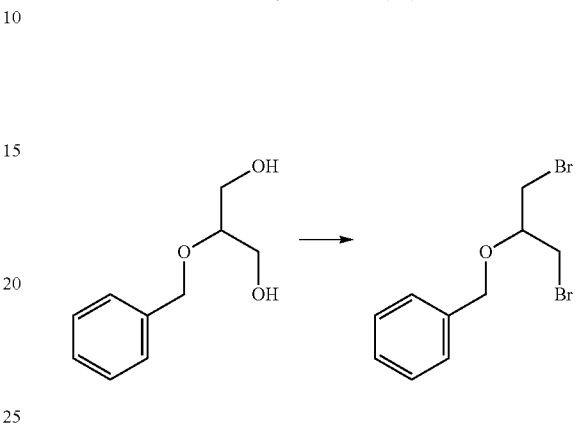

To a solution of 2-benzyloxypropane-1,3-diol (24.3 g, 129.36 mmol) in anhydrous CH₂Cl₂ (350 mL) under argon atmosphere at 0° C. was added Ph₃P (72.177 g, 272.43 mmol) followed by CBr₄ (91.258 g, 272.43 mmol) (one portion addition caused a huge gas generation). The reaction mixture was stirred at 0° C. for 2.5 h. To the reaction mixture was added water (150 mL) and dichloromethane (600 mL). The organic layer was separated, dried over sodium sulfate, filtered and concentrated under reduced pressure. Then, 10% ether in hexane (500 mL) was added, sonicated and filtered. The solid cake was washed with 10% ether in hexane (300 mL). The solid was discarded and the combined filtrates were concentrated under reduced pressure to give the crude product. The crude product was purified by flash chromatography (loaded in CH₂Cl₂) (330 g SiO₂, eluting 0 to 4% ether in hexane) to afford [2-bromo-1-(bromomethyl) ethoxy]methylbenzene (23.39 g, 59%) as a colorless liquid. ¹H NMR (500 MHz, Chloroform-d) δ 7.49-7.30 (m, 5H), 4.70 (s, 2H), 3.83 (p, J=5.2 Hz, 1H), 3.60 (d, J=5.2 Hz, 4H). ESI-MS m/z calc. 305.92548, NO MS was observed. Retention time: 5.47 minutes (LC Method C).

Synthesis of Diisopropyl 3-benzyloxycyclobutane-1,1-dicarboxylate (12)

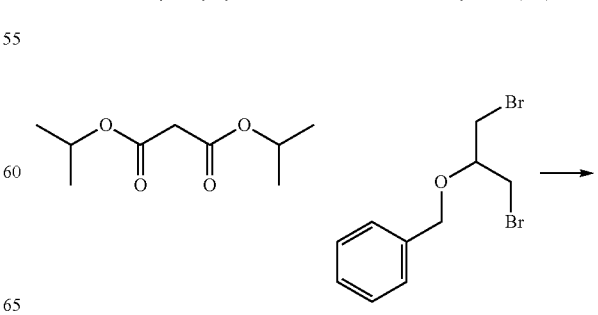

-continued

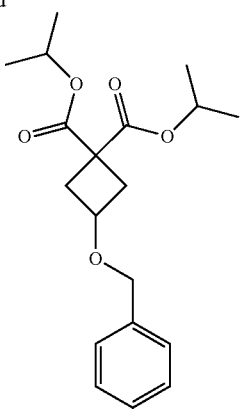

NaH (6.42 g, 160.52 mmol, 60% oil suspension) was suspended in dry DMF (280 mL) under Argon. Diisopropyl propanedioate (26.49 g, 26.731 mL, 139.33 mmol) in anhydrous DMF (20 mL) was added dropwise while keeping the temperature around 20° C. On cessation of gas evolution, [2-bromo-1-(bromomethyl)ethoxy]-methylbenzene (21.334 g, 69.264 mmol) in anhydrous DMF (20 mL) was added. The reaction mixture was stirred at 140° C. for 26 h before being cooled to ambient temperature and poured into a saturated aqueous solution of NH$_4$Cl (500 mL) to prevent emulsion formation. The solution was extracted with hexane (3×500 mL), washed with water (300 mL), brine (300 mL), dried over anhydrous Na$_2$SO$_4$, filtered and concentrated under reduced pressure to remove hexane. The crude product obtained was purified by flash chromatography (loaded in hexane) (330 g SiO$_2$, eluting 0 to 15% ether in hexane) to afford diisopropyl 3-benzyloxycyclobutane-1,1-dicarboxylate (26.84 g, 90%) as a colorless liquid. Note: The product contained 22% of diisopropyl propanedioate. $^1$H NMR (250 MHz, CDCl$_3$) δ 7.58-7.14 (m, 5H), 5.22-4.90 (m, 2H), 4.43 (s, 2H), 4.15 (p, J=7.2 Hz, 1H), 2.89-2.68 (m, 2H), 2.63-2.40 (m, 2H), 1.43-0.99 (m, 12H). ESI-MS m/z calc. 334.178, found 335.3 (M+1)$^+$; Retention time: 5.94 minutes (LC Method C).

Synthesis of [3-Benzyloxy-1-[dideuterio(hydroxy)methyl]cyclobutyl]-dideuterio-methanol (13)

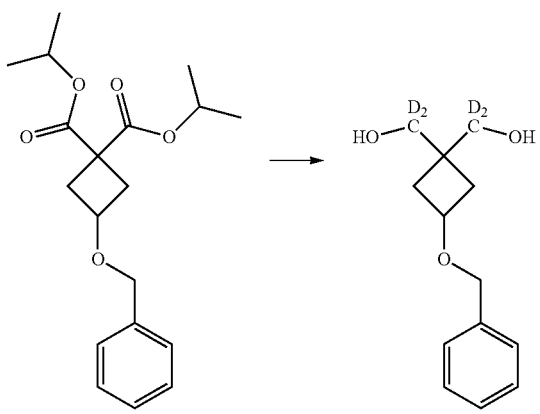

To a solution of diisopropyl 3-benzyloxycyclobutane-1,1-dicarboxylate (26.84 g, 62.604 mmol) in anhydrous THF (250 mL) at 0° C. was added lithium tetradeuterioalumanuide (6.11 g, 145.55 mmol) portion by portion. After the addition was competed, the reaction was stirred at ambient temperature for 2 days before being re-cooled to 0° C. Water (6.2 mL) was added dropwise followed by 15% aqueous sodium hydroxide (6.2 mL) and water (18.6 mL). The resulting solution was stirred at ambient temperature for 30 min before being filtered through Celite and washed with THF. The filtrate was concentrated under reduced pressure.

The residue obtained was dissolved in ethyl acetate (450 mL), washed with water (100 mL×3) and brine (100 mL). The organic layer was separated, and the aqueous layer was extracted with ether (3×150 mL). The combined organic layers were dried over anhydrous magnesium sulfate, filtered, and concentrated under reduced pressure to afford a crude white solid. The crude product was purified by flash chromatography (loaded in CH$_2$Cl$_2$) (330 g SiO$_2$, eluting 0 to 50% acetone in hexane) to afford [3-benzyloxy-1-[dideuterio(hydroxy)methyl]cyclobutyl]-dideuterio-methanol (9.95 g, 68%) as a white solid. $^1$H NMR (500 MHz, Chloroform-d) δ 7.40-7.32 (m, 4H), 7.32-7.28 (m, 1H), 4.42 (s, 2H), 4.17-3.99 (m, 1H), 2.48-2.05 (m, 4H), 1.87-1.79 (m, 2H). ESI-MS m/z calc. 226.1507, found 227.4 (M+1)$^+$, retention time 2.94 minutes (LC Method C).

Synthesis of [3,3-Bis[dideuterio(iodo)methyl]cyclobutoxy]-methylbenzene (14)

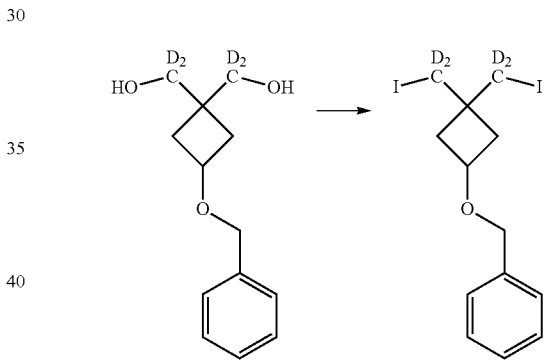

To a solution of [3-benzyloxy-1-[dideuterio(hydroxy)methyl]-cyclobutyl]-dideuterio-methanol (9.95 g, 43.967 mmol) in anhydrous CH$_2$Cl$_2$ (420 mL) was added Et$_3$N (17.860 g, 24.6 mL, 176.50 mmol), then cooled to 0° C. Methanesulfonyl chloride (14.652 g, 9.9 mL, 127.91 mmol) was added dropwise, and the resulting solution was stirred at this temperature for 2 h before being quenched with saturated sodium bicarbonate solution (200 mL). Dichloromethane (400 mL) was added; the organic layer was separated, washed with brine (150 mL), dried over anhydrous magnesium sulfate, filtered and concentrated under reduced pressure. The residue obtained was placed under high vacuum to afford the bis-mesylate intermediate as a pale yellow liquid. The bis-mesylate was dissolved in anhydrous acetone (300 mL), and NaI (49.08 g, 327.43 mmol) was added. The reaction solution was heated at 50° C. for 5 days. The reaction solution was filtered and washed with acetone.

The filtrate was concentrated under reduced pressure. To the residue obtained was added ether (800 mL) and a 10% sodium sulfite solution (250 mL×2). The organic solution was separated, dried over anhydrous sodium sulfate, filtered, and concentrated under reduced pressure. The crude product was purified by flash chromatography (loaded in CH$_2$Cl$_2$) (330 g SiO$_2$, eluting 0 to 5% ether in hexane) to afford [3,3-bis[dideuterio(iodo)methyl]cyclobutoxy]methylbenzene (15.813 g, 81%) as a pale yellow oil. $^1$H NMR (500 MHz, Chloroform-d) δ 7.42-7.28 (m, 5H), 4.42 (s, 2H), 3.93 (tt, J=7.2, 6.1 Hz, 1H), 2.40-2.23 (m, 2H), 2.07-1.92 (m, 2H).

ESI-MS m/z calc. 445.9542, found 464.3 (M+18)$^+$; Retention time: 6.53 minutes (LC Method C).

Synthesis of 5-Benzyloxy-1,1,2,2-tetradeuterio-spiro[2.3]hexane (15)

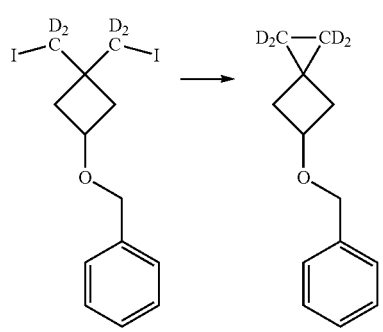

To a solution of [3,3-bis[dideuterio(iodo)methyl]cyclobutoxy]-methylbenzene (15.81 g, 35.441 mmol) in a mixture of ethanol (70 mL) and water (30 mL) was added Zn (9.96 g, 152.32 mmol). The resulting solution was refluxed for 2 h. The reaction solution was cooled to ambient temperature, and then diluted with dichloromethane (400 mL) and water (100 mL). The organic layer was separated, washed with brine, dried over anhydrous magnesium sulfate, filtered, and concentrated under reduced pressure. The crude product was purified by flash chromatography (loaded in CH$_2$Cl$_2$) (220 g SiO$_2$, eluting 0 to 4% ether in hexane) to afford 5-benzyloxy-1,1,2,2-tetradeuterio-spiro[2.3]hexane (6.77 g, 94%) as a colorless oil. $^1$H NMR (250 MHz, CDCl$_3$) δ 7.60-7.09 (m, 5H), 4.45 (s, 2H), 4.30 (p, J=6.9 Hz, 1H), 2.41-2.22 (m, 2H), 2.22-1.99 (m, 2H). ESI-MS m/z calc. 192.14522, no MS was observed. Retention time: 5.62 minutes (LC Method C).

Synthesis of 1,1,2,2-Tetradeuteriospiro[2.3]hexan-5-ol (16)

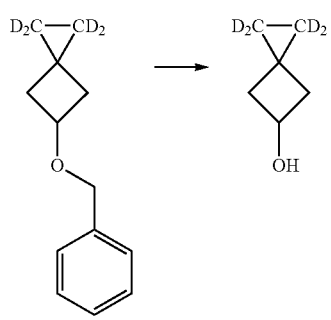

To a solution of 5-benzyloxy-1,1,2,2-tetradeuterio-spiro[2.3]hexane (6.58 g, 34.219 mmol) in methyl acetate (35 mL) was added 5% Pd/C (1.01 g, 9.4907 mmol), and the mixture was stirred under hydrogen atmosphere for 20 h. Another 5% Pd/C (0.51 g, 4.7923 mmol) amount was added to the reaction mixture, and it was stirred under a hydrogen atmosphere for another 20 h. The catalyst was filtered off and rinsed with diethyl ether (30 ml). The solvent was distilled off slowly at atmospheric pressure. The residue was distilled under vacuum (Bp$_{20}$=72° C.) to give 1,1,2,2-tetradeuteriospiro[2.3]hexan-5-ol (3.18 g, 91%) as a clear liquid.

$^1$H NMR (250 MHz, CDCl$_3$) δ 4.53 (q, J=6.5 Hz, 1H), 2.28-2.19 (m, 4H), 1.72 (d, J=5.7 Hz, 1H).

Synthesis of 1,1,2,2-Tetradeuteriospiro[2.3]hexan-5-one (17)

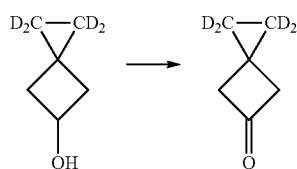

CrO$_3$/pyridine complex was obtained by adding CrO$_3$ (9.95 g, 99.506 mmol) in pyridine (95 mL). To this solution was added dropwise a solution of 1,1,2,2-tetradeuteriospiro[2.3]hexan-5-ol (3.16 g, 30.929 mmol) in pyridine (35 mL). The reaction mixture was stirred at ambient temperature for 21 h. After cooling down, water (50 mL) was added and then extracted with diethyl ether (200 mL×3). The organic phase was washed with 2N aqueous HCl until the aqueous phase reached pH=4, then washed with saturated aqueous NaHCO$_3$ (200 mL) and water (200 mL). After being dried over sodium sulfate, the solvent was slowly removed by distillation at atmospheric pressure. The residue was distilled (Bp$_{14}$=40-43° C.) to obtain 1,1,2,2-tetradeuteriospiro[2.3]hexan-5-one (2.36 g, 71%). $^1$H NMR (500 MHz, Chloroform-d) δ 3.16 (s, 4H).

Synthesis of 3-[[4-[(2R)-2-(tert-Butoxycarbonylamino)-4-methyl-pentoxy]-6-(2,6-dimethylphenyl)pyrimidin-2-yl]sulfamoyl]benzoic acid (18)

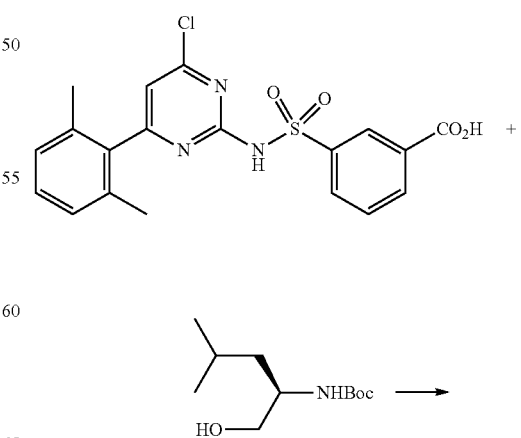

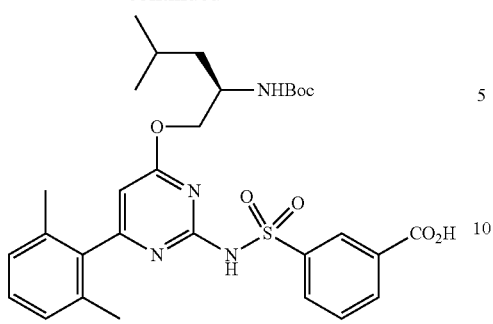

To a stirring solution of (2R)-2-amino-4-methyl-pentan-1-ol (12.419 g, 105.97 mmol) in anhydrous THF (200 mL) at ambient temperature under nitrogen was added sodium tert-butoxide (15.276 g, 158.95 mmol). The reaction mixture was stirred for 10 min and 3-[[4-chloro-6-(2,6-dimethylphenyl)pyrimidin-2-yl]sulfamoyl]benzoic acid (22.14 g, 52.983 mmol) was added. The reaction mixture was placed on a water bath preheated to 60° C. and stirred for 20 min. After cooling to ambient temperature, di-tert-butyl dicarbonate (69.381 g, 317.90 mmol) was added and the reaction mixture was stirred for 3 h. The reaction was quenched with saturated aqueous ammonium chloride (150 mL). Volatiles were removed under vacuum and the aqueous layer was acidified to pH ~3 with 10% aqueous citric acid. The product was extracted with ethyl acetate (3×200 mL). Combined organic layers were washed with brine (80 mL), dried over anhydrous sodium sulfate and concentrated to a residual volume of ~250 mL. The product was precipitated out into excess hexanes (750 mL) and collected by vacuum filtration. The obtained white solid was repurified by silica gel chromatography using 0-40% acetone (0.15% acetic acid buffer) gradient in hexanes (0.15% acetic acid buffer) to afford 3-[[4-[(2R)-2-(tert-butoxycarbonylamino)-4-methyl-pentoxy]-6-(2,6-dimethylphenyl)pyrimidin-2-yl]sulfamoyl]benzoic acid (20.73 g, 61%) as a white solid. ESI-MS m/z calc. 598.2461, found 599.4 (M+1)$^+$; Retention time: 5.85 minutes (LC Method C).

Synthesis of 3-[[4-[(2R)-2-Amino-4-methyl-pentoxy]-6-(2,6-dimethylphenyl)pyrimidin-2-yl]sulfamoyl]benzoic acid (Hydrochloride Salt) (19)

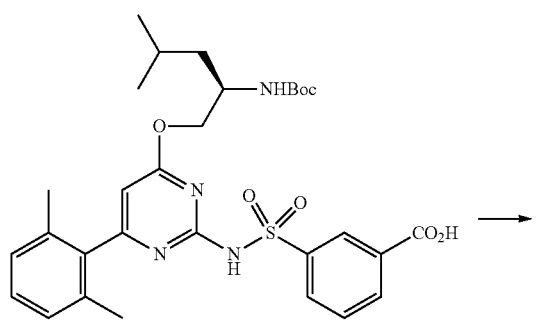

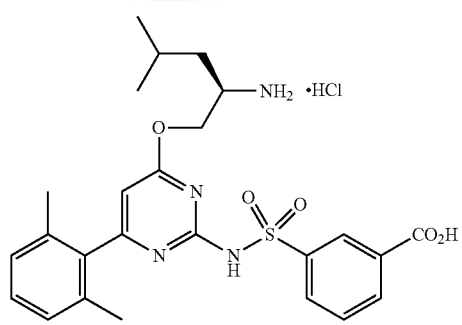

To a stirring solution of 3-[[4-[(2R)-2-(tert-butoxycarbonylamino)-4-methyl-pentoxy]-6-(2,6-dimethylphenyl)pyrimidin-2-yl]sulfamoyl]benzoic acid (20.73 g, 34.624 mmol) in DCM (200 mL) at ambient temperature was added HCl (87 mL of 4 M solution in 1,4-dioxane, 346.24 mmol). The reaction mixture was stirred for 2 h. Volatiles were removed under vacuum and the obtained solid was triturated with diethyl ether (150 mL). After removal of the volatiles, the product was dried under vacuum to afford 3-[[4-[(2R)-2-amino-4-methyl-pentoxy]-6-(2,6-dimethylphenyl)pyrimidin-2-yl]sulfamoyl]benzoic acid (hydrochloride salt) (19.68 g, 100%) as a white solid.

$^1$H NMR (250 MHz, DMSO-d$_6$) δ 8.56-8.27 (m, 4H), 8.14 (t, J=6.8 Hz, 2H), 7.70 (t, J=7.8 Hz, 1H), 7.34-7.18 (m, 1H), 7.17-7.02 (m, 2H), 6.31 (s, 1H), 4.42-4.23 (m, 1H), 4.23-4.06 (m, 1H), 3.5-3.4 (m, 1H, overlapped with water), 2.01 (s, 6H), 1.82-1.31 (m, 3H), 1.02-0.78 (m, 6H). ESI-MS m/z calc. 498.1937, found 499.3 (M+1)$^+$; Retention time: 1.63 minutes (LC Method B).

Synthesis of 3-[[4-(2,6-Dimethylphenyl)-6-[(2R)-4-methyl-2-[(1,1,2,2-tetradeuteriospiro[2.3]hexan-5-yl)amino]pentoxy]pyrimidin-2-yl]sulfamoyl]-benzoic acid (Hydrochloride Salt) (20)

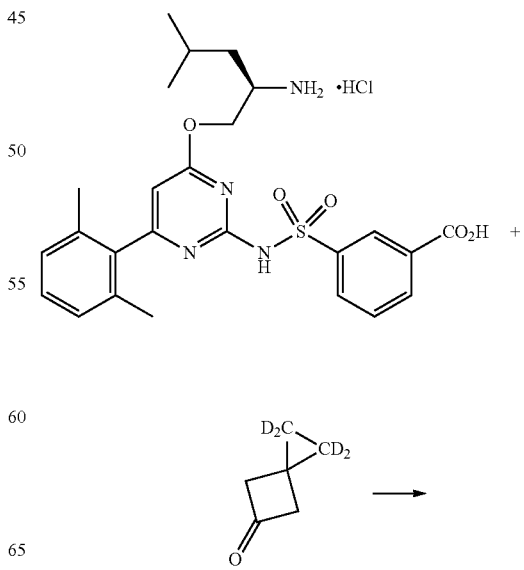

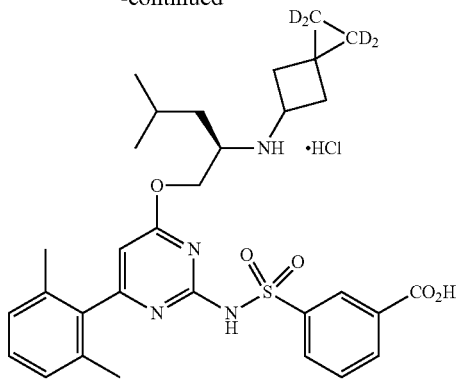

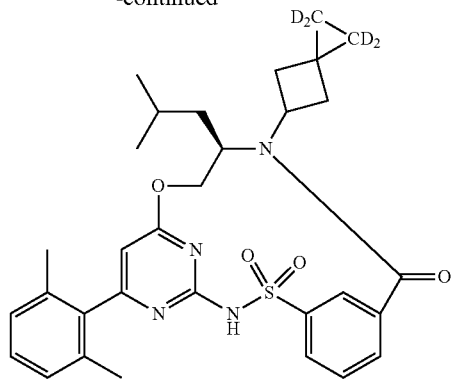

A 4 mL vial was charged with 3-[[4-[(2R)-2-amino-4-methyl-pentoxy]-6-(2,6-dimethylphenyl)pyrimidin-2-yl]sulfamoyl]benzoic acid (Hydrochloride salt) (100 mg, 0.1869 mmol), 1,1,2,2-tetradeuteriospiro[2.3]hexan-5-one (53 mg, 0.5292 mmol), anhydrous DCM (0.30 mL) and sodium acetoxyborohydride (Sodium salt) (133 mg, 0.6275 mmol). The vial was briefly purged with nitrogen and the mixture was stirred at ambient temperature for 1.5 h at which time LCMS showed 87% conversion. More borohydride (90 mg) was added and the mixture was stirred for an additional 30 min. A bit of methanol was added and the mixture was concentrated and dissolved in DMSO (total final volume 3 mL). The mixture was purified by reverse phase preparative HPLC (C18) using a gradient of acetonitrile in water (1 to 99% over 15 min) and HCl as a modifier. The pure fractions were collected and the solvents evaporated to give 3-[[4-(2,6-dimethylphenyl)-6-[(2R)-4-methyl-2-[(1,1,2,2-tetradeuteriospiro[2.3]hexan-5-yl)amino]pentoxy]pyrimidin-2-yl]sulfamoyl]benzoic acid (Hydrochloride salt) (93 mg, 80%) as a white solid. The product (94.5% pure, contains 5.5% of M+3=585.51 impurity) was used for the next step without any further purification. ESI-MS m/z calc. 582.2814, found 583.46 (M+1)+; Retention time: 1.27 minutes (LC method A).

Synthesis of (11R)-6-(2,6-Dimethylphenyl)-11-(2-methylpropyl)-12-[(1,1,2,2-tetradeutero)spiro[2.3]hexan-5-yl]-9-oxa-2$\lambda^6$-thia-3,5,12,19-tetraazatricyclo[12.3.1.1$^{4,8}$]nonadeca-1(17),4(19),5,7,14(18),15-hexaene-2,2,13-trione (Compound Ia)

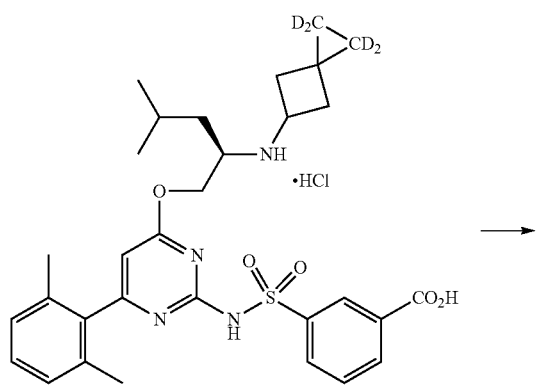

→

A 20 mL flask was charged under nitrogen with HATU (157 mg, 0.4129 mmol), anhydrous DMF (6 mL), and DIEA (0.15 mL, 0.8612 mmol). A solution of 3-[[4-(2,6-dimethylphenyl)-6-[(2R)-4-methyl-2-[(1,1,2,2-tetradeuteriospiro[2.3]hexan-5-yl)amino]pentoxy]pyrimidin-2-yl]sulfamoyl]benzoic acid (Hydrochloride salt) (93 mg, 0.1502 mmol) in anhydrous DMF (4 mL) was added dropwise through syringe over a period of 4 min. The mixture was stirred at ambient temperature for 17 h. The mixture was concentrated and diluted with DMSO (2 mL). The solution was microfiltered through a Whatman 0.45 µM PTFE syringe filter disc and purified by reverse phase preparative HPLC (C18) using a gradient of acetonitrile in water (1 to 99% over 15 min) and HCl as a modifier. Evaporation gave a residue that was triturated in DCM/hexanes. Evaporation of the solvents gave (11R)-6-(2,6-dimethylphenyl)-11-(2-methylpropyl)-12-[(1,1,2,2-tetradeutero)spiro[2.3]hexan-5-yl]-9-oxa-2$\lambda^6$-thia-3,5,12,19-tetraazatricyclo[12.3.1.1$^{4,8}$]nonadeca-1(17),4(19),5,7,14(18),15-hexaene-2,2,13-trione (48 mg, 54%) as an off-white solid. $^1$H NMR (500 MHz, DMSO-$d_6$) δ 13.01 (broad s, 1H), 8.41 (s, 1H), 7.92 (d, J=7.5 Hz, 1H), 7.78-7.60 (m, 2H), 7.26 (t, J=7.6 Hz, 1H), 7.13 (d, J=7.6 Hz, 2H), 6.38 (s, 1H), 5.13 (dd, J=10.7, 4.2 Hz, 1H), 4.39 (t, J=11.1 Hz, 1H), 4.23 (p, J=8.5 Hz, 1H), 3.73 (t, J=11.6 Hz, 1H), 3.30-3.20 (m, 2H), 2.31-1.77 (m, 8H), 1.67 (t, J=13.9, Hz, 1H), 1.32-1.24 (m, 1H), 1.16 (ddd, J=13.7, 10.4, 2.7 Hz, 1H), 0.73 (d, J=6.6 Hz, 3H), 0.22 (d, J=6.3 Hz, 3H). ESI-MS m/z calc. 564.2708, found 565.46 (M+1)+; Retention time: 2.05 minutes (LC method A).

Deuterium content was determined by liquid chromatography mass spectrometry using a Sciex triple quad instrument. About 0.1 mg/mL of the sample was dissolved in MeOH. 10 µL of the sample was diluted in 1 mL MeOH. 1 µL of the sample was injected in the instrument. Column: Phenomenex Synergy Fusion RP 4 µm, 80 A 50×2 mm. Flow rate: 0.5 mL/min. Gradient: 40% B to 95% B in 3.5 min. Mobile phase A: 0.1% Formic acid in water. B: acetonitrile. The selected ion monitoring method was used. The mass spectrometer was operated in a positive ionization mode with an ESI source. The percentage of each ion monitored was as follows: $D_4$: 98.52%, $D_3$: 1.45%, $D_2$: 0.00%, $D_1$: 0.02%; $D_0$: 0.02%.

Example 6: Synthesis of a Potassium Salt of Compound Ia

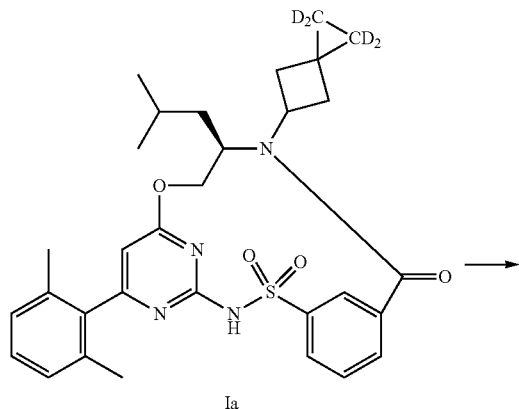

Ia

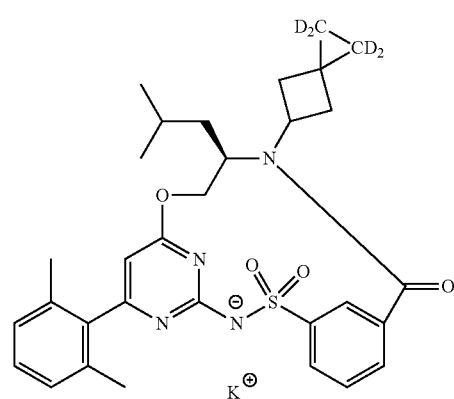

Compound Ia is dissolved in methanol and slowly treated with KOH (0.5 M in methanol) under stirring. The solution is stirred at ambient temperature for 1 h, evaporated, and dried under house vacuum with nitrogen leak at 50-55° C. for 16 h to give Compound Ia (Potassium Ion).

Example 7: Synthesis of a Sodium Salt of Compound Ia

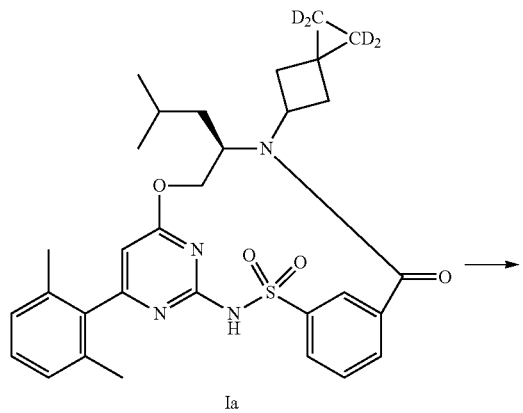

Ia

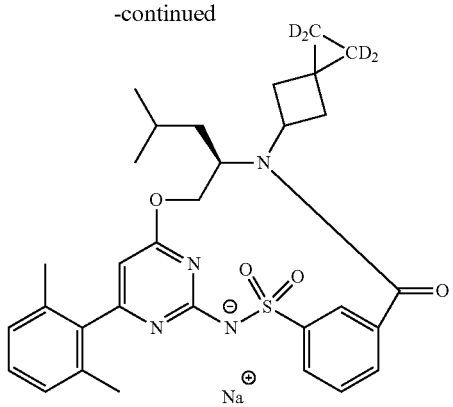

Compound Ia is suspended in water and slowly treated with NaOH (1 M) under stirring. The suspension is stirred at ambient temperature for 1.25 h. The solution is filtered clear over a syringe filter (0.2 μm) and the clear filtrate is lyophilized for two days to give Compound Ia (Sodium salt).

Example 8: Synthesis of a Calcium Salt of Compound Ia

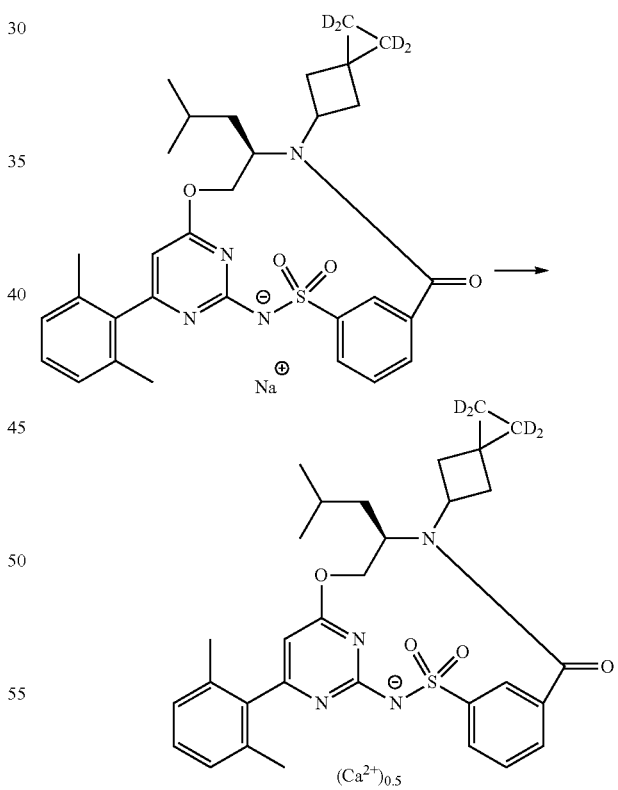

Compound Ia (Sodium salt) is stirred in water for 10 min. A solution of $CaCl_2$ in water is added. Another portion of water is added and the suspension stirred at ambient temperature for 23 h. The solid is collected by filtration, washed with plenty of water, and dried under vacuum with a nitrogen bleed at 55-60° C. for 14 h to give Compound Ia (Calcium salt (0.5)).

Example 9: Synthesis of (11R)-6-(2,6-Dimethylphenyl)-11-isobutyl-2,2-dioxo-12-(4,4,5,6,6-pentadeuteriospiro[2.3]hexan-5-yl)-9-oxa-2-thia-3,5,12,19-tetrazatricyclo[12.3.1.1⁴,⁸]nonadeca-1(18),4,6,8(19),14,16-hexaen-13-one (Compound Ib)

Synthesis of 4,4,6,6-Tetradeuteriospiro[2.3]hexan-5-one (21)

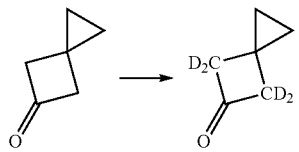

A mixture of spiro[2.3]hexan-5-one (2.17 g, 22.574 mmol) and potassium carbonate (8 g, 57.885 mmol) in triglyme (24 mL) and $D_2O$ (8 mL) was stirred at 70° C. for 24 h. After cooling to ambient temperature, the reaction was extracted with ether (5×16 mL). The combined ether layers were dried over anhydrous sodium sulfate and filtered. The filtrate was concentrated under atmosphere pressure to remove diethyl ether, and then it was distilled under reduced pressure (50-60 mBar, 50 to 60° C.) to furnish 4,4,6,6-tetradeuteriospiro[2.3]hexan-5-one (1.07 g, 13%) as a clear liquid.

A second reaction was run. A mixture of spiro[2.3]hexan-5-one (2 g, 20.806 mmol) and potassium carbonate (7.0 g, 50.649 mmol) in triglyme (21 mL) and $D_2O$ (7 mL) was stirred at 70° C. for 24 h. After being cooled to ambient temperature, the solution was extracted with diethyl ether (5×14 mL). The combined ether layers were dried over anhydrous sodium sulfate. The ether was removed under atmosphere pressure. The residue was distilled under vacuum (50-60 mbar, 50-60° C.) to furnish 4,4,6,6-tetradeuteriospiro[2.3]hexan-5-one (1.222 g, 37%) as a clear liquid. Both batches of crude product were combined and subjected to another deuterium exchange reaction.

Into a solution of crude 4,4,6,6-tetradeuteriospiro[2.3]hexan-5-one (2.29 g, 8.4601 mmol) in triglyme (6 mL) was added a solution of potassium carbonate (2.9231 g, 21.150 mmol) in $D_2O$ (3 mL). The reaction mixture was stirred at 70° C. for 24 h. After being cooled to ambient temperature, the reaction was extracted with diethyl ether (3×10 mL). The combined ether layers were dried over anhydrous sodium sulfate and concentrated under atmosphere pressure. To the residue was added a saturated sodium bisulfite solution (20 mL), and it was stirred for 1 h. The aqueous layer was extracted with diethyl ether (3×20 mL). The organic layer was discarded. The aqueous layer was basified with 10% NaOH (aq), and then it was extracted with diethyl ether (3×20 mL). The ether was removed by distillation under 1 atm pressure to furnish a 9.01% solution of 4,4,6,6-tetradeuteriospiro[2.3]hexan-5-one (2.55 g, 27%) in triglyme and diethyl ether. This triglyme solution was used for the next step without any further purification.

¹H NMR (250 MHz, Chloroform-d) δ 0.77 (d, J=0.3 Hz, 4H).

Synthesis of 3-[[4-(2,6-Dimethylphenyl)-6-[(2R)-4-methyl-2-[(4,4,5,6,6-pentadeuteriospiro[2.3]hexan-5-yl)amino]pentoxy]pyrimidin-2-yl]sulfamoyl]benzoic acid (Hydrochloride Salt) (22)

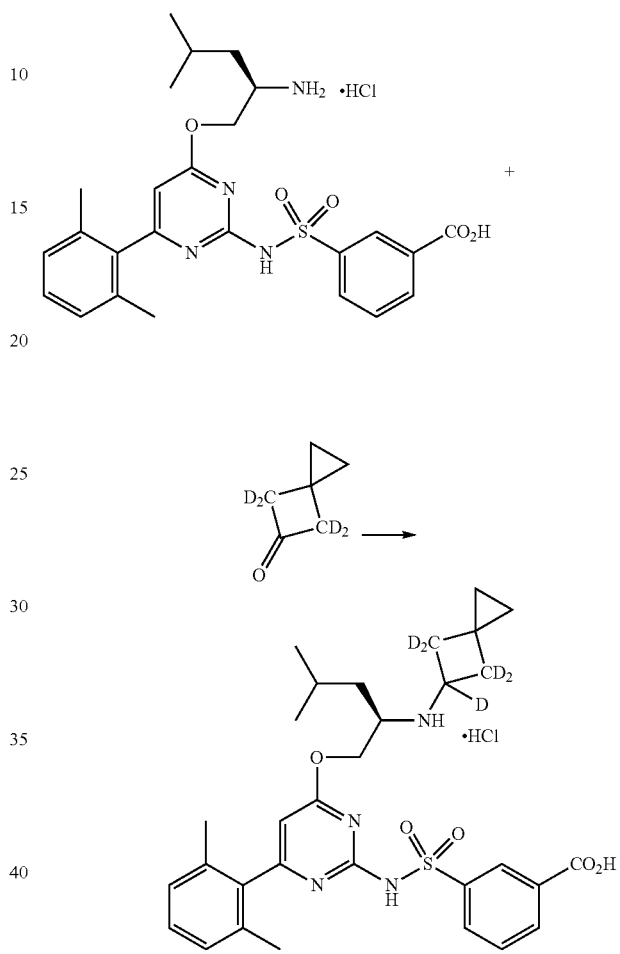

A 4 mL vial was charged under nitrogen with 3-[[4-[(2R)-2-amino-4-methyl-pentoxy]-6-(2,6-dimethylphenyl)pyrimidin-2-yl]sulfamoyl]benzoic acid (Hydrochloride salt) (43 mg, 0.08037 mmol), 4,4,6,6-tetradeuteriospiro[2.3]hexan-5-one (157 mg of 9% w/w, 0.1411 mmol) (9% pure material in triglyme solution), and cyano(trideuterio)boranuide (Sodium salt) (19 mg, 0.2885 mmol). The vial was purged with nitrogen, capped and the resulting suspension was vigorously stirred at ambient temperature for 1 h and 15 min. The reaction was quenched by the addition of deuterated methanol-$d_4$ (1 mL, 24.68 mmol). The solution was microfiltered through a Whatman 0.45 μM PTFE syringe filter disc and purified by reverse phase preparative HPLC (C18) using a gradient of acetonitrile in water (1 to 99% over 15 min) and HCl as a modifier. The pure fractions were collected and the solvents evaporated with a genevac to give 3-[[4-(2,6-dimethylphenyl)-6-[(2R)-4-methyl-2-[(4,4,5,6,6-pentadeuterio-spiro[2.3]hexan-5-yl)amino]pentoxy]pyrimidin-2-yl]sulfamoyl]benzoic acid (Hydrochloride salt) (24 mg, 48%). ESI-MS m/z calc. 583.28766, found 584.45 (M+1)⁺; Retention time: 1.26 minutes. Significant presence of d4 product also visible (M+H=583) (LC method A).

Synthesis of (11R)-6-(2,6-Dimethylphenyl)-11-isobutyl-2,2-dioxo-12-(4,4,5,6,6-pentadeuteriospiro[2.3]hexan-5-yl)-9-oxa-2-thia-3,5,12,19-tetrazatricyclo[12.3.1.1⁴,⁸]nonadeca-1(18),4,6,8(19),14,16-hexaen-13-one (Compound Ib)

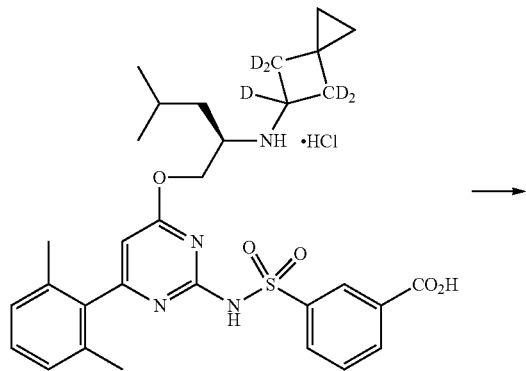

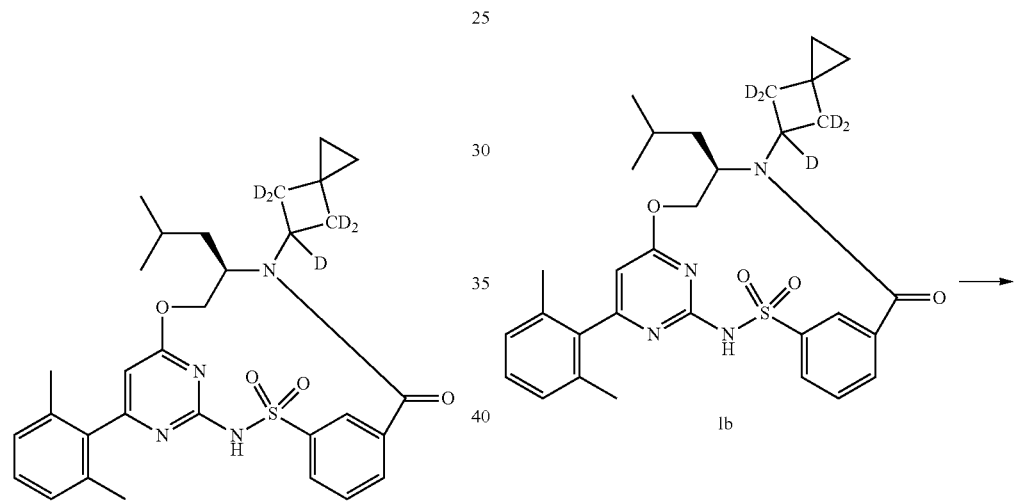

A 100 mL flask was charged under nitrogen with 3-[[4-(2,6-dimethylphenyl)-6-[(2R)-4-methyl-2-[(4,4,5,6,6-pentadeuteriospiro[2.3]hexan-5-yl)amino]pentoxy]pyrimidin-2-yl]sulfamoyl]benzoic acid (Hydrochloride salt) (24 mg, 0.03870 mmol), HATU (53 mg, 0.1394 mmol), anhydrous DMF (2.5 mL) and DIEA (40 μL, 0.2296 mmol). The mixture was stirred at ambient temperature for 2.5 days. The mixture was concentrated and diluted with DMSO (2 mL). The solution was microfiltered through a Whatman 0.45 μM PTFE syringe filter disc and purified by reverse phase preparative HPLC (C18) using a gradient of acetonitrile in water (1 to 99% over 15 min) and HCl as a modifier. Genevac evaporation gave (11R)-6-(2,6-dimethylphenyl)-11-isobutyl-2,2-dioxo-12-(4,4,5,6,6-pentadeuteriospiro[2.3]hexan-5-yl)-9-oxa-2λ⁶-thia-3,5,12,19-tetrazatricyclo[12.3.1.1¹⁴,⁸]nonadeca-1(18),4,6, 8(19),14,16-hexaen-13-one (4.2 mg, 19%) as an off-white solid.

$^1$H NMR (500 MHz, DMSO-$d_6$) δ 13.41-11.69 (broad m, 1H), 8.40 (s, 1H), 7.91 (d, J=7.4 Hz, 1H), 7.77-7.60 (m, 2H), 7.25 (t, J=7.7 Hz, 1H), 7.12 (d, J=7.6 Hz, 2H), 6.38 (s, 1H), 5.12 (dd, J=10.8, 4.2 Hz, 1H), 4.39 (t, J=11.1 Hz, 1H), 3.72 (td, J=11.4, 6.0 Hz, 1H), 2.25-1.85 (m, 6H), 1.66 (ddd, J=14.0, 10.6, 2.8 Hz, 1H), 1.39-1.25 (m, 1H), 1.15 (ddd, J=13.8, 10.5, 2.8 Hz, 1H), 0.72 (d, J=6.6 Hz, 3H), 0.54-0.36 (m, 4H), 0.21 (d, J=6.3 Hz, 3H). ESI-MS m/z calc. 565.2771, found 566.43 (M+1)⁺; Retention time: 2.04 minutes. (LC method A).

Deuterium content was determined by liquid chromatography mass spectrometry using a Sciex triple quad instrument. About 0.1 mg/mL of the sample was dissolved in MeOH. 10 μL of the sample was diluted in 1 mL MeOH. 1 μL of the sample was injected in the instrument. Column: Phenomenex Synergy Fusion RP 4 μm, 80 A 50×2 mm. Flow rate: 0.5 mL/min. Gradient: 40% B to 95% B in 3.5 min. Mobile phase A: 0.1% Formic acid in water. B: acetonitrile. The selected ion monitoring method was used. The mass spectrometer was operated in a positive ionization mode with an ESI source. The percentage of each ion monitored was as follows: $D_5$: 58.66%, $D_4$: 34.01%, $D_3$: 6.81%, $D_2$: 0.47%, $D_1$: 0.03%; $D_0$: 0.02%.

Example 10: Synthesis of a Potassium Salt of Compound Ib

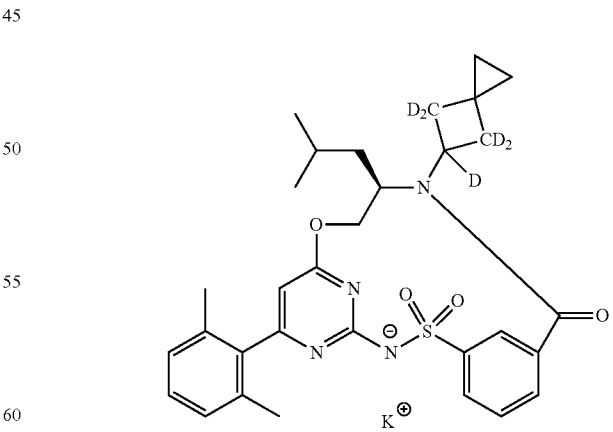

Compound Ib is dissolved in methanol and slowly treated with KOH (0.5 M in methanol) under stirring. The solution is stirred at ambient temperature for 1 h, evaporated, and dried under house vacuum with nitrogen leak at 50-55° C. for 16 h to give Compound Ib (Potassium Ion).

Example 11: Synthesis of a Sodium Salt of Compound Ib

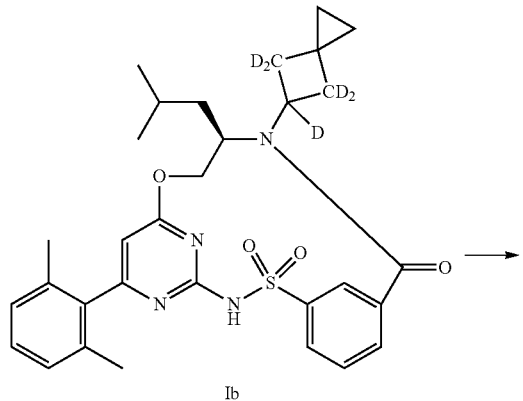

Ib

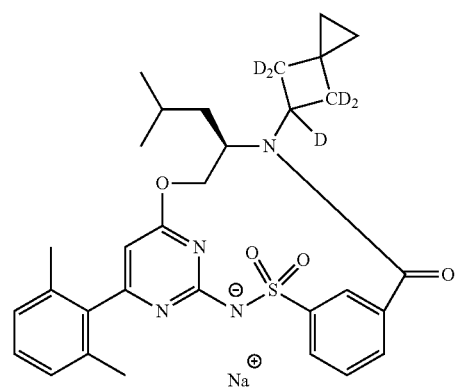

Compound Ib is suspended in water and slowly treated with NaOH (1 M) under stirring. The suspension is stirred at ambient temperature for 1.25 h. The solution is filtered clear over a syringe filter (0.2 μm) and the clear filtrate is lyophilized for two days to give Compound Ib (Sodium salt).

Example 12: Synthesis of a Calcium Salt of Compound Ib

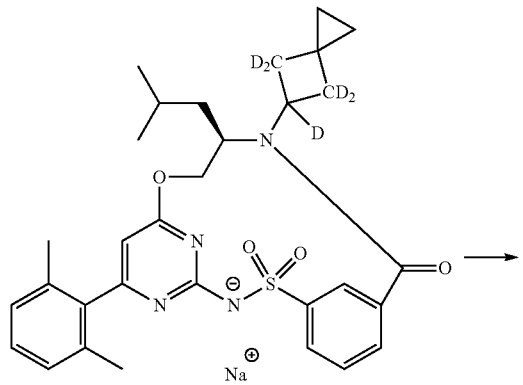

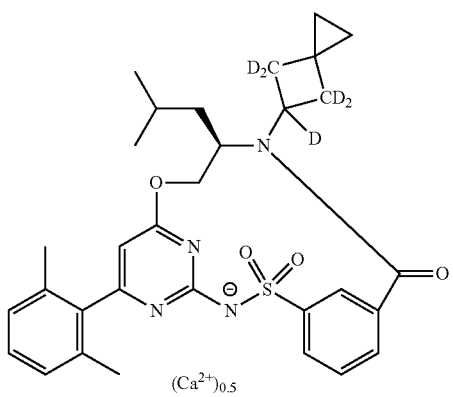

$(Ca^{2+})_{0.5}$

Compound Ib (Sodium salt) is stirred in water for 10 min. A solution of $CaCl_2$ in water is added. Another portion of water is added and the suspension stirred at ambient temperature for 23 h. The solid is collected by filtration, washed with plenty of water, and dried under vacuum with a nitrogen bleed at 55-60° C. for 14 h to give Compound Ib (Calcium salt (0.5)).

Example 13: Synthesis of (11R)-12-(5-Deuteriospiro[2.3]hexan-5-yl)-6-(2,6-dimethylphenyl)-11-isobutyl-2,2-dioxo-9-oxa-2-thia-3,5,12,19-tetrazatricyclo[12.3.1.1⁴,⁸]nonadeca-1(18),4,6,8(19),14,16-hexaen-13-one (Compound Ic)

Synthesis of 3-[[4-[(2R)-2-[(5-Deuteriospiro[2.3]hexan-5-yl)amino]-4-methyl-pentoxy]-6-(2,6-dimethylphenyl)pyrimidin-2-yl]sulfamoyl]benzoic acid (Hydrochloride Salt) (23)

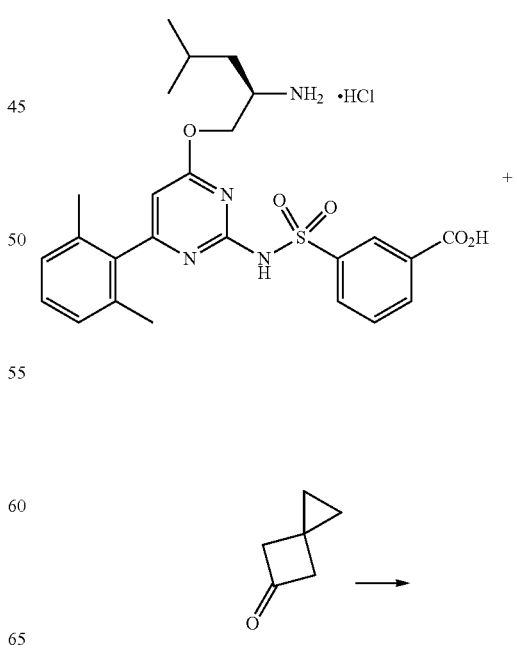

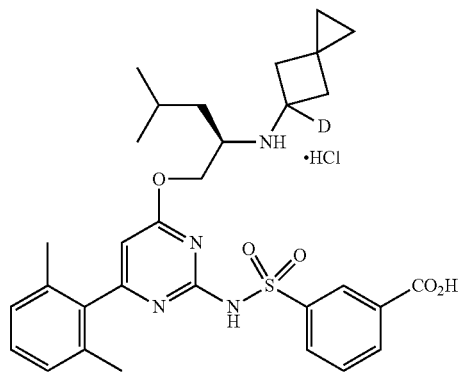

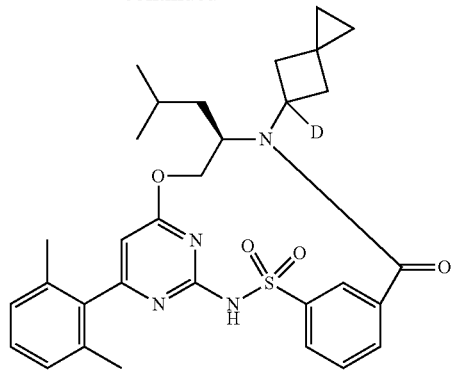

A 4 mL vial was charged with 3-[[4-[(2R)-2-amino-4-methyl-pentoxy]-6-(2,6-dimethylphenyl)pyrimidin-2-yl]sulfamoyl]benzoic acid (Hydrochloride salt) (99 mg, 0.1850 mmol), spiro[2.3]hexan-5-one (50 mg, 0.5201 mmol), anhydrous DCM (0.30 mL) and sodium cyanoborodeuteride (36 mg, 0.5466 mmol). The vial was briefly purged with nitrogen and the mixture (thick suspension at the beginning) was vigorously stirred at ambient temperature for 2 h at which time LCMS showed about 50% conversion. Deuterated methanol-d$_4$ (1 mL, 24.62 mmol) was added and the mixture was concentrated and dissolved in DMSO (total final volume 3 mL). The mixture was purified by reverse phase preparative HPLC (C18) using a gradient of acetonitrile in water (1 to 99% over 15 min) and HCl as a modifier. The pure fractions were collected and the solvents evaporated to give 3-[[4-[(2R)-2-[(5-deuteriospiro[2.3]hexan-5-yl)amino]-4-methyl-pentoxy]-6-(2,6-dimethylphenyl)-pyrimidin-2-yl]sulfamoyl]benzoic acid (Hydrochloride salt) (28 mg, 25%) as a white solid. ESI-MS m/z calc. 579.2626, found 580.42 (M+1)$^+$; Retention time: 1.42 minutes (LC method A).

Synthesis of (11R)-12-(5-Deuteriospiro[2.3]hexan-5-yl)-6-(2,6-dimethylphenyl)-11-isobutyl-2,2-dioxo-9-oxa-2-thia-3,5,12,19-tetrazatricyclo[12.3.1.1$^{4,8}$]nonadeca-1(18),4,6,8(19),14,16-hexaen-13-one (Compound Ic)

A 20 mL flask was charged under nitrogen with HATU (48 mg, 0.1262 mmol), anhydrous DMF (2 mL) and DIEA (45 µL, 0.2584 mmol). A solution of 3-[[4-[(2R)-2-[(5-deuteriospiro[2.3]hexan-5-yl)amino]-4-methyl-pentoxy]-6-(2,6-dimethylphenyl)pyrimidin-2-yl]sulfamoyl]benzoic acid (Hydrochloride salt) (28 mg, 0.04544 mmol) in anhydrous DMF (1 mL) was added dropwise through syringe and the mixture was stirred at ambient temperature for 14 h. The mixture was concentrated and diluted with DMSO (2 mL). The solution was microfiltered through a Whatman 0.45 µM PTFE syringe filter disc and purified by reverse phase preparative HPLC (C18) using a gradient of acetonitrile in water (1 to 99% over 15 min) and HCl as a modifier. Evaporation gave a residue that was triturated in DCM/hexanes. Evaporation of the solvents gave (11R)-12-(5-deuteriospiro[2.3]hexan-5-yl)-6-(2,6-dimethylphenyl)-11-isobutyl-2,2-dioxo-9-oxa-2λ$^6$-thia-3,5,12,19-tetrazatricyclo[12.3.1.1$^{4,8}$]nonadeca-1(18),4,6,8(19),14,16-hexaen-13-one (11 mg, 42%) as a white solid. $^1$H NMR (400 MHz, DMSO-d$_6$) δ 12.52 (broad m, 1H), 8.40 (s, 1H), 7.90 (br s, 1H), 7.67 (br s, 2H), 7.24 (t, J=7.9 Hz, 1H), 7.12 (d, J=7.6 Hz, 2H), 6.37 (br s, 1H), 5.11 (dd, J=10.8, 4.2 Hz, 1H), 4.39 (t, J=11.0 Hz, 1H), 3.74 (d, J=11.4 Hz, 1H), 3.27 (dd, J=10.1, 5.0 Hz, 2H), 2.24-1.81 (m, 8H), 1.66 (t, J=11.8 Hz, 1H), 1.38-1.23 (m, 1H), 1.23-1.00 (m, 1H), 0.72 (d, J=6.6 Hz, 3H), 0.59-0.37 (m, 4H), 0.21 (d, J=6.2 Hz, 3H). $^1$H NMR shows about 95% of D$_1$ analog and about 5% of non-deuterated analog. ESI-MS m/z calc. 561.252, found 562.48 (M+1)$^+$; Retention time: 2.07 minutes (LC method A).

Example 14: Synthesis of a Potassium Salt of Compound Ic

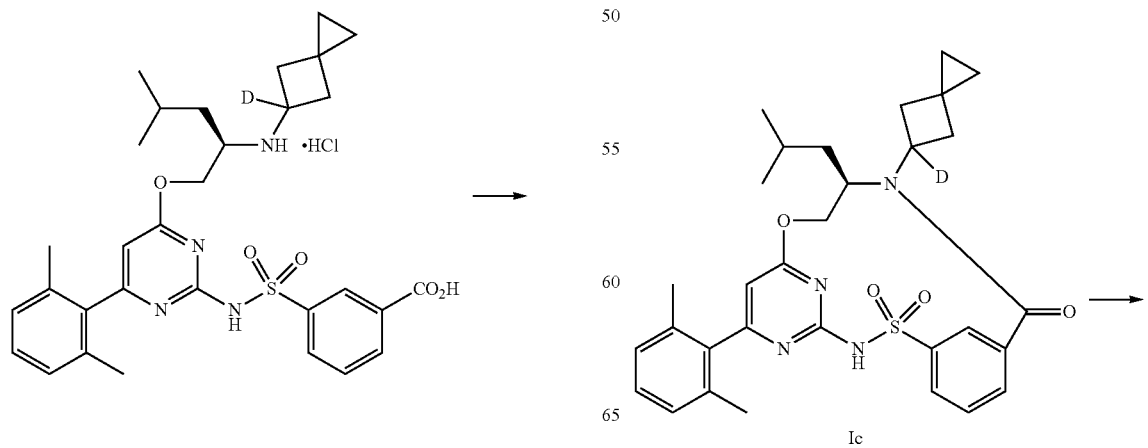

73
-continued

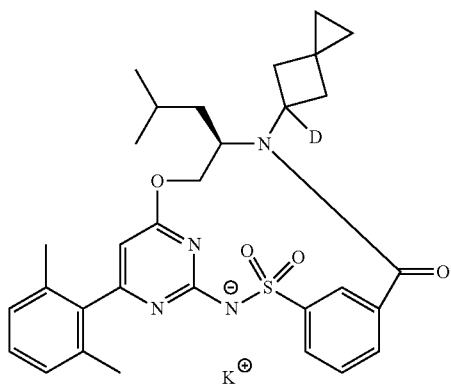

Compound Ic is dissolved in methanol and slowly treated with KOH (0.5 M in methanol) under stirring. The solution is stirred at ambient temperature for 1 h, evaporated, and dried under house vacuum with nitrogen leak at 50-55° C. for 16 h to give Compound Ic (Potassium Ion).

Example 15: Synthesis of a Sodium Salt of Compound Ic

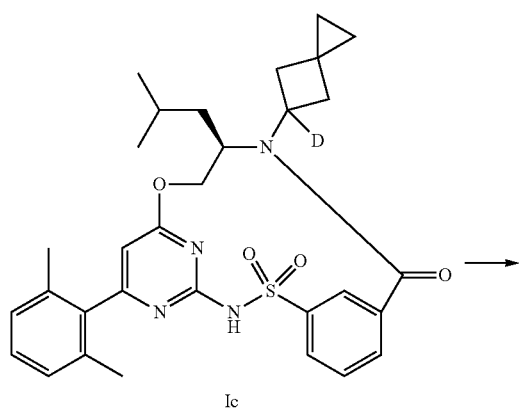

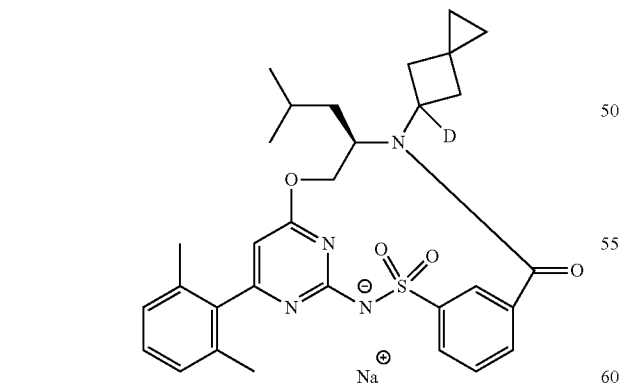

Compound Ic is suspended in water and slowly treated with NaOH (1 M) under stirring. The suspension is stirred at ambient temperature for 1.25 h. The solution is filtered clear over a syringe filter (0.2 μm) and the clear filtrate is lyophilized for two days to give Compound Ic (Sodium salt).

74

Example 16: Synthesis of a Calcium Salt of Compound Ic

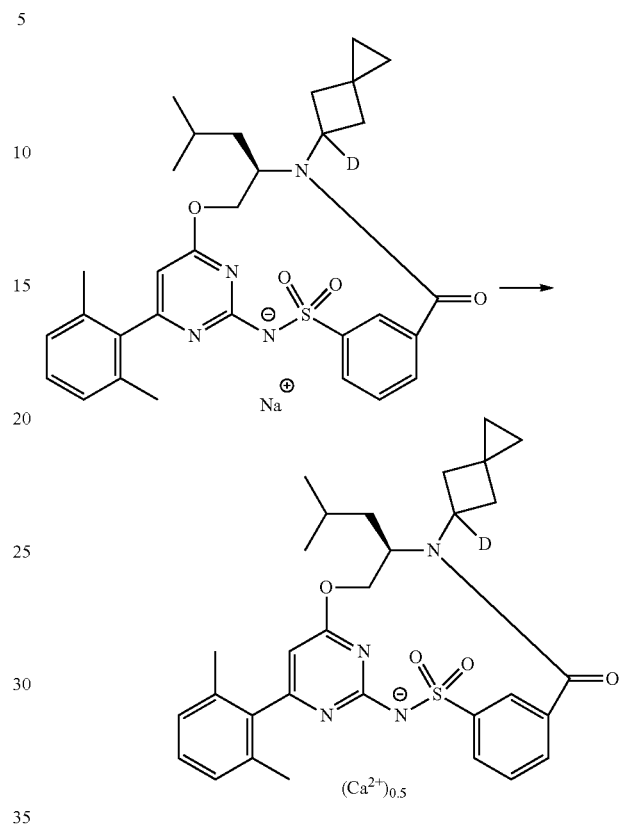

Compound Ic (Sodium salt) is stirred in water for 10 min. A solution of $CaCl_2$ in water is added. Another portion of water is added and the suspension stirred at ambient temperature for 23 h. The solid is collected by filtration, washed with plenty of water, and dried under vacuum with a nitrogen bleed at 55-60° C. for 14 h to give Compound Ic (Calcium salt (0.5)).

Example 17: Synthesis of (11R)-6-[2,6-di(trideutero)methylphenyl]-11-(2-methylpropyl)-12-{spiro[2.3]hexan-5-yl}-9-oxa-2λ⁶-thia-3,5,12,19-tetraaza-tricyclo[12.3.1.1⁴,⁸]nonadeca-1(17),4(19),5,7,14(18),15-hexaene-2,2,13-trione (Compound Id)

Synthesis of 2-Bromobenzene-1,3-dicarboxylic acid (25)

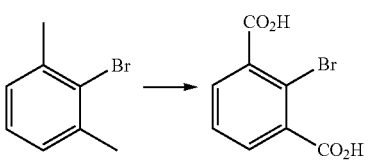

To a stirring solution of 2-bromo-1,3-dimethyl-benzene (35.25 g, 190.48 mmol) in a mixture of tert-butanol (150 mL) and water (150 mL) at ambient temperature was portion-wise added potassium permanganate (61 g, 385.99 mmol). After the addition was complete, the reaction mixture was heated to 85° C. for 3 h. After cooling to ambient temperature, another portion of potassium permanganate (62 g, 392.32 mmol) was added. The reaction mixture was then heated to 85° C. for 16 h. The reaction mixture was filtered hot through a pad of celite, and the filter cake was washed with a hot 1:1 mixture of tert-butanol and water (2×100 mL). The combined filtrates were concentrated under vacuum to a residual volume of ~200 mL and acidified to pH ~1 with concentrated sulfuric acid. The mixture was cooled to 0° C. and left standing for 2 h. The precipitated product was collected by filtration, and the aqueous filtrate was further extracted with ethyl acetate (2×80 mL). The combined organic layers were washed with brine (40 mL), dried over anhydrous sodium sulfate and concentrated. All product fractions were combined, washed with hexanes (2×100 mL), and dried under vacuum to afford 2-bromobenzene-1,3-dicarboxylic acid (24.86 g, 51%) as a white solid. The product was carried forward to the next step without any further purification.

$^1$H NMR (250 MHz, DMSO-$d_6$) δ 7.71 (d, J=7.6 Hz, 2H), 7.53 (t, J=7.6 Hz, 1H).

ESI-MS m/z calc. 243.9371, found 245.3 (M+1)$^+$; Retention time: 1.63 minutes (LC Method C).

Synthesis of Dimethyl 2-bromobenzene-1,3-dicarboxylate (26)

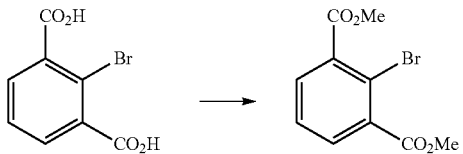 [SMILES: O=C(O)c1cccc(C(=O)O)c1Br ; COC(=O)c1cccc(C(=O)OC)c1Br]

To a stirring solution of 2-bromobenzene-1,3-dicarboxylic acid (25.15 g, 102.64 mmol) in anhydrous DMF (250 mL) at ambient temperature under nitrogen was added anhydrous $K_2CO_3$ (31.5 g, 227.92 mmol), followed by iodomethane (32.376 g, 14.2 mL, 228.10 mmol). The reaction mixture was stirred at this temperature for 24 h. The reaction mixture was poured into brine (750 mL), and the product was extracted with ethyl acetate (3×250 mL). The combined organic layers were washed with brine (450 mL), dried over anhydrous sodium sulfate and concentrated to afford dimethyl 2-bromobenzene-1,3-dicarboxylate (28.45 g, 94%) as an amber oil. The product was carried to the next step without further purification. $^1$H NMR (250 MHz, DMSO-$d_6$) δ 7.91-7.74 (m, 2H), 7.70-7.52 (m, 1H), 3.88 (s, 6H). ESI-MS m/z calc. 271.9684, found 273.4 (M+1)$^+$; Retention time: 4.23 minutes (LC Method C).

Synthesis of [2-Bromo-3-[dideuterio(hydroxy)methyl]phenyl]-dideuterio-methanol (27)

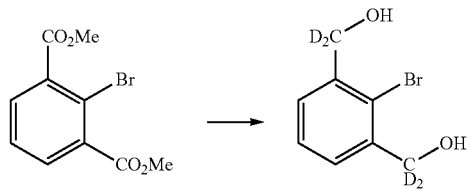

To a stirring suspension of lithium aluminum deuteride (200 mg, 5.0044 mmol) in anhydrous THF (3 mL) at 0° C. under nitrogen was dropwise added a solution of dimethyl 2-bromobenzene-1,3-dicarboxylate (585 mg, 2.1422 mmol) in anhydrous THF (1 mL). After the addition was complete, the reaction mixture was stirred at this temperature for 1 h. The reaction mixture was diluted with THF (10 mL) and quenched using a standard Fieser protocol. Salts were filtered off and washed with THF (2×10 mL). The combined filtrates were concentrated under vacuum to afford [2-bromo-3-[dideuterio(hydroxy)methyl]phenyl]-dideuterio-methanol (416 mg, 79%) as a white solid. The product was carried to the next step without further purification.

$^1$H NMR (250 MHz, DMSO-$d_6$) δ 7.44-7.39 (m, 3H), 5.37 (s, 2H). ESI-MS m/z calc. 220.0037, found 203.3 (M+1-18)$^+$; Retention time: 1.8 minutes (LC Method C).

Synthesis of 2-Bromo-1,3-bis[bromo(dideuterio)methyl]benzene (28)

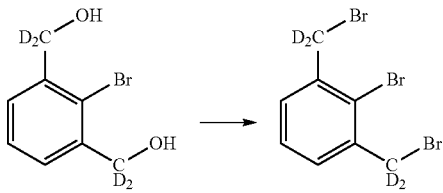

To a stirring suspension of [2-bromo-3-[dideuterio(hydroxy)methyl]phenyl]-dideuterio-methanol (12.56 g, 56.811 mmol) in anhydrous DCM (370 mL) at ambient temperature under nitrogen was added carbon tetrabromide (45.3 g, 136.60 mmol), followed by a portionwise addition of triphenylphosphine (35.8 g, 136.49 mmol) over a 15-minute period. After the addition was complete, the reaction mixture became a homogeneous solution and was stirred at this temperature for 1 h. The reaction mixture was concentrated under vacuum to a residual volume of ~100 mL and poured into diethyl ether (600 mL). The white precipitate was filtered off and washed with diethyl ether (2×50 mL). The combined filtrates were collected and concentrated under vacuum to a residual volume of ~100 mL and poured into hexanes (600 mL). The white precipitate was filtered off and washed with hexanes (2×100 mL). The combined filtrates were collected and concentrated under vacuum. The crude product was purified by silica gel chromatography using 0-10% ethyl acetate gradient in hexanes to afford 2-bromo-1,3-bis[bromo(dideuterio)methyl]benzene (15.56 g, 71%) as a white solid. $^1$H NMR (250 MHz, DMSO-$d_6$) δ 7.60 (d, J=7.6 Hz, 2H), 7.39 (t, J=7.5 Hz, 1H).

Synthesis of 2-Bromo-1,3-bis(trideuteriomethyl)benzene (29)

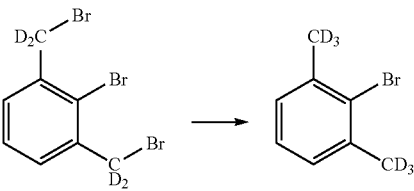

To a stirring suspension of lithium aluminum deuteride (3.65 g, 91.330 mmol) in anhydrous THF (70 mL) at 0° C. under nitrogen was added dropwise a solution of 2-bromo-1,3-bis[bromo(dideuterio)methyl]benzene (15.5 g, 40.216 mmol) in anhydrous THF (70 mL). After the addition was complete, the reaction mixture was stirred at this temperature for 1 h. The reaction mixture was diluted with THF (100 mL), and quenched using a standard Fieser workup protocol. Salts were filtered off and washed with THF (2×50 mL). The combined filtrates were concentrated under vacuum. The residue was re-dissolved in hexanes (200 mL), filtered and concentrated under vacuum to afford 2-bromo-1,3-bis(trideuteriomethyl)benzene (5.58 g, 68%) as a pale yellow oil. The product was carried to the next step without further purification.

¹H NMR (250 MHz, DMSO-d₆) δ 7.23-7.11 (m, 3H).

Synthesis of [2,6-Bis(trideuteriomethyl)phenyl]boronic acid (30)

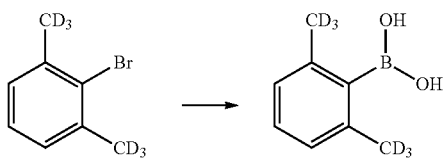

To a stirring suspension of magnesium turnings (1.8 g, 74.059 mmol) and iodine (15 mg, 0.0030 mL, 0.0591 mmol) in anhydrous THF (20 mL) at ambient temperature under nitrogen was slowly added a solution of 2-bromo-1,3-bis(trideuteriomethyl)benzene (9.89 g, 46.578 mmol) in anhydrous THF (50 mL). Once initiated, the reaction is exothermic and the rate of addition was adjusted to keep the reaction temperature below the boiling point of THF. After the addition was complete, the reaction mixture was stirred at 65° C. for 1 h. The prepared solution of Grignard reagent was cooled down to ambient temperature and added dropwise to a solution of trimethyl borate (24.232 g, 26 mL, 233.20 mmol) in anhydrous THF (60 mL) cooled to −78° C. under nitrogen. After the addition was complete, the reaction mixture was stirred at −78° C. for 3 h, then allowed to warm up to ambient temperature and stirred overnight. The reaction mixture was cooled to 0° C. and aqueous HCl (95 mL of 1 M, 95.000 mmol) was slowly added. After the addition was complete, the reaction mixture was warmed up to ambient temperature and stirred for 3 h. Water (100 mL) was added and the volatiles were removed under vacuum. The aqueous layer was extracted with ethyl acetate (3×200 mL). The combined organic layers were washed with brine (80 mL), dried over anhydrous sodium sulfate and concentrated. The obtained residue was triturated with hexanes (100 ml). The precipitated product was collected by filtration and dried under vacuum to afford [2,6-bis(trideuteriomethyl)phenyl]boronic acid (4.667 g, 61%) as a white solid. ¹H NMR (500 MHz, DMSO-d₆) δ 8.11 (broad s, 2H), 7.06 (dd, J=7.9, 7.1 Hz, 1H), 6.91 (d, J=7.5 Hz, 2H).

Synthesis of tert-Butyl N-[4-[2,6-bis(trideuteriomethyl)phenyl]-6-chloro-pyrimidin-2-yl]-N-tert-butoxycarbonyl-carbamate (31)

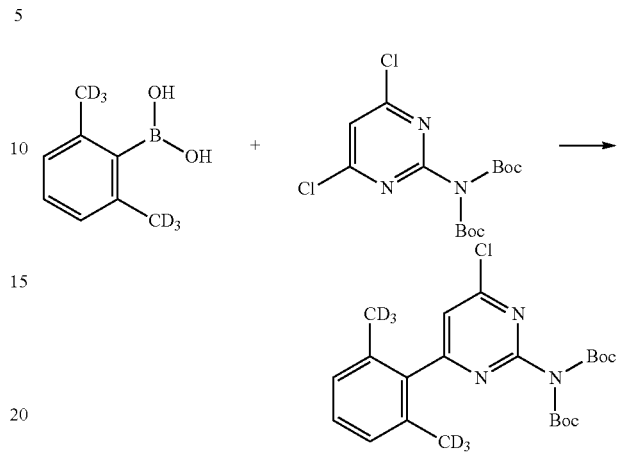

A stirring solution of [2,6-bis(trideuteriomethyl)phenyl]boronic acid (1.565 g, 10.031 mmol) and tert-butyl N-tert-butoxycarbonyl-N-(4,6-dichloropyrimidin-2-yl)carbamate (5.48 g, 15.046 mmol) in a mixture of 1,2-dimethoxyethane (30 mL) and water (10 mL) at ambient temperature was degassed with nitrogen for 30 min. Under nitrogen, cesium carbonate (8.18 g, 25.106 mmol) and [1,1'-bis(diphenylphosphino)-ferrocene]dichloropalladium(II) (735 mg, 1.0045 mmol) were added. The reaction mixture was heated to 80° C. for 3 h. After cooling to ambient temperature, the reaction mixture was diluted with water (120 mL), and the product was extracted with ethyl acetate (3×150 mL). The combined organic layers were washed with brine (50 ml), dried over anhydrous sodium sulfate and concentrated. The crude product was purified by silica gel chromatography using 0-10% diethyl ether gradient in hexanes to afford tert-butyl N-[4-[2,6-bis(trideuteriomethyl)phenyl]-6-chloro-pyrimidin-2-yl]-N-tert-butoxycarbonyl-carbamate (3.6919 g, 79%) as pale yellow oil. ESI-MS m/z calc. 439.2145, found 440.4 (M+1)⁺; Retention time: 7.48 minutes (LC Method C).

Synthesis of 4-[2,6-Bis(trideuteriomethyl)phenyl]-6-chloro-pyrimidin-2-amine (32)

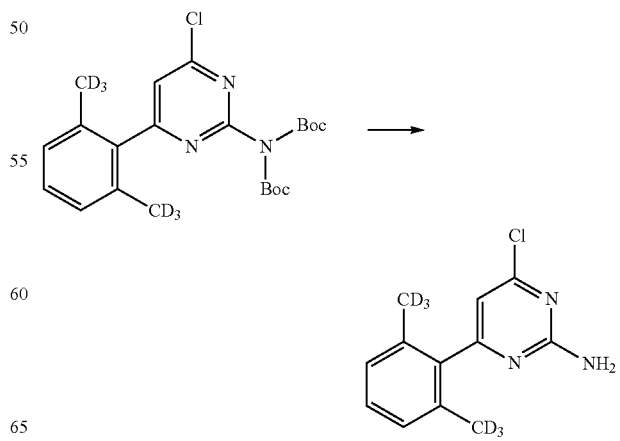

To a stirring solution of tert-butyl N-[4-[2,6-bis(trideuteriomethyl)phenyl]-6-chloro-pyrimidin-2-yl]-N-tert-butoxycarbonyl-carbamate (3.66 g, 8.3188 mmol) in DCM (30 mL) at ambient temperature was added a solution of HCl (12 mL of 4 M, 48.000 mmol) in 1,4-dioxane. The reaction mixture was stirred at this temperature for 20 h. Volatiles were removed under vacuum, the obtained white solid was re-suspended in saturated aqueous NaHCO$_3$ (150 mL) and stirred at ambient temperature for 15 min. The product was extracted with ethyl acetate (3×100 mL). The combined organic layers were washed with brine (50 mL), dried over anhydrous sodium sulfate and concentrated to afford 4-[2,6-bis(trideuteriomethyl)phenyl]-6-chloro-pyrimidin-2-amine (1.842 g, 87%) as a white solid. ESI-MS m/z calc. 239.1096, found 240.3 (M+1)$^+$; Retention time: 4.44 minutes (LC Method C).

Synthesis of Methyl 3-[[4-[2,6-bis(trideuteriomethyl)phenyl]-6-chloro-pyrimidin-2-yl]sulfamoyl]benzoate (33)

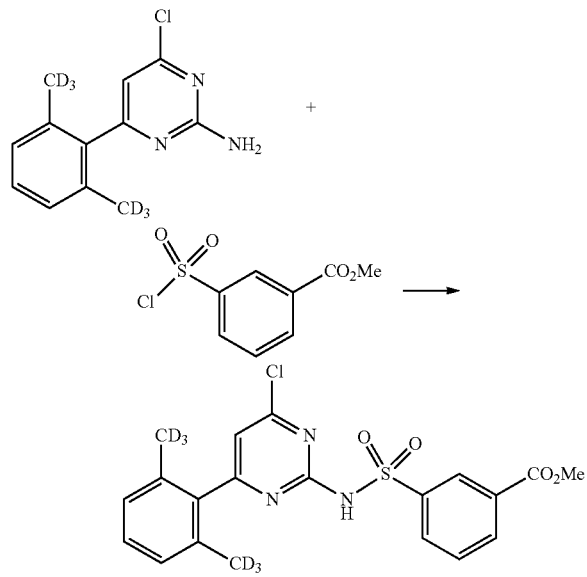

To a stirring solution of 4-[2,6-bis(trideuteriomethyl)phenyl]-6-chloro-pyrimidin-2-amine (1.8 g, 7.5083 mmol) and methyl 3-chlorosulfonylbenzoate (2.64 g, 11.250 mmol) in anhydrous THF (50 mL) at 0° C. under nitrogen was added dropwise a solution of lithium tert-amoxide (3.2120 g, 11 mL of 40% w/w, 13.656 mmol) in heptanes. After the addition was complete, the reaction mixture was stirred at this temperature for 2 h. The reaction mixture was quenched cold with 1 M aqueous HCl (120 mL), then warmed up to ambient temperature and volatiles were removed under vacuum. The product was extracted with ethyl acetate (3×150 mL). Combined organic layers were washed with brine (50 mL), dried over anhydrous sodium sulfate and concentrated. The crude product was purified by silica gel chromatography using 0-20% ethyl acetate gradient in hexanes to afford methyl 3-[[4-[2,6-bis(trideuterio-methyl)phenyl]-6-chloro-pyrimidin-2-yl]sulfamoyl]benzoate (2.786 g, 80%) as a white solid. ESI-MS m/z calc. 437.1083, found 438.3 (M+1)$^+$; Retention time: 5.95 minutes Final purity was determined by reverse phase HPLC using LC Method C.

Synthesis of 3-[[4-[2,6-Bis(trideuteriomethyl)phenyl]-6-chloro-pyrimidin-2-yl]sulfamoyl]benzoic acid (34)

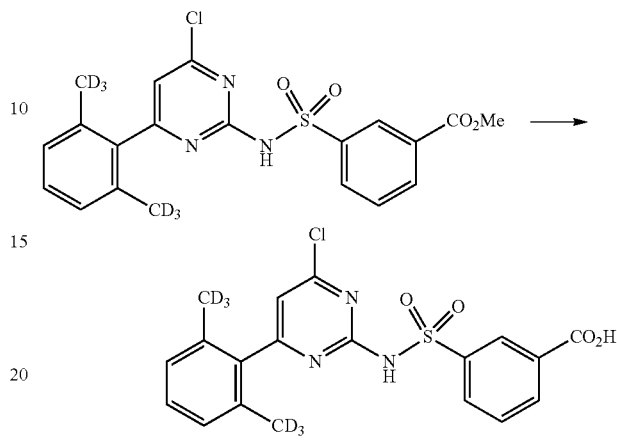

To a stirring solution of methyl 3-[[4-[2,6-bis(trideuteriomethyl)phenyl]-6-chloro-pyrimidin-2-yl]sulfamoyl]benzoate (2.751 g, 6.2818 mmol) in THF (40 mL) at ambient temperature was added aqueous NaOH (26 mL of 1 M, 26.000 mmol). The reaction mixture was stirred at this temperature for 2 h. Water (100 mL) was added, and volatiles were removed under vacuum. The residual aqueous layer was extracted with ethyl acetate (1×100 mL), and the organic layer was discarded. The aqueous layer was acidified with 2 M aqueous HCl to pH ~1, and the product was extracted with ethyl acetate (3×100 mL). Combined organic layers were washed with brine (50 mL), dried over anhydrous sodium sulfate and concentrated to afford 3-[[4-[2,6-bis(trideuterio-methyl)phenyl]-6-chloro-pyrimidin-2-yl]sulfamoyl]benzoic acid (1.719 g, 62%) as a white solid. $^1$H NMR (500 MHz, DMSO-d$_6$) δ 13.43 (s, 1H), 12.44 (s, 1H), 8.44 (t, J=1.8 Hz, 1H), 8.18 (dt, J=7.8, 1.4 Hz, 1H), 8.13 (ddd, J=7.9, 2.0, 1.2 Hz, 1H), 7.68 (t, J=7.8 Hz, 1H), 7.31 (s, 1H), 7.24 (dd, J=8.0, 7.2 Hz, 1H), 7.10 (d, J=7.6 Hz, 2H). ESI-MS m/z calc. 423.0927, found 424.0 (M+1)$^+$; Retention time: 2.28 minutes (LC Method B).

Synthesis of 3-[[4-[2,6-Bis(trideuteriomethyl)phenyl]-6-[(2R)-4-methyl-2-(spiro[2.3]hexan-5-ylamino)pentoxy]pyrimidin-2-yl]sulfamoyl]benzoic acid (Hydrochloride Salt) (35)

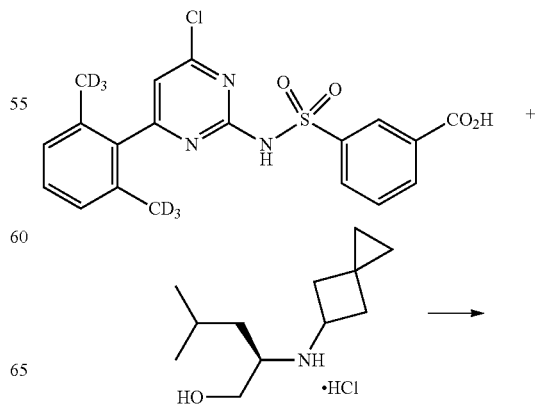

-continued

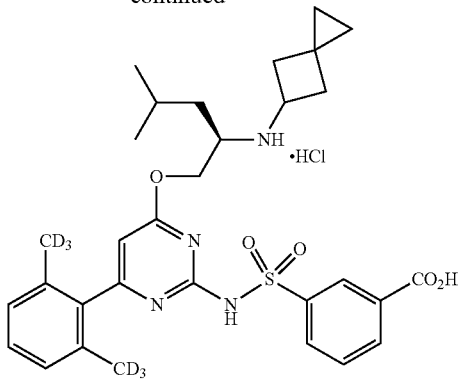

In a 20 mL flask, 3-[[4-[2,6-bis(trideuteriomethyl)phenyl]-6-chloro-pyrimidin-2-yl]sulfamoyl]benzoic acid (157 mg, 0.3704 mmol) and (2R)-4-methyl-2-(spiro[2.3]hexan-5-ylamino)pentan-1-ol (Hydrochloride salt) (90 mg, 0.3850 mmol) were charged under nitrogen with anhydrous THF (2 mL) (suspension). Sodium tert-butoxide (156 mg, 1.623 mmol) was added (slight exotherm and dissolution of solids). The suspension was stirred at ambient temperature for 5.5 h. The mixture was partitioned between ethyl acetate (30 mL) and aqueous 1M HCl (30 mL) and brine (20 mL). After separation, the aqueous phase was further extracted with EtOAc (2×30 ml). The combined extracts were dried over sodium sulfate and the solvents evaporated to give a crude material. The material was dissolved in DMSO (4 mL). The solution was microfiltered through a Whatman 0.45 μM PTFE syringe filter disc and purified by reverse phase preparative HPLC (C18) using a gradient of acetonitrile in water (1 to 99% over 15 min) and HCl as a modifier. Evaporation gave 3-[[4-[2,6-bis(trideuterio-methyl)phenyl]-6-[(2R)-4-methyl-2-(spiro[2.3]hexan-5-ylamino)pentoxy]pyrimidin-2-yl]sulfamoyl]benzoic acid (Hydrochloride salt) (135 mg, 59%) as a white solid. ESI-MS m/z calc. 584.29395, found 585.73 (M+1)$^+$; Retention time: 1.22 minutes (LC method A).

Synthesis (2R)-4-Methyl-2-(spiro[2.3]hexan-5-ylamino)pentan-1-ol (hydrochloride salt) (3·HCl)

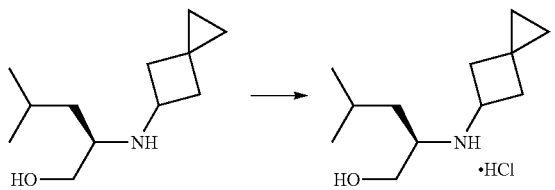

HCl (354 mL of 4 M, 1.416 mol) (4 M in dioxane) was added to a stirring (mechanical) solution of (2R)-4-methyl-2-(spiro[2.3]hexan-5-ylamino)pentan-1-ol (254 g, 1.287 mol) in diethyl ether (2.286 L) in an ice/water bath over 20 minutes, keeping the internal temp between 10° C. and 22° C. After the addition was complete, the solution was stirred at ambient temperature for 1.5 h. The product was filtered out and rinsed with 2000 mL diethyl ether. The exact same process was repeated again on the exact same scale (a total of 508 g of amino alcohol starting material was used). The product was dried under vacuum at 35° C. overnight and gave 562.3 g. (2R)-4-methyl-2-(spiro[2.3]hexan-5-ylamino) pentan-1-ol (Hydrochloride salt) (562.3 g, 93%). $^1$H NMR (500 MHz, DMSO-d$_6$) δ 9.17-8.84 (m, 2H), 5.38 (s, 1H), 3.99 (p, J=7.2 Hz, 1H), 3.70-3.60 (m, 1H), 3.55-3.45 (m, 1H), 3.03-2.91 (m, 1H), 2.63-2.54 (m, 2H), 2.20-2.05 (m, 2H), 1.73-1.60 (m, 1H), 1.60-1.48 (m, 1H), 1.43-1.30 (m, 1H), 0.93-0.83 (m, 6H), 0.55-0.45 (m, 2H), 0.45-0.36 (m, 2H).

Synthesis of (11R)-6-[2,6-di(trideutero)methylphenyl]-11-(2-methylpropyl)-12-{spiro[2.3]hexan-5-yl}-9-oxa-2λ$^6$-thia-3,5,12,19-tetraazatricyclo[12.3.1.14,8]nonadeca-1(17),4(19),5,7,14(18),15-hexaene-2,2,13-trione (Compound Id)

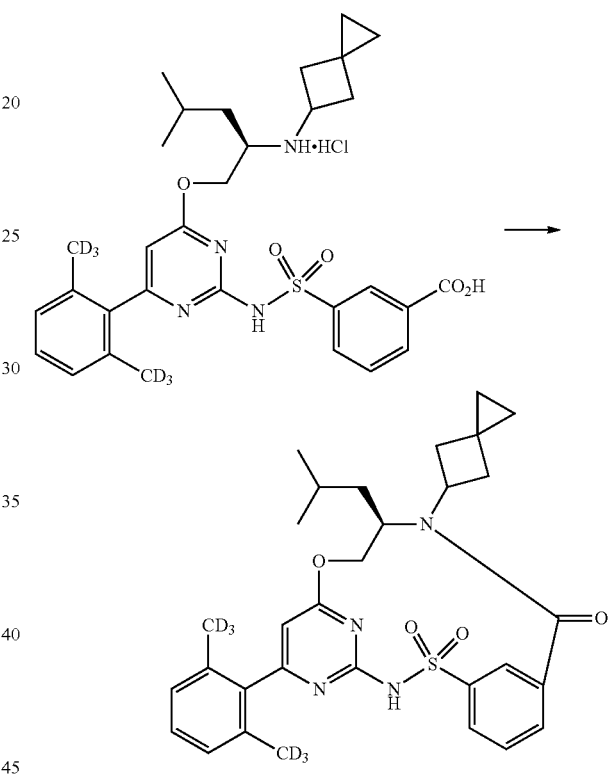

A 20 mL flask was charged under nitrogen with COMU (244 mg, 0.5697 mmol), anhydrous DMF (8 mL) and DIEA (0.22 mL, 1.263 mmol). A solution of 3-[[4-[2,6-bis(trideuteriomethyl)phenyl]-6-[(2R)-4-methyl-2-(spiro[2.3]hexan-5-ylamino)pentoxy]pyrimidin-2-yl]sulfamoyl]benzoic acid (Hydrochloride salt) (135 mg, 0.2173 mmol) in anhydrous DMF (4 mL) was added dropwise through syringe over a period of 3 min. The mixture was stirred at ambient temperature for 17 h. The mixture was concentrated and diluted with DMSO (2 mL). The solution was microfiltered through a Whatman 0.45 μM PTFE syringe filter disc and purified by reverse phase preparative HPLC (C18) using a gradient of acetonitrile in water (1 to 99% over 15 min) and HCl as a modifier. Evaporation gave a residue that was triturated in DCM/hexanes. Evaporation of the solvents gave (11R)-6-[2,6-di(trideutero)-methylphenyl]-11-(2-methylpropyl)-12-{spiro[2.3]hexan-5-yl}-9-oxa-2λ$^6$-thia-3,5,12,19-tetraazatricyclo-[12.3.1.14,8]nonadeca-1(17),4(19),5,7,14(18),15-hexaene-2,2,13-trione (73.4 mg, 60%) as an off-white solid. $^1$H NMR (400 MHz, DMSO-d$_6$) δ 13.47-11.72 (broad m, 1H), 8.40 (s, 1H), 7.99-7.81 (m, 1H), 7.82-7.52 (m, 2H), 7.26 (t, J=7.7 Hz, 1H), 7.12 (d, J=7.6 Hz, 2H), 6.37 (br s, 1H), 5.12 (dd, J=10.7, 4.2 Hz, 1H), 4.39 (t, J=11.1 Hz, 1H), 4.23 (p, J=8.5 Hz, 1H), 3.72 (t, J=10.4 Hz, 1H), 3.30-3.22 (m, 2H, overlapped with water), 2.09 (dt, J=19.0, 9.4 Hz, 2H), 1.66 (t, J=12.5 Hz, 1H), 1.38-1.24 (br m, 1H), 1.15 (dd, J=14.0, 10.4 Hz, 1H), 0.72 (d, J=6.6 Hz, 3H), 0.61-0.35 (m, 4H), 0.21 (d, J=6.2 Hz, 3H). ESI-MS m/z calc. 566.2834, found 567.69 (M+1)$^+$; Retention time: 2.05 minutes (LC method A).

Deuterium content was determined by liquid chromatography mass spectrometry using a single quad instrument. About 0.1 mg/mL of the sample was dissolved in MeOH. 10 μL of the sample was diluted in 1 mL MeOH. 1 μL of the sample was injected into the instrument. Column: Agilent SB C18, 1.8 μm, 2.1×50 mm. Flow rate: 0.7 mL/min. Gradient: 40% B to 100% B in 2.5 min. Mobile phase A: 0.1% trifluoroacetic acid in water. B: acetonitrile. The selected ion monitoring method was used. The mass spectrometer was operated in a positive ionization mode with an ESI source. The percentage of each ion monitored was as follows: $D_6$: 88.49%, $D_5$: 8.14%, $D_4$: 0.93%, $D_3$: 0.52%, $D_2$: 1.93%, $D_1$: 0.00%; $D_0$: 0.00%.

Example 18: Synthesis of a Potassium Salt of Compound Id

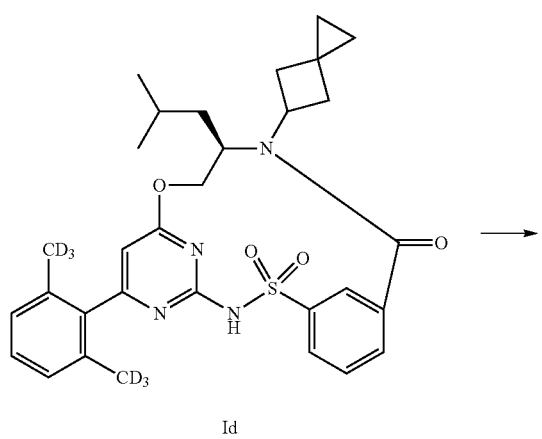

Compound Id is dissolved in methanol and slowly treated with KOH (0.5 M in methanol) under stirring. The solution is stirred at ambient temperature for 1 h, evaporated, and dried under house vacuum with nitrogen leak at 50-55° C. for 16 h to give Compound Id (Potassium Ion).

Example 19: Synthesis of a Sodium Salt of Compound Id

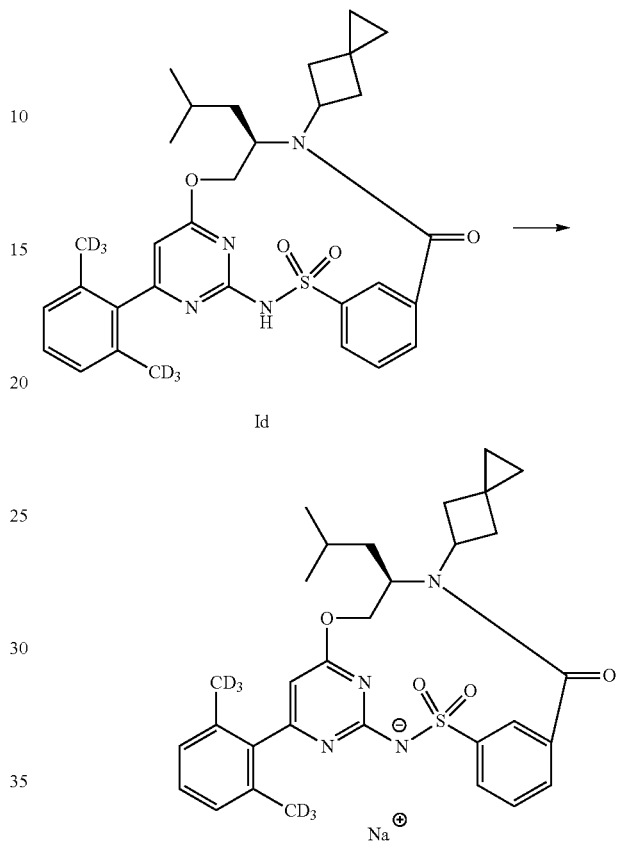

Compound Id is suspended in water and slowly treated with NaOH (1 M) under stirring. The suspension is stirred at ambient temperature for 1.25 h. The solution is filtered clear over a syringe filter (0.2 μm) and the clear filtrate is lyophilized for two days to give Compound Id (Sodium salt).

Example 20: Synthesis of a Calcium Salt of Compound Id

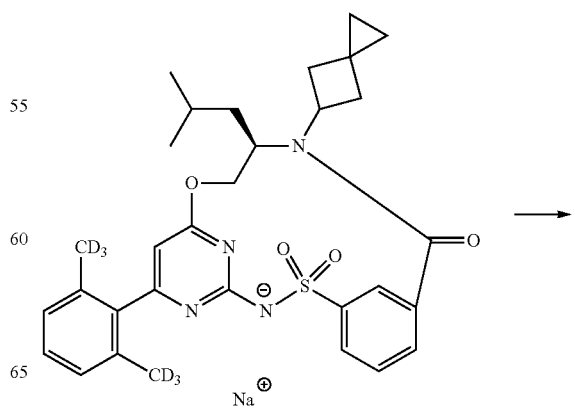

-continued

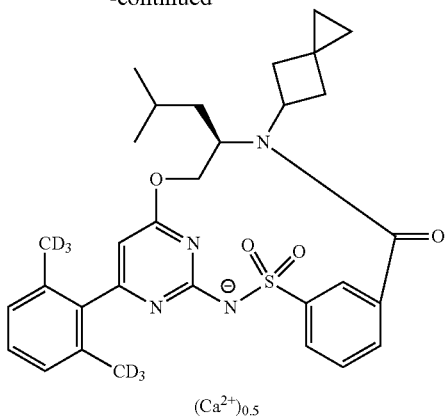

(Ca²⁺)₀.₅

Compound Id (Sodium salt) is stirred in water for 10 min. A solution of CaCl$_2$ in water is added. Another portion of water is added and the suspension stirred at ambient temperature for 23 h. The solid is collected by filtration, washed with plenty of water, and dried under vacuum with a nitrogen bleed at 55-60° C. for 14 h to give Compound Id (Calcium salt (0.5)).

Bioactivity Assays

Solutions

Base medium (ADF+++) consisted of Advanced DMEM/Ham's F12, 2 mM Glutamax, 10 mM HEPES, 1 µg/ml penicillin/streptomycin.

Intestinal enteroid maintenance medium (IEMM) consisted of ADF+++, 1×B27 supplement, 1×N2 supplement, 1.25 mM N-acetyl cysteine, 10 mM Nicotinamide, 50 ng/mL hEGF, 10 nM Gastrin, 1 µg/mL hR-spondin-1, 100 ng/mL hNoggin, TGF-b type 1 inhibitor A-83-01, 100 µg/mL Primocin, 10 µM P38 MAPK inhibitor SB202190.

Bath 1 Buffer consisted of 1 mM MgCl$_2$, 160 mM NaCl, 4.5 mM KCl, 10 mM HEPES, 10 mM Glucose, 2 mM CaCl$_2$.

Chloride Free Buffer consisted of 1 mM Magnesium Gluconate, 2 mM Calcium Gluconate, 4.5 mM Potassium Gluconate, 160 mM Sodium Gluconate, 10 mM HEPES, 10 mM Glucose.

Bath1 Dye Solution consisted of Bath 1 Buffer, 0.04% Pluronic F127, 20 µM Methyl Oxonol, 30 µM CaCCinh-A01, 30 µM Chicago Sky Blue.

Chloride Free Dye Solution consisted of Chloride Free Buffer, 0.04% Pluronic F127, 20 µM Methyl Oxonol, 30 µM CaCCinh-A01, 30 µM Chicago Sky Blue.

Chloride Free Dye Stimulation Solution consisted of Chloride Free Dye Solution, 10 µM forskolin, 100 µM IBMX, and 300 nM Compound III.

Cell Culture

Human intestinal epithelial enteroid cells were obtained from the Hubrecht Institute for Developmental Biology and Stem Cell Research, Utrecht, The Netherlands and expanded in T-Flasks as previously described (Dekkers J F, Wieginck C L, de Jonge H R, Bronsveld I, Janssens H M, de Winter-de Groot K M, Brandsma A M, de Jong N W M, Bijvelds M J C, Scholte B J, Nieuwenhuis E E S, van den Brink S, Clevers H, van der Ent C K, Middendorp S and Beekman J M. A functional CFTR assay using primary cystic fibrosis intestinal organoids. Nat. Med. 2013 July; 19(7):939-45.

Enteroid Cell Harvesting and Seeding

Cells were recovered in cell recovery solution, collected by centrifugation at 650 rpm for 5 min at 4° C., resuspended in TryPLE and incubated for 5 min at 37° C. Cells were then collected by centrifugation at 650 rpm for 5 min at 4° C. and resuspended in IEMM containing 10 µM ROCK inhibitor (RI). The cell suspension was passed through a 40 µm cell strainer and resuspended at 1×106 cells/mL in IEMM containing 10 µM RI. Cells were seeded at 5000 cells/well into multi-well plates and incubated for overnight at 37° C., 95% humidity and 5% CO$_2$ prior to assay.

Membrane Potential Dye Assay

Enteroid cells were incubated with test compound in IEMM for 18-24 h at 37° C., 95% humidity and 5% CO$_2$. Following compound incubations, a membrane potential dye assay was employed using a FLIPR Tetra to directly measure the potency and efficacy of the test compound on CFTR-mediated chloride transport following acute addition of 10 µM forskolin and 300 nM N-[2,4-bis(1,1-dimethylethyl)-5-hydroxyphenyl]-1,4-dihydro-4-oxoquinoline-3-carboxamide. Briefly, cells were washed 5 times in Bath 1 Buffer. Bath 1 Dye Solution was added and the cells were incubated for 25 min at ambient temperature. Following dye incubation, cells were washed 3 times in Chloride Free Dye Solution. Chloride transport was initiated by addition of Chloride Free Dye Stimulation Solution and the fluorescence signal was read for 15 min. The CFTR-mediated chloride transport for each condition was determined from the AUC of the fluorescence response to acute forskolin and 300 nM N-[2,4-bis(1,1-dimethylethyl)-5-hydroxyphenyl]-1,4-dihydro-4-oxoquinoline-3-carboxamide stimulation. Chloride transport was then expressed as a percentage of the chloride transport following treatment with 1 µM (14S)-8-[3-(2-{Dispiro[2.0.2.1]heptan-7-yl}ethoxy)-1H-pyrazol-1-yl]-12,12-dimethyl-2λ⁶-thia-3,9,11,18,23-pentaazatetracyclo[17.3.1.111,14.05,10]-tetracosa-1(22),5,7,9,19(23),20-hexaene-2,2,4-trione, 3 µM ((R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide and 300 nM acute N-[2,4-bis(1,1-dimethylethyl)-5-hydroxyphenyl]-1,4-dihydro-4-oxoquinoline-3-carboxamide triple combination positive control (% Activity). Table 3 provides CFTR modulating activity for Compound I and exemplary deuterated derivatives of Compound I.

TABLE 3

CFTR Modulating Activity for Compound I and Exemplary Deuterated Derivatives of Compound I

| Compound | Chemical Structure | Max. Activity | $EC_{50}$ |
| --- | --- | --- | --- |
| Compound I | 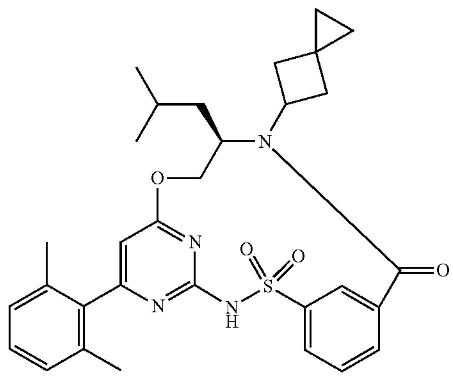 [SMILES: Cc1cccc(C)c1-c1cc2nc(n1)NS(=O)(=O)c1cccc(c1)C(=O)N(C1CC3(CC3)C1)[C@H](CC(C)C)CO2] | +++ | +++ |
| Compound Ia | 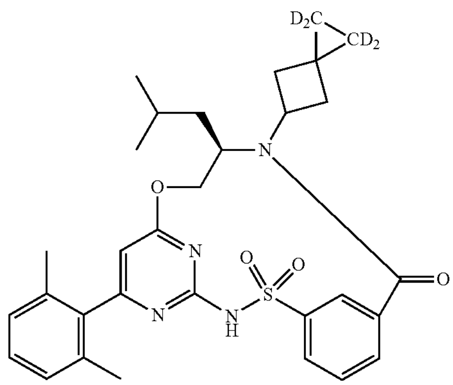 | +++ | +++ |
| Compound Ib | 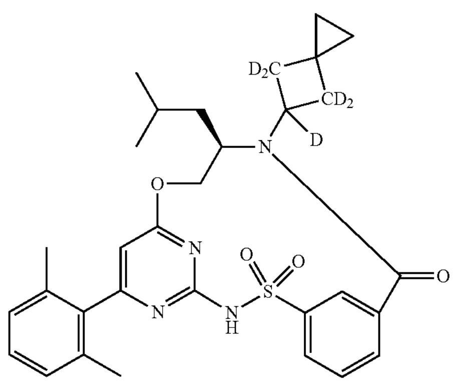 | +++ | +++ |
| Compound Ic | 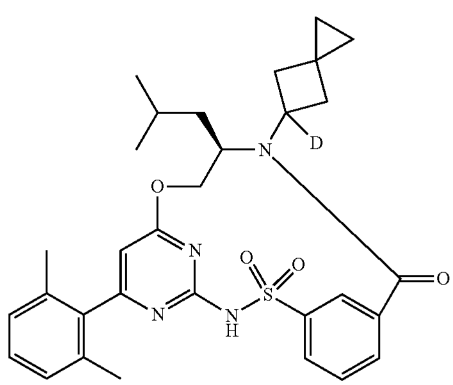 [SMILES: [2H]C1(N2C(=O)c3cccc(c3)S(=O)(=O)Nc3nc(cc(-c4c(C)cccc4C)n3)OC[C@H]2CC(C)C)CC2(CC2)C1] | +++ | +++ |

TABLE 3-continued

CFTR Modulating Activity for Compound I and Exemplary Deuterated Derivatives of Compound I

| Compound | Chemical Structure | Max. Activity | EC$_{50}$ |
|---|---|---|---|
| Compound Id | 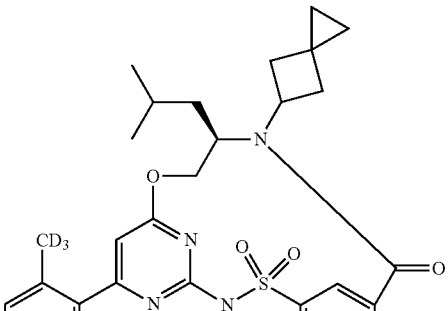 | +++ | +++ |

Max Activity: +++ is >60%; ++ is 30-60%; + is <30%.
EC$_{50}$: +++ is <1 μM.

OTHER EMBODIMENTS

The foregoing discussion discloses and describes merely exemplary embodiments of this disclosure. One skilled in the art will readily recognize, from such discussion and from the accompanying claims, that various changes, modifications, and variations can be made therein without departing from the spirit and scope of this disclosure as defined in the following claims.

We claim:

1. A compound selected from Compound I:

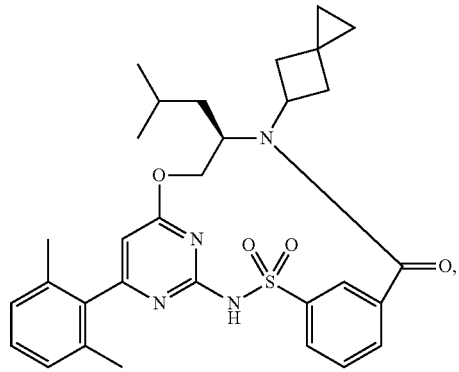

I a deuterated derivative of Compound I, and a pharmaceutically acceptable salt thereof.

2. The compound of claim 1, wherein the compound is Compound I.

3. The compound of claim 1, wherein the deuterated derivative of Compound I is selected from:

Compound Ia

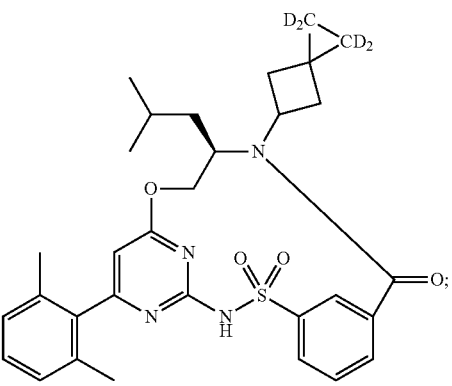

Ia

Compound Ib

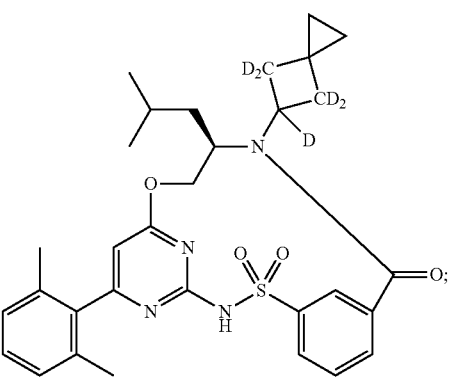

Ib

-continued

Compound Ic

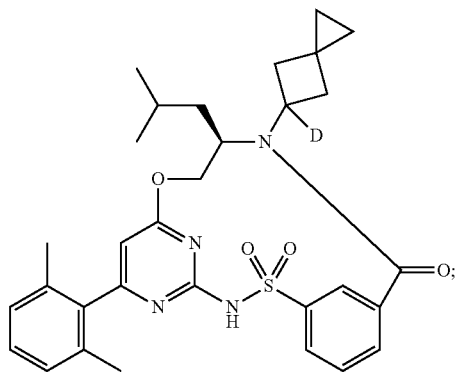

Compound Id

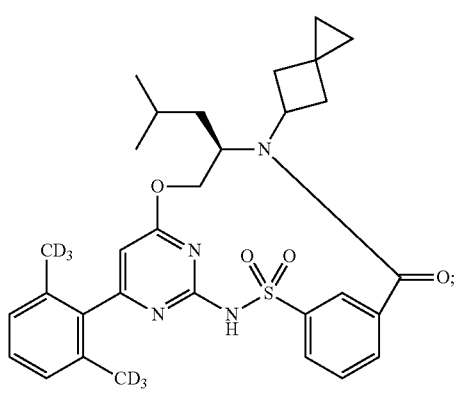

and a pharmaceutically acceptable salt thereof.

4. The compound of claim 1, wherein the compound is a potassium salt of Compound I.

5. The compound of claim 1, wherein the compound is a sodium salt of Compound I.

6. The compound of claim 1, wherein the compound is a calcium salt of Compound I.

7. A method of treating a cystic fibrosis transmembrane conductance regulator (CFTR)-mediated disorder, comprising administering an effective amount of the compound of claim 1 to a patient in need thereof.

8. The method of claim 7, wherein the CFTR-mediated disorder is cystic fibrosis (CF).

9. The method of claim 7, wherein the compound is Compound I or a pharmaceutically acceptable salt thereof.

10. The method of claim 7, further comprising administering one or more compounds selected from:

Compound II

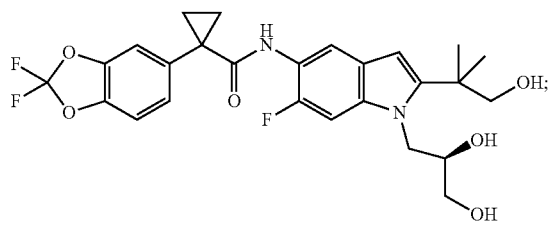

Compound III

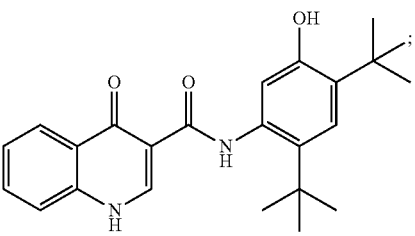

Compound III-d

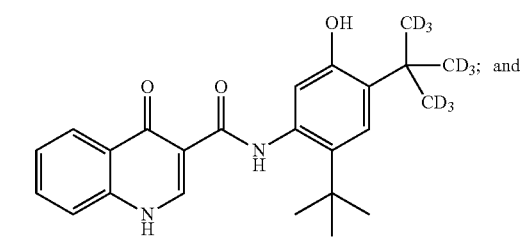

Compound IV

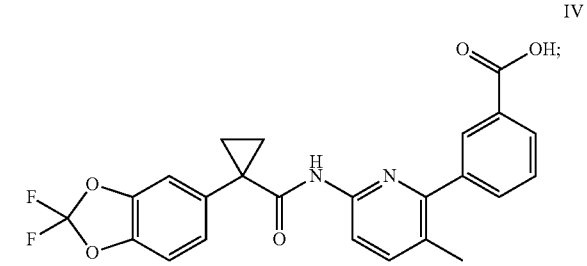

and a pharmaceutically acceptable salt of Compounds II, III, III-d, or IV.

11. The method of claim 10, wherein the method comprises administering:

(i) Compound I and (ii) Compound III or Compound III-d.

12. The method of claim 10, wherein the method comprises administering:

(i) Compound I, (ii) Compound II, and (iii) Compound III or Compound III-d.

13. A pharmaceutical composition comprising the compound of claim 1 and a pharmaceutically acceptable carrier.

14. The pharmaceutical composition of claim 13, wherein the compound is Compound I or a pharmaceutically acceptable salt thereof.

15. The pharmaceutical composition of claim 13, further comprising one or more compounds selected from:

Compound II

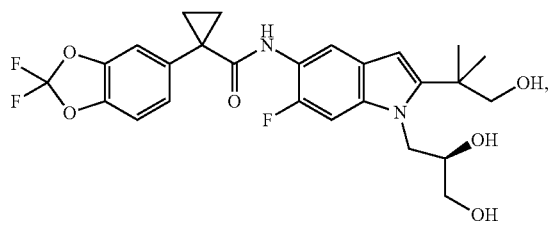

Compound III

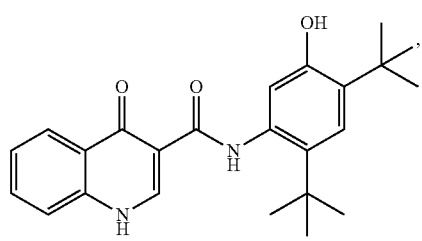

Compound III-d

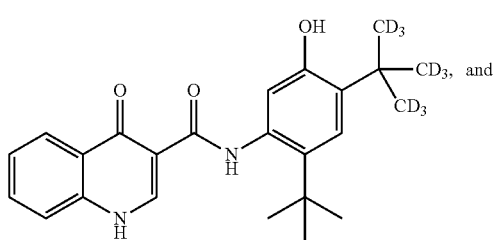

Compound IV

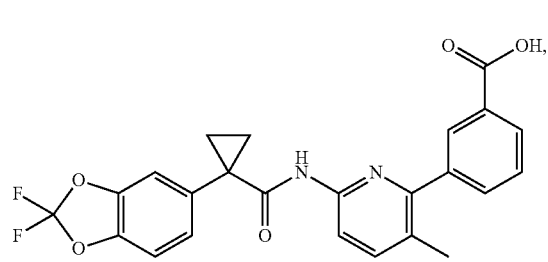

and a pharmaceutically acceptable salt of Compounds II, III, III-d, or IV.

16. The pharmaceutical composition of claim 15, wherein the pharmaceutical composition comprises:
 (i) Compound I and
 (ii) Compound III or Compound III-d.

17. The pharmaceutical composition of claim 15, wherein the pharmaceutical composition comprises:
 (i) Compound I,
 (ii) Compound II, and
 (iii) Compound III or Compound III-d.

18. A method of treating a CFTR-mediated disorder, comprising administering an effective amount of the pharmaceutical composition of claim 13 to a patient in need thereof.

19. A process for preparing Compound I, comprising reacting compound 8:

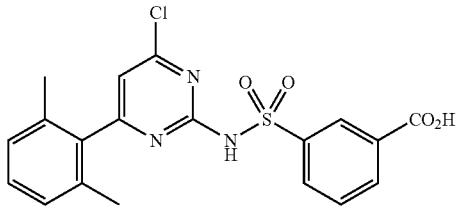

with compound 3:

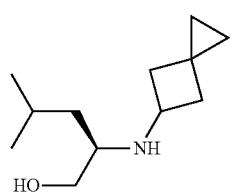

to produce Compound I:

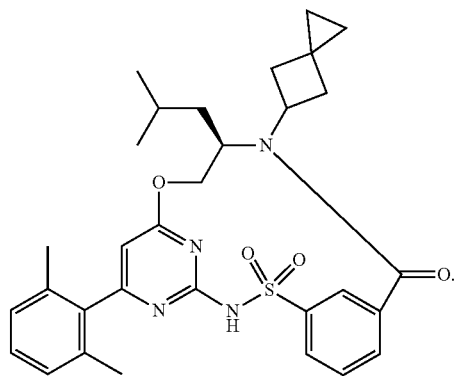

20. A process for preparing Compound I, comprising:
a) reacting compound 8:

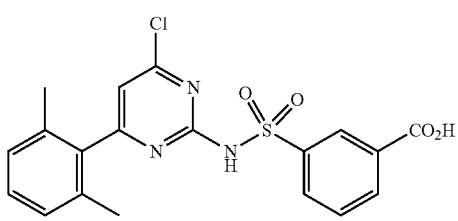

with compound 3:
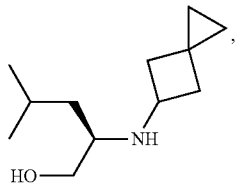
and subsequent treatment with HCl to produce compound 9:
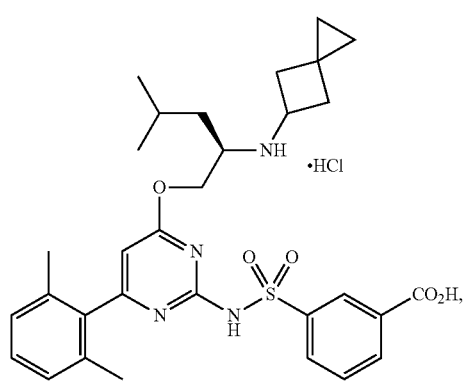
and
b) converting compound 9 into Compound I:
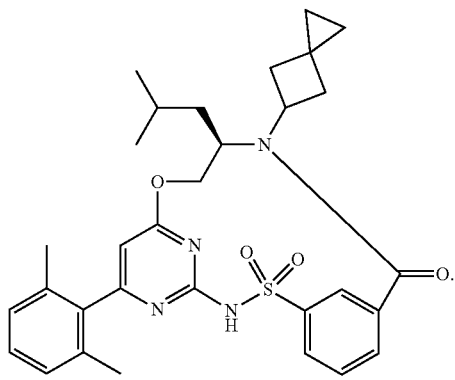
21. A process for preparing Compound Ia:
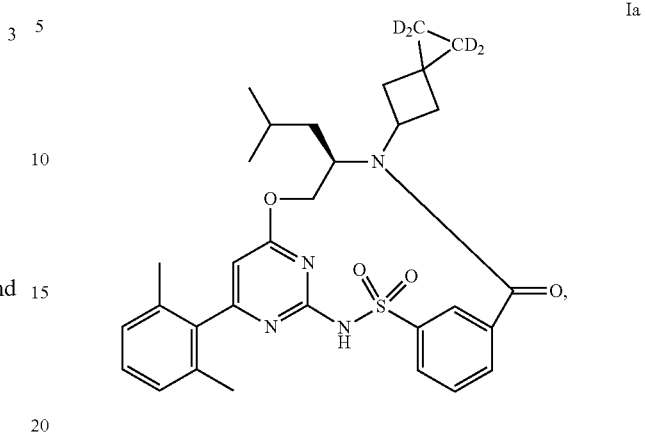
comprising converting compound 20:
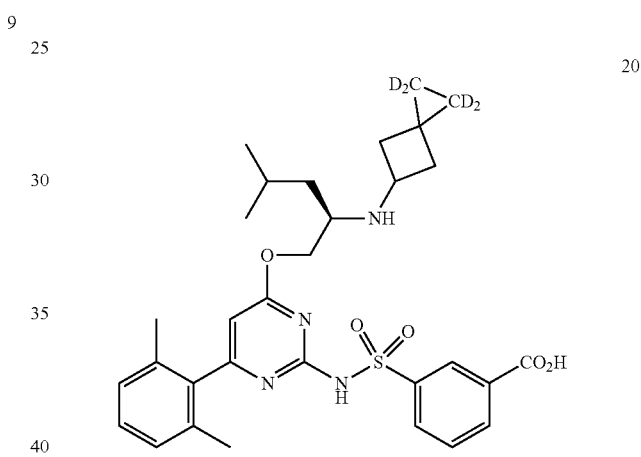
into compound Ia.
22. A process for preparing Compound Ib:
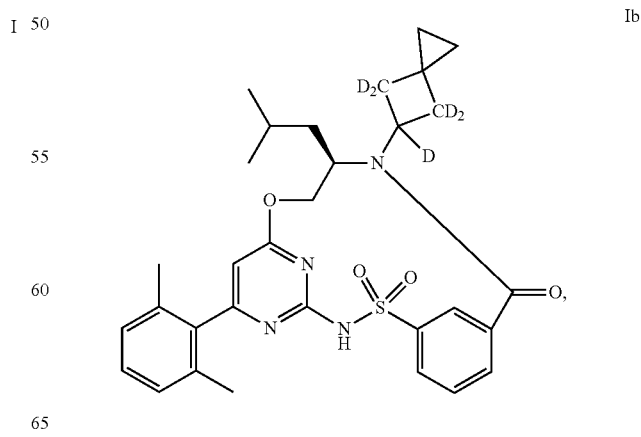

comprising converting compound 22:
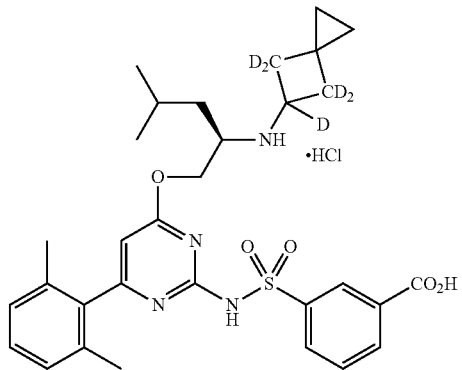
into compound Ib.
23. A process for preparing Compound Ic:
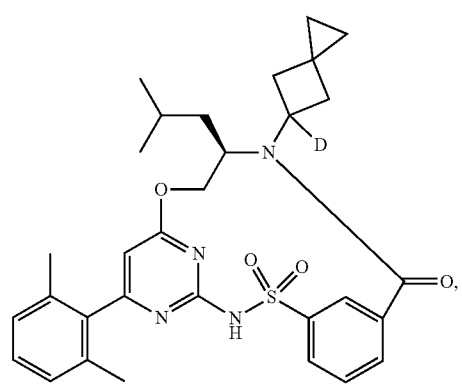
comprising converting compound 23:
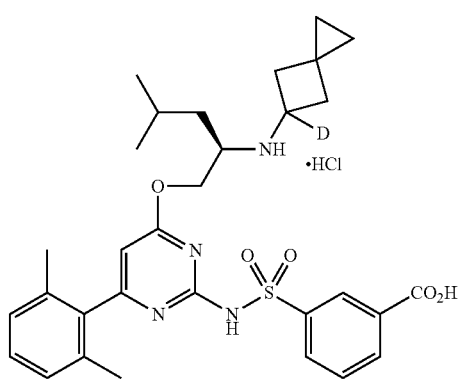
into compound Ic.
24. A process for preparing Compound Id:
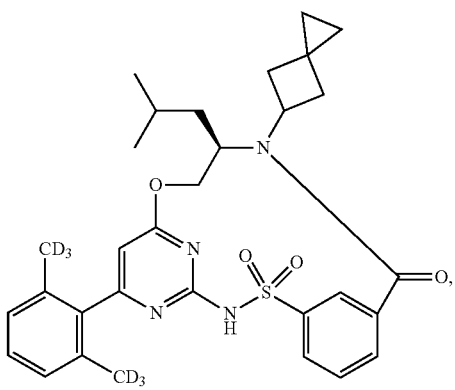
comprising converting compound 35:
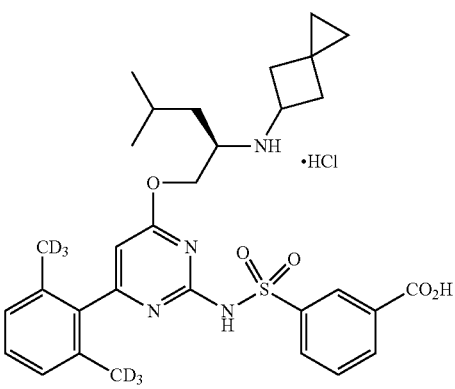
into compound Id.
25. A compound selected from compound 8:
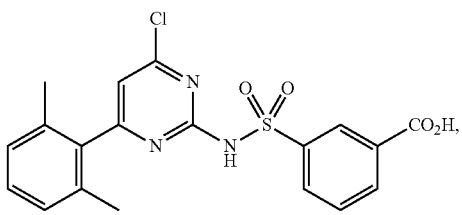
compound 18
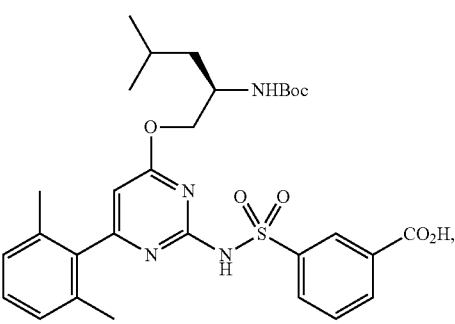

compound 19
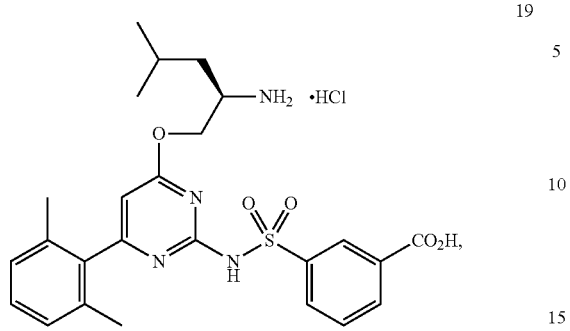
a deuterated derivative thereof, and a pharmaceutically acceptable salt of any of the foregoing.
* * * * *